US011883431B2

(12) United States Patent
Ji et al.

(10) Patent No.: US 11,883,431 B2
(45) Date of Patent: Jan. 30, 2024

(54) T-CELLS MODIFIED TO OVEREXPRESS PHF19

(71) Applicant: The United States of America, as represented by the Secretary, Department of Health and Human Services, Bethesda, MD (US)

(72) Inventors: Yun Ji, Germantown, MD (US); Luca Gattinoni, Washington, DC (US)

(73) Assignee: The United States of America, as represented by the Secretary, Department of Health and Human Services, Bethesda, MD (US)

(*) Notice: Subject to any disclaimer, the term of this patent is extended or adjusted under 35 U.S.C. 154(b) by 1050 days.

(21) Appl. No.: 16/619,570

(22) PCT Filed: Jun. 5, 2018

(86) PCT No.: PCT/US2018/036125
§ 371 (c)(1),
(2) Date: Dec. 5, 2019

(87) PCT Pub. No.: WO2018/226741
PCT Pub. Date: Dec. 13, 2018

(65) Prior Publication Data
US 2020/0289562 A1 Sep. 17, 2020

Related U.S. Application Data

(60) Provisional application No. 62/515,105, filed on Jun. 5, 2017.

(51) Int. Cl.
*A61K 35/17* (2015.01)
*A61P 35/00* (2006.01)
*C07K 14/435* (2006.01)
*C12N 15/63* (2006.01)
*C12N 5/0783* (2010.01)
*C12N 5/10* (2006.01)

(52) U.S. Cl.
CPC .............. *A61K 35/17* (2013.01); *A61P 35/00* (2018.01); *C07K 14/435* (2013.01); *C12N 5/0636* (2013.01); *C12N 5/0638* (2013.01); *C12N 5/10* (2013.01); *C12N 15/63* (2013.01); *C12N 2510/00* (2013.01)

(58) Field of Classification Search
CPC .... C12N 5/0638; C12N 15/63; C12N 5/0636; C12N 5/10; C12N 2510/00; A61K 35/17; A61P 35/00; A61P 31/12; C07K 14/435
USPC .......................... 424/93.71, 93.2; 435/372.3
See application file for complete search history.

(56) References Cited

U.S. PATENT DOCUMENTS

| 7,820,174 | B2 | 10/2010 | Wang et al. |
| 8,216,565 | B2 | 7/2012 | Restifo et al. |
| 8,465,743 | B2 | 6/2013 | Rosenberg et al. |
| 8,785,601 | B2 | 7/2014 | Rosenberg et al. |
| 9,266,960 | B2 | 2/2016 | Morgan et al. |
| 9,345,748 | B2 | 5/2016 | Morgan et al. |
| 2014/0120136 | A1* | 5/2014 | Katsikis ............... C12N 5/0636 424/234.1 |
| 2014/0274909 | A1 | 9/2014 | Orentas et al. |

FOREIGN PATENT DOCUMENTS

WO WO 2014/066137 A1 5/2014
WO WO-2014066137 A1 * 5/2014 ......... A61K 31/7105

OTHER PUBLICATIONS

Ji et al., "miR-155 harnesses Phf19 to potentiate cancer immunotherapy through epigenetic reprogramming of CD8+ T cell fate". Nature Communications. May 14, 2019. 10 (2157): 1-12 (Year: 2019).*
Bommhardt et al., "Akt Decreases Lymphocyte Apoptosis and Improves Survival in Sepsis". J Immunol. Jun. 15, 2004; 172 (12): 7583-7591 (Year: 2004).*
Ghislin et al., "PHF19 and Akt control the switch between proliferative and invasive states in melanoma". Cell Cycle. Apr. 12, 2012; 11(8): 1634-1645 (Year: 2012).*
Ballaré et al., "Phf19 links methylated Lys36 of histone H3 to regulation of Polycomb activity", *Nat. Struct. Mol. Biol.*, 19(12): 1257-1265 (2012).
Brien et al., "A chromatin-independent role of Polycomb-like 1 to stabilize p53 and promote cellular quiescence", *Genes Dev.*, 29: 2231-2243 (2015).
Brien et al., "Polycomb PHF19 binds H3K36me3 and recruits PRC2 and demethylase NO66 to embryonic stem cell genes during differentiation", *Nat. Struct. Mol. Biol*, 19(12): 1273-1283 (2012).
Cai et al., "An H3K36 Methylation-Engaging Tudor Motif of Polycomb-like Proteins Mediates PRC2 Complex Targeting", *Mol. Cell.*, 49: 571-582 (2013).
Dudda et al., "MicroRNA-155 Is Required for Effector CD8+ T Cell Responses to Virus Infection and Cancer", *Immunity*, 38: 742-753 (2013).
Gattinoni et al., "Paths to stemness: building the ultimate antitumour T cell", *Nat. Rev. Cancer*, 12: 671-684 (2012).

(Continued)

*Primary Examiner* — Anne Marie S Wehbe
*Assistant Examiner* — Hanan Isam Abuzeineh
(74) *Attorney, Agent, or Firm* — Leydig, Voit & Mayer, Ltd.

(57) ABSTRACT

Provided is a mammalian T cell modified to express the Phf19 at a level that is higher than the level of Phf19 expressed by a T cell that has not been modified to express Phf19. Provided is a genetically-modified mammalian T cell comprising a genetic expression vector comprising (a) virally-, bacterially-, or both virally- and bacterially-derived genetic sequences and (b) a genetic sequence encoding Phf19, whereby the genetic sequence encoding Phf19 within the vector is expressed within the T cell. Pharmaceutical compositions, methods of treating a disease, and methods of inhibiting the differentiation of T cells by epigenetic reprogramming are also provided.

17 Claims, 38 Drawing Sheets

Specification includes a Sequence Listing.

(56) References Cited

OTHER PUBLICATIONS

Ghislin et al., "PHF19 and Akt control the switch between proliferative and invasive states in melanoma", *Cell Cycle*, 11(8): 1634-1645 (2012).
Hunkapiller et al., "Polycomb-Like 3 Promotes Polycomb Repressive Complex 2 Binding to CpG Islands and Embryonic Stem Cell Self-Renewal", *PLOS Genet.*, 8(3): pp. 1-24, (2012) e1002576.
Ji et al., "Enhancing adoptive T cell immunotherapy with microRNA therapeutics", *Semin. Immunol.*, 28(1): 45-53 (2015).
Ji et al., "miR-155 augments CD8+T-cell antitumor activity in lymphoreplete hosts by enhancing responsiveness to homeostatic $\gamma_c$ cytokines", *Proc. Natl. Acad. Sci.*, 112(2): 476-481 (2015).
Ji et al., "miR-155 releases the brakes on antitumor T cells", *OncoImmunology*, 4(8): pp. 1-3 (2015) e1026533.
Li et al., "Targeting miR-155 inhibits survival of melanoma cells by upregulating FOXO3a", *Int. J. Clin. Exp. Pathol.*, 10(3): 2988-2996 (2017).
Ling et al., "microRNA-155 regulates cell proliferation and invasion by targeting FOXO3a in glioma", *Oncol. Reports*, 30: 2111-2118 (2013).
Martin-Perez et al., "Polycomb proteins in hematologic malignancies", *Blood*, 116: 5465-5475 (2010).
Muranski et al., "Increased intensity lymphdepletion and adoptive immunotherapy—how far can we go?", *Nat. Clin. Pract. Oncol.*, 3(12): 668-681 (2006).
Pan et al., "G9a orchestrates PCL3 and KDM7A to promote histone H3K27 methylation", *Sci. Rep.*, 5: 18709 (2015).
Vizán et al., "Role of PRC2-associated factors in stem cells and disease", *FEBS J.*, 282: 1723-1735 (2015).
Xu et al., "MicroRNA-195-5p acts as an anti-oncogene by targeting PHF19 in hepatocellular carcinoma", *Oncol. Rep.*, 34: 175-182 (2015).
European Patent Office, International Search Report issued in International Application No. PCT/US2018/036125 (dated Sep. 24, 2018).
European Patent Office, Written Opinion of the International Searching Authority issued in International Application No. PCT/US2018/036125 (dated Sep. 24, 2018).
The International Bureau of WIPO, International Preliminary Report on Patentability issued in International Application No. PCT/US2018/036125 (dated Dec. 19, 2019).

\* cited by examiner

```
                    W41     Y47
Wt   ...SKVTEGQFVLCR|W|TDGLY|Y|LGKIKRVSSPKQ...  SEQ ID NO: 9
Mut  ...SKVTEGQFVLCR|C|TDGLY|A|LGKIKRVSSPKQ...  SEQ ID NO: 10
```

FIG. 5A

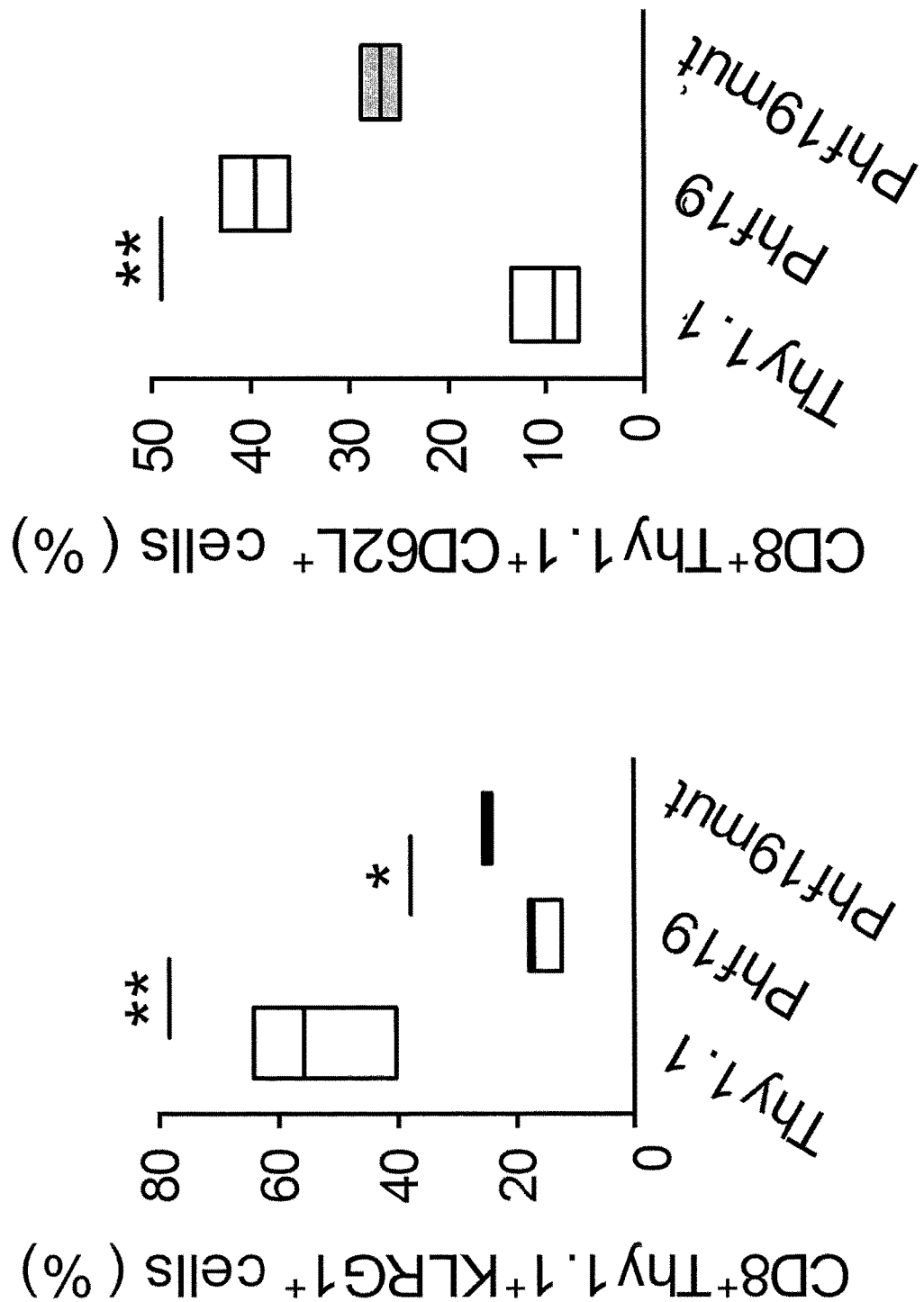

PHF19 mediates a similar transcriptional program in both Human and Mouse

Red: genes significantly upregulated in Human Phf19-overexpressing CD8+ T cells compared to controls Blue: genes significantly upregulated in mouse Wild-type compared to Phf19-deficient CD8+ T cells

T-CELLS MODIFIED TO OVEREXPRESS PHF19

CROSS-REFERENCE TO RELATED APPLICATIONS

This application is the U.S. national phase of International Patent Application PCT/US2018/036125, filed Jun. 5, 2018, which claims the benefit of U.S. Provisional Patent Application 62/515,105, filed Jun. 5, 2017, both of which are hereby incorporated by reference in their entireties herein.

STATEMENT REGARDING FEDERALLY SPONSORED RESEARCH OR DEVELOPMENT

This invention was made with Government support under project number ZIA BC 011480 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 36,176 Byte ASCII (Text) file named "746570 ST25.txt," created on Nov. 19, 2019.

BACKGROUND OF THE INVENTION

Adoptive cell transfer has emerged as a promising therapy for patients with advanced cancer. However, obstacles to the overall success of adoptive cell therapy still exist. For example, the in vivo proliferation, persistence, and release of high amounts of proinflammatory cytokines can, in some cases, decrease following adoptive transfer. Alternatively or additionally, in some cases, transferred cells, such as T cells, rapidly lose their proliferative and effector capacities following adoptive transfer as they enter into a state of functional exhaustion. T cell exhaustion is a state of T cell dysfunction that arises during many chronic infections and cancer. It is defined by poor effector function, sustained expression of inhibitory receptors, and a transcriptional state distinct from that of functional effector or memory T cells.

In spite of considerable research into methods of producing cells for adoptive cell transfer therapy and treatments for cancer and viral diseases, there still exists a need for improved methods for producing cells for adoptive cell transfer therapy and treating and/or preventing cancer and viral diseases.

BRIEF SUMMARY OF THE INVENTION

An embodiment of the invention provides a T cell (which can be isolated or purified) modified to express Phf19 at a level that is higher than the level of Phf19 expressed by a T cell that has not been modified to express Phf19. In some embodiments of the invention, the T cell comprises a genetic expression vector encoding Phf19. An embodiment of the invention provides a genetically-modified mammalian T cell (which also can be isolated or purified) comprising a genetic expression vector comprising (a) virally-, bacterially-, or both virally- and bacterially-derived genetic sequences and (b) a genetic sequence encoding Phf19, whereby the genetic sequence encoding Phf19 within the vector is expressed within the T cell. In some embodiments of the invention, the T cell is a CD8$^+$ T cell. In some embodiments, the T cell comprises an antigen-specific receptor, wherein the antigen-specific receptor is a T cell receptor (TCR) or a chimeric antigen receptor (CAR).

An embodiment of the invention provides a pharmaceutical composition comprising at least one or two of the inventive T cells (which also can be isolated or purified), which have been modified to express Phf19 at a level that is higher than the level of Phf19 expressed by a T cell that has not been modified to express Phf19, and a pharmaceutically acceptable carrier. In some embodiments of the invention, the T cells in the pharmaceutical composition comprise a genetic expression vector encoding Phf19, such as a vector comprising (a) virally-, bacterially-, or both virally- and bacterially-derived genetic sequences and (b) a genetic sequence encoding Phf19, whereby the genetic sequence encoding Phf19 within the vector is expressed within the T cell. In some embodiments of the invention, the T cells in the pharmaceutical composition are CD8$^+$ T cells.

An embodiment of the invention provides a method for treating cancer or chronic viral disease in a mammal. In some embodiments of the invention, the method comprises administering to the mammal an effective amount of T cells modified to express Phf19 at a level that is higher than the level of Phf19 expressed by a T cell that has not been modified to express Phf19, wherein the T cells can also be isolated or purified. In some embodiments of the invention, the method comprises administering to the mammal a pharmaceutical composition comprising at least one or two T cells, which have been modified to express Phf19 at a level that is higher than the level of Phf19 expressed by a T cell that has not been modified to express Phf19, and a pharmaceutically acceptable carrier. In some embodiments of the invention, the method comprises administering to the mammal an effective amount of genetically-modified mammalian T cells comprising a genetic expression vector comprising (a) virally-, bacterially-, or both virally- and bacterially-derived genetic sequences and (b) a genetic sequence encoding Phf19, whereby the genetic sequence encoding Phf19 within the vector is expressed within the T cell(s). In some embodiments of the invention, the method comprises administering to the mammal a pharmaceutical composition comprising at least one or two T cells comprising a genetic expression vector comprising (a) virally-, bacterially-, or both virally- and bacterially-derived genetic sequences and (b) a genetic sequence encoding Phf19, whereby the genetic sequence encoding Phf19 within the vector is expressed within the isolated or purified T cell, and a pharmaceutically acceptable carrier.

An embodiment of the invention provides a method for inhibiting T cell terminal differentiation and exhaustion. In one aspect, this method comprises modifying the T cell to express Phf19 at a level that is higher than the level of Phf19 expressed by a T cell that has not been modified, wherein the increased expression of Phf19 inhibits T cell terminal differentiation and exhaustion when compared with a T cell not modified to express Phf19. In another aspect, this method comprises introducing a genetic expression vector into the T cell, wherein the vector comprises (a) virally-, bacterially-, or both virally- and bacterially-derived genetic sequences and (b) a genetic sequence encoding Phf19, whereby the genetic sequence encoding Phf19 within the vector is expressed within the T cell.

BRIEF DESCRIPTION OF THE SEVERAL VIEWS OF THE DRAWING(S)

Figure 1A:
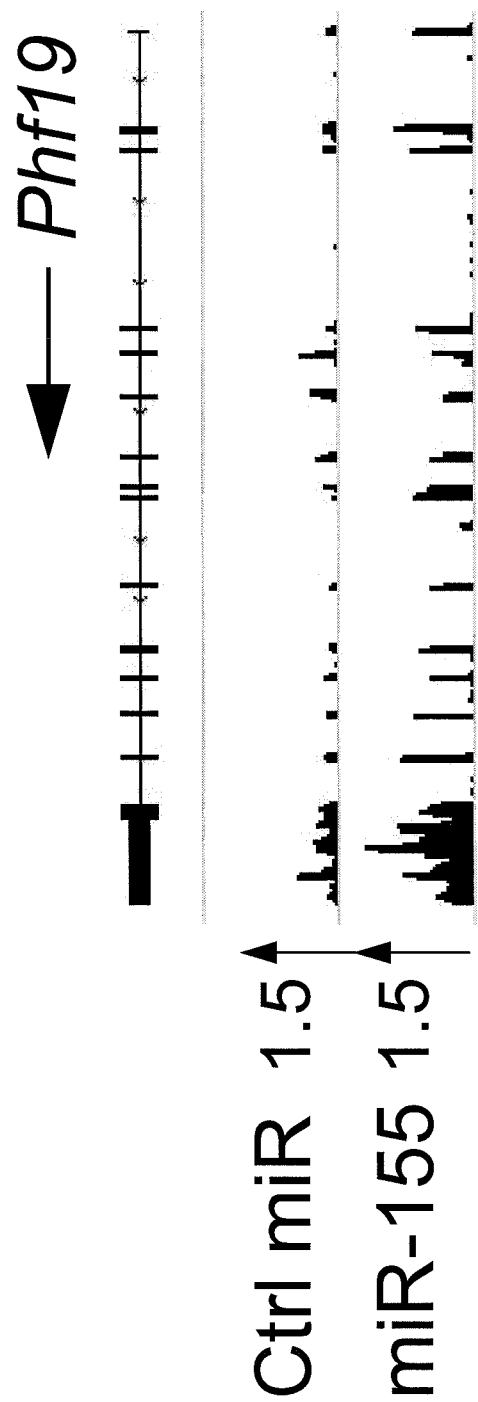
FIG. 1A shows RNA-seq reads of Phf19 mRNA in miR-155 and Ctrl-miR-overexpressing cells.
Figure 1C:
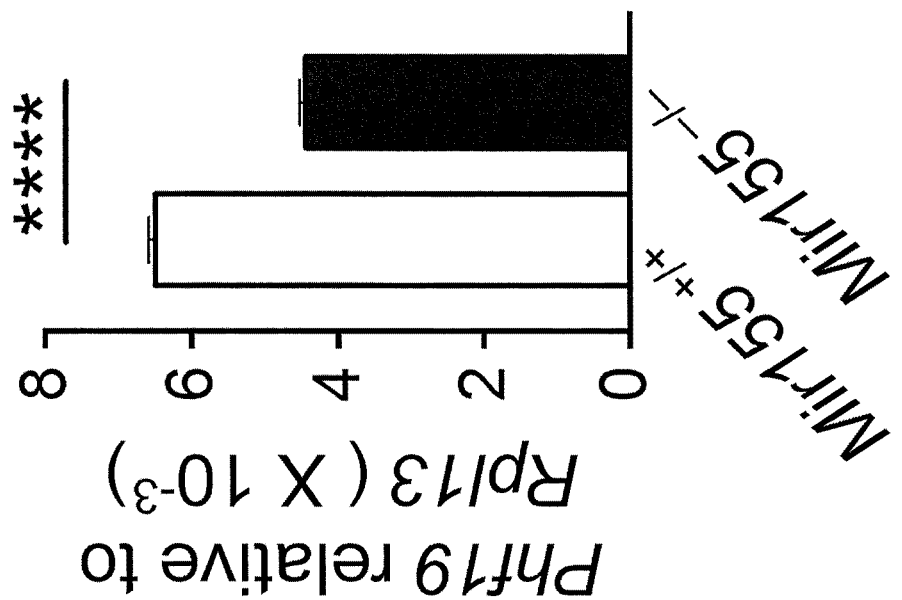
FIG. 1C is a bar graph showing RT-PCR of Phf19 mRNA in in vitro activated KLRG1$^-$ miR-155 sufficient and deficient CD8$^+$ T cells. Bars (mean±s.e.m. of technical triplicates) are relative to Rpl13 mRNA.
Figure 1B:
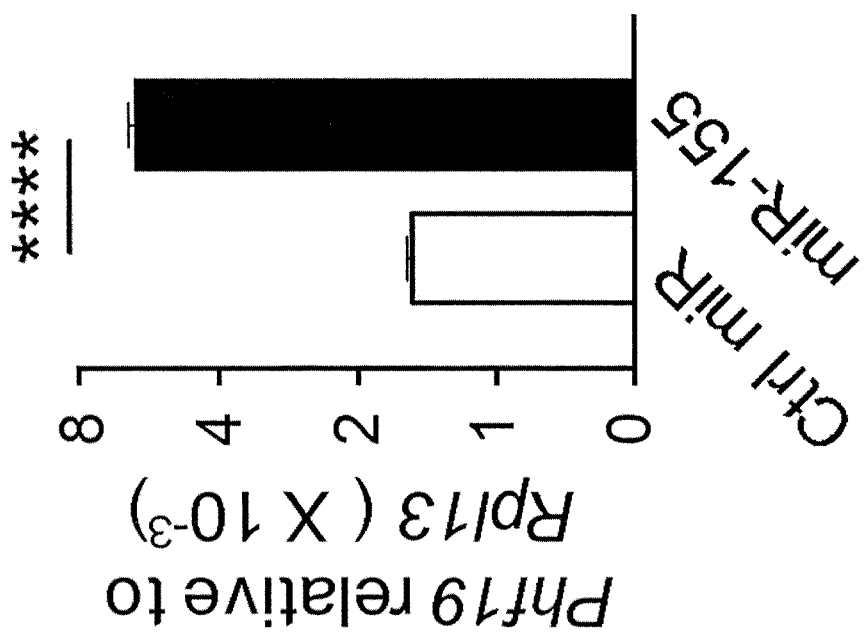
FIG. 1B is a bar graph showing RT-PCR of Phf19 mRNA in miR-155 and Ctrl-miR-overexpressing cells. Bars (mean±s.e.m. of technical triplicates) are relative to Rpl13 mRNA.
Figure 1D:
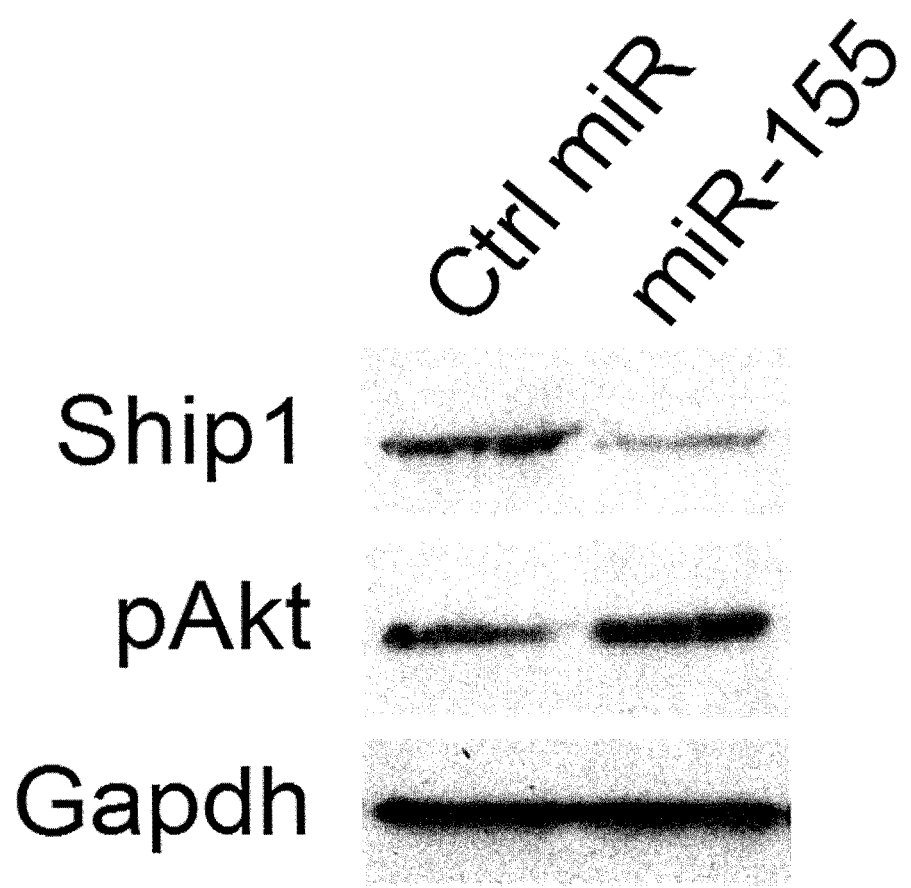
FIG. 1D is an image of a gel showing Ship1 and pAkt levels in miR-155-overexpressing cells assessed by Immunoblot. Gapdh was used as the normalizing control.
Figure 1E:
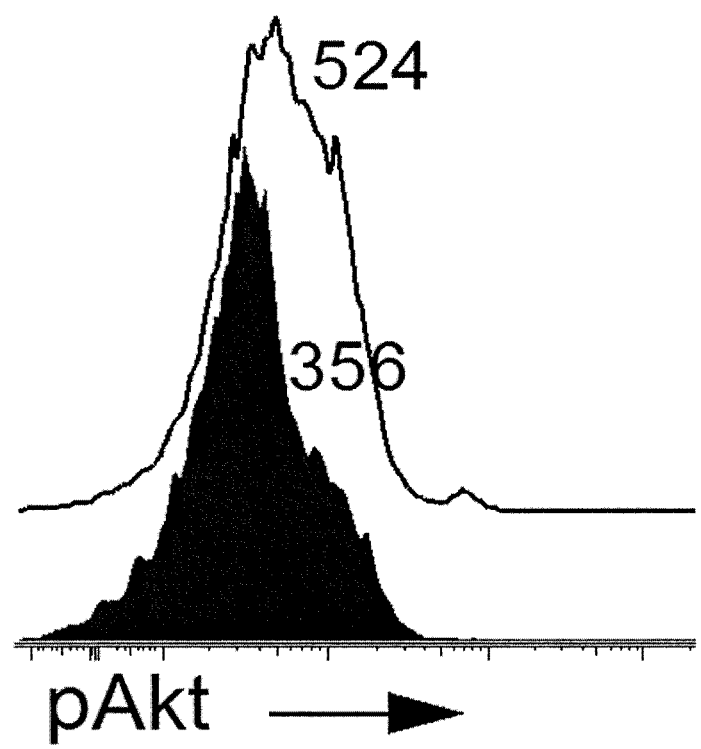
FIG. 1E is a histogram showing pAkt levels of in vitro activated KLRG1$^-$ miR-155 sufficient and deficient CD8$^+$ T cells assessed by flow cytometry.
Figure 1F:
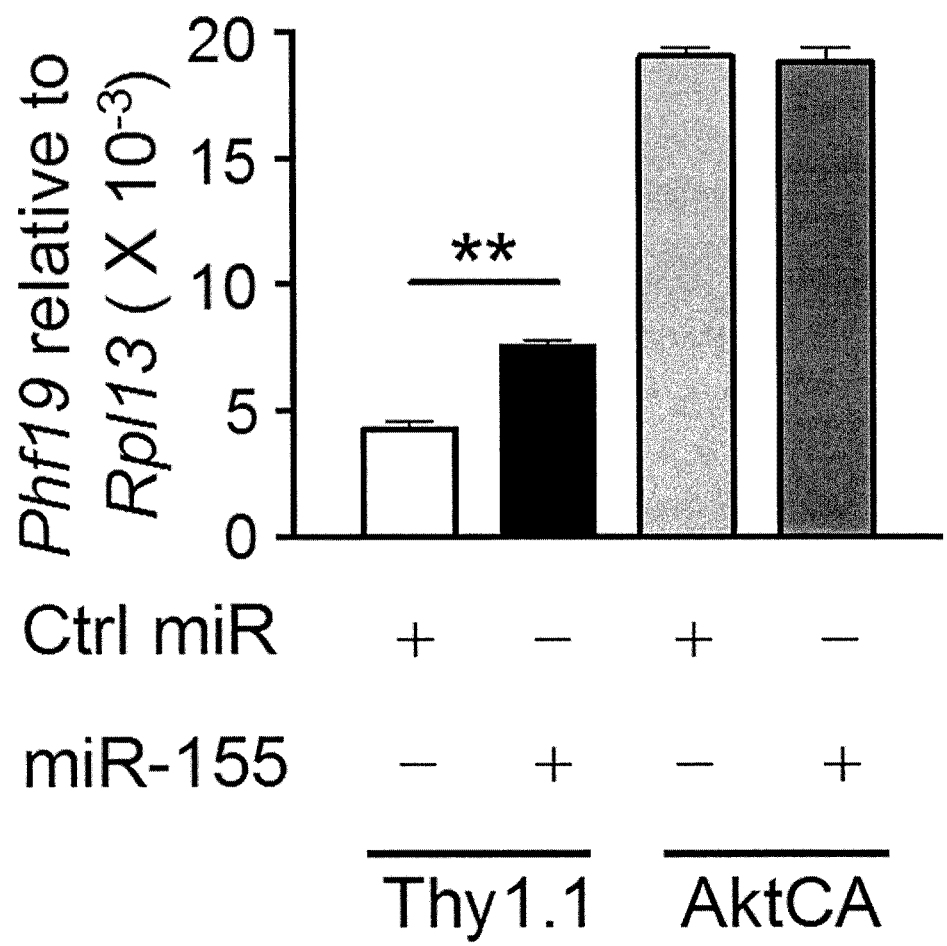
FIG. 1F is a bar graph showing RT-PCR of the expression of Phf19 mRNA in CD8$^+$ T cells overexpressing miR-155 and Ctrl-miR together with Thy1.1 or constitutively active Akt (AktCA). Bars represent the mean±s.e.m. of technical triplicates.
Figure 1G:
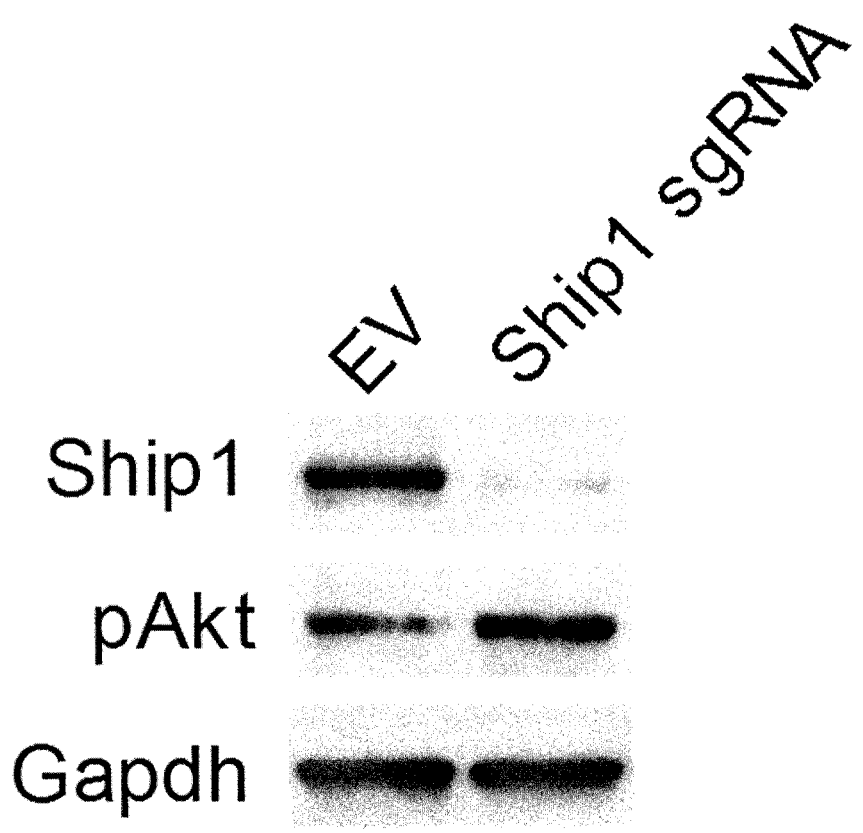
FIG. 1G is an image of a gel showing Ship1 and pAkt levels in Cas9$^+$ CD8$^+$ T cells transduced with Ship 1-specific gRNA assessed by Immunoblot. Gapdh was used as the normalizing control.
Figure 1H:
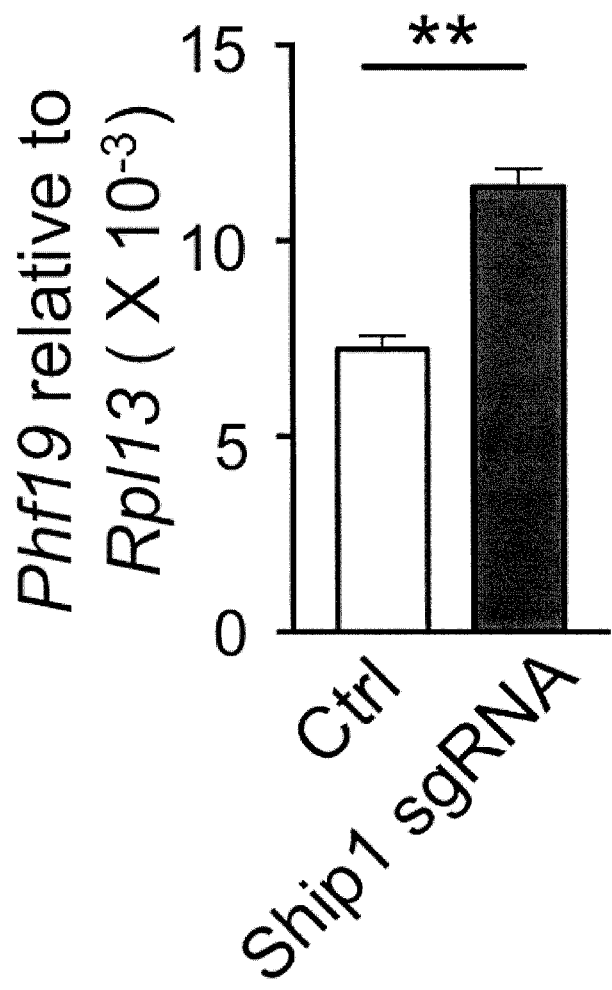

FIG. 1H is a bar graph showing RT-PCR of Phf19 mRNA in Cas9$^+$ CD8$^+$ T cells transduced with Ship1-specific gRNA or control. Bars represent the mean±s.e.m. of technical triplicates. Data are representative of two independent experiments. *=P<0.05; =P<0.01; **=P<0.001 (unpaired two-tailed Student's t-test).

Figure 2B:
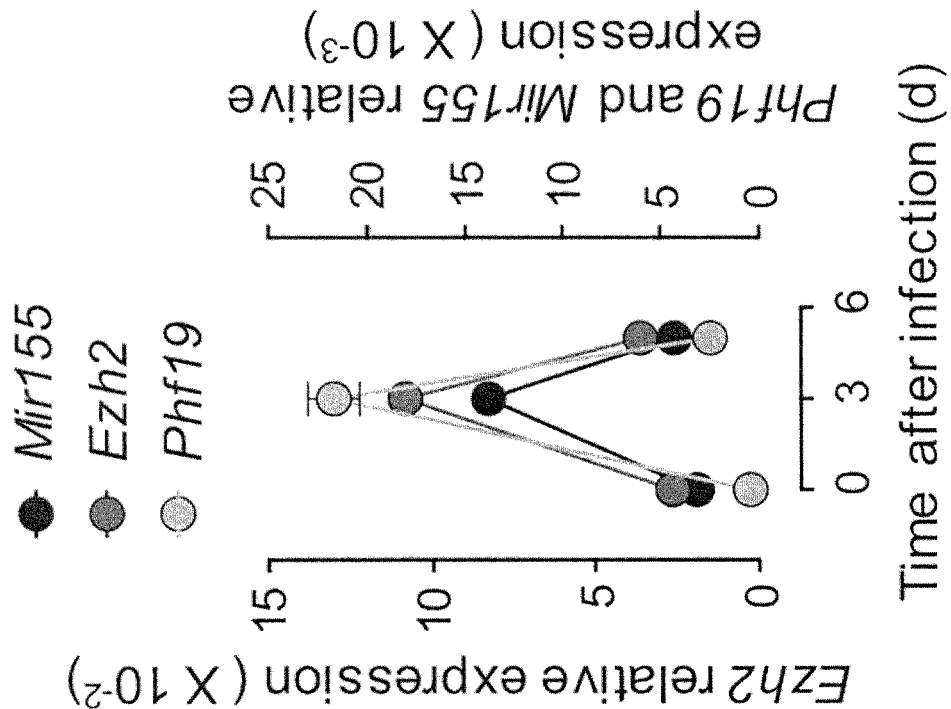
Figure 2A:
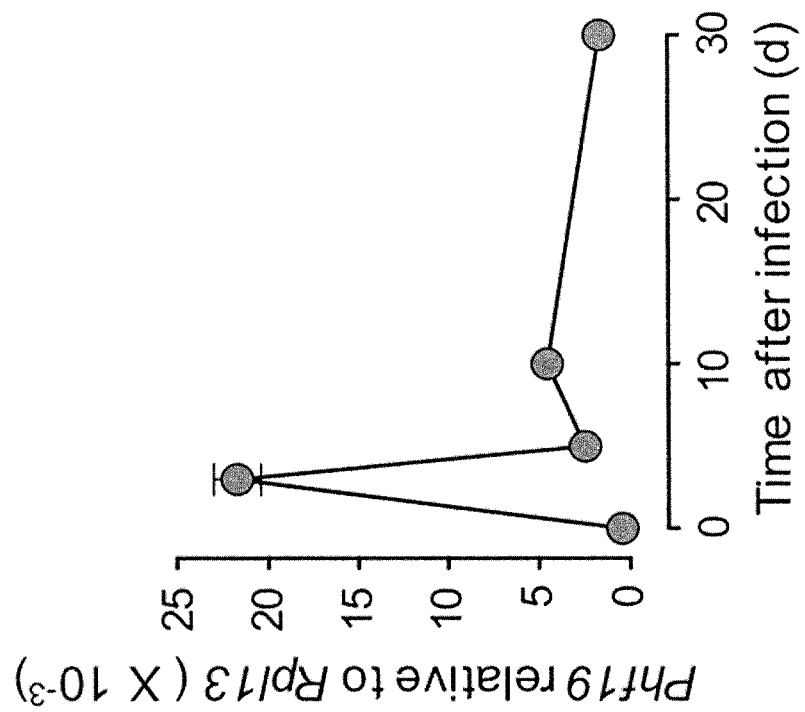

FIG. 2A is a graph showing the expression of Phf19 mRNA at indicated time points after transferring $10^5$ pmel-1 CD8$^+$ Ly5.1$^+$ T cells into wild-type mice in conjunction with gp100-VV.

FIG. 2B is a graph showing the expressions of Mir155, Ezh2 and Phf19 mRNA at indicated time points after transferring $10^5$ pmel-1 CD8$^+$ Ly5.1$^+$ T cells into wild-type mice in conjunction with gp100-VV. Ezh2 and Phf19 levels are relative to Rpl13, Mir155 levels are relative to U6.

Figure 2C:
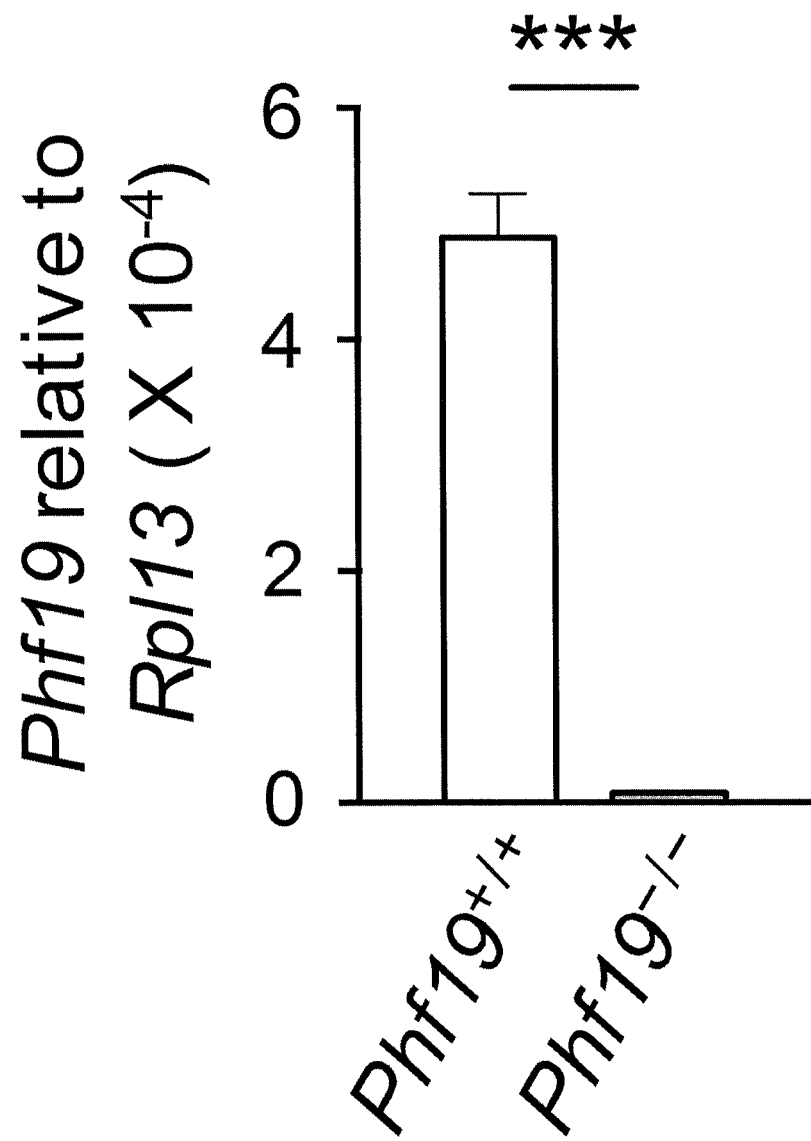

FIG. 2C is a bar graph showing RT-PCR of Phf19 levels in Phf19$^{+/+}$ or Phf19$^{-/-}$ CD8$^+$ T cells. Bars (mean±s.e.m. of technical triplicates) are relative to Rpl13 mRNA.

Figure 2D:
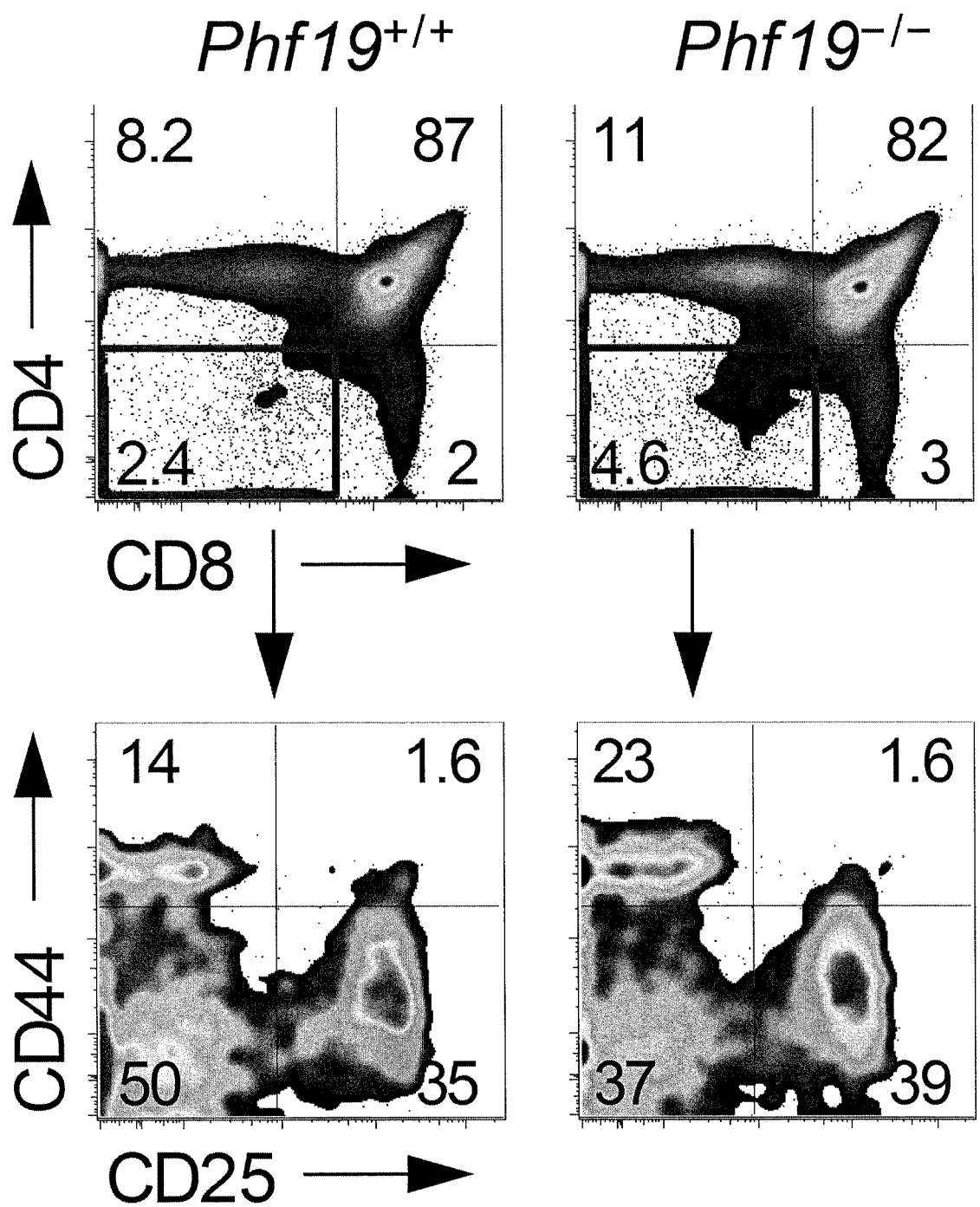

FIG. 2D shows density plots representing flow cytometry of thymocytes from Phf19$^{+/+}$ or Phf19$^{-/-}$ thymus. Numbers adjacent to outlined areas indicate percentage after gating on CD3$^+$ cells (top), CD3$^+$CD4$^-$CD8$^-$ cells (bottom).

Figure 2E:
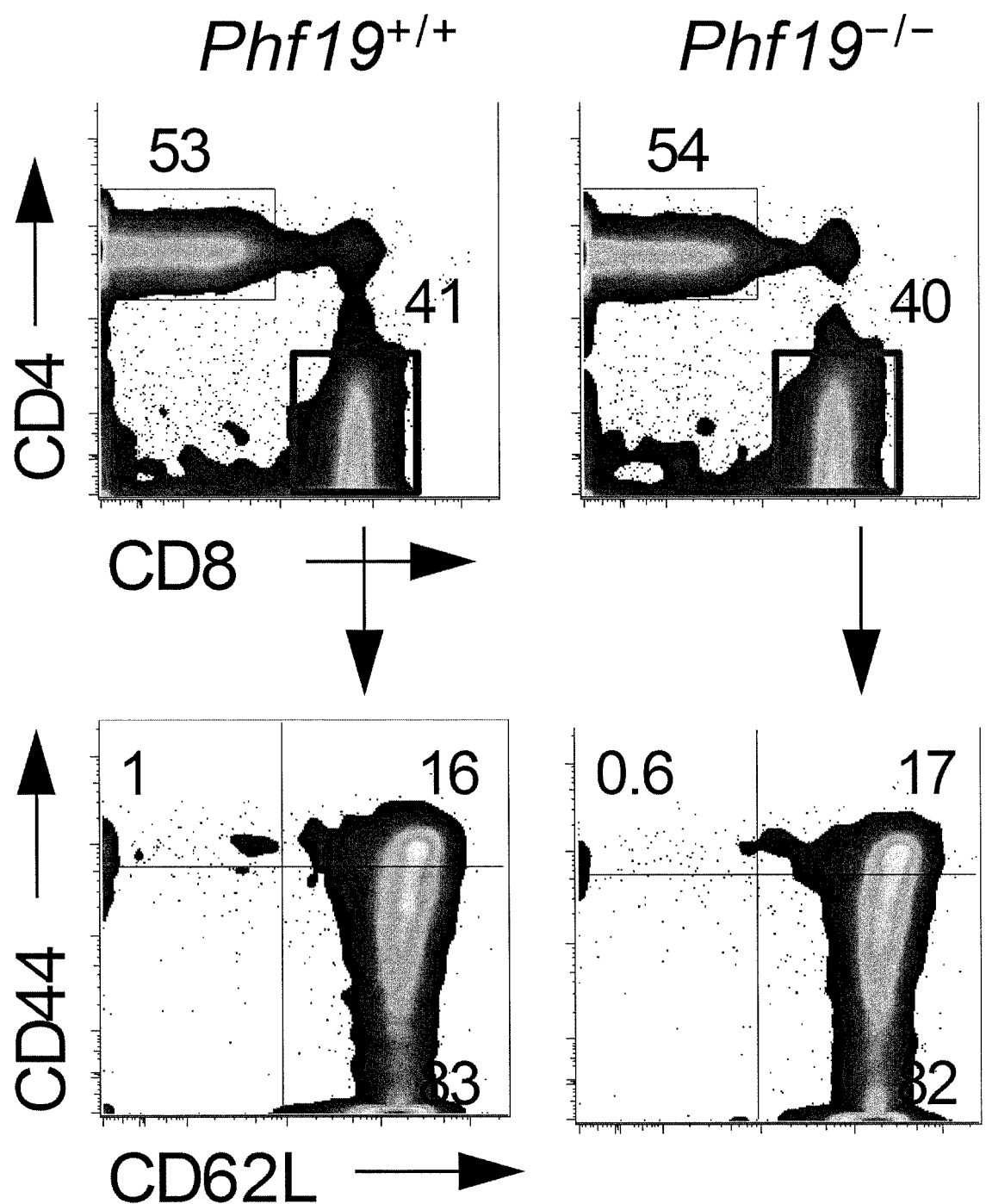

FIG. 2E shows density plots of representing flow cytometry of splenocytes from Phf19$^{+/+}$ or Phf19$^{-/-}$ spleen. Numbers adjacent to outlined areas indicate percentage after gating on CD3$^+$ cells (top), CD3$^+$CD8$^+$ cells (bottom)

Figure 2F:
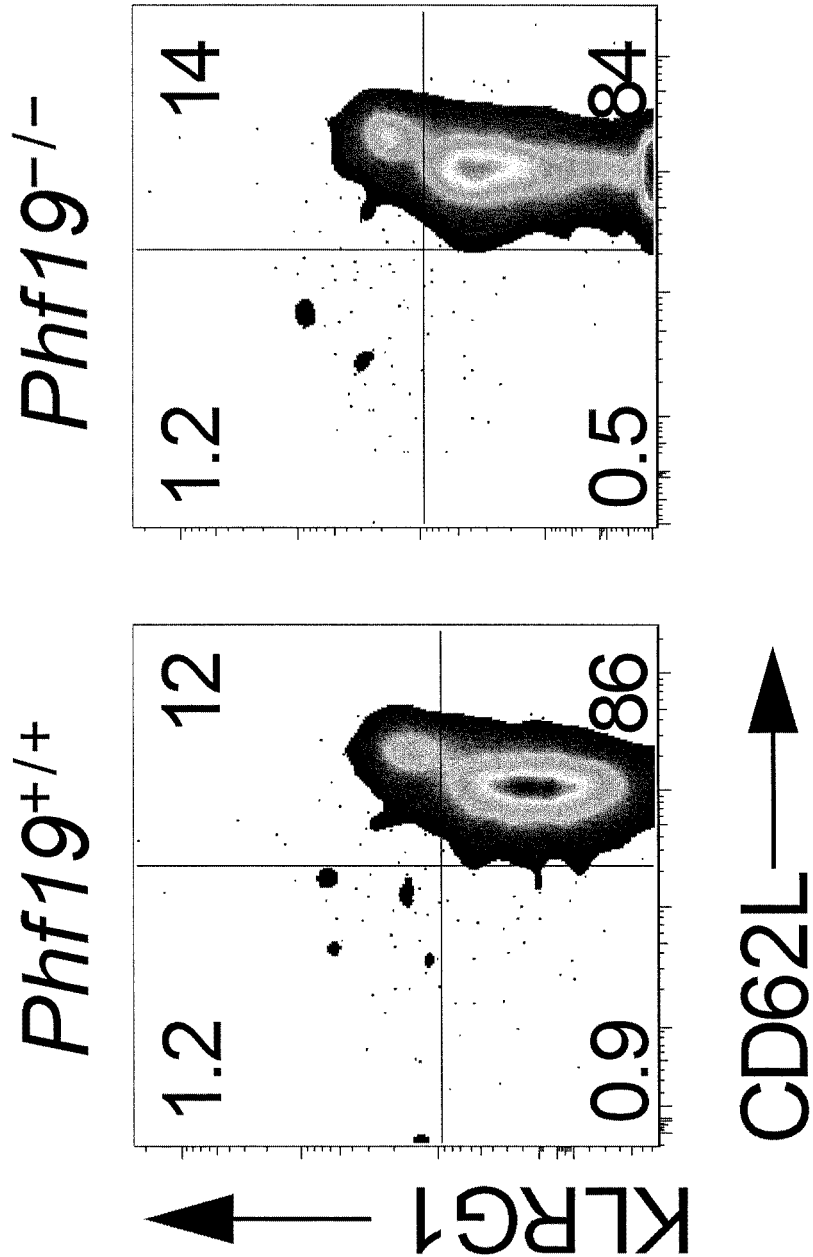

FIG. 2F shows density plots representing flow cytometry analysis of splenocytes from pmel-1 Phf19$^{+/+}$ or Phf19$^{-/-}$ spleen. Numbers adjacent to outlined areas indicate percentage after gating on CD8$^+$ cells. Data are presented as the mean of three to four individual mice in two independent experiments. ***=P<0.005 (unpaired two-tailed Student's t-test).

Figure 2G:
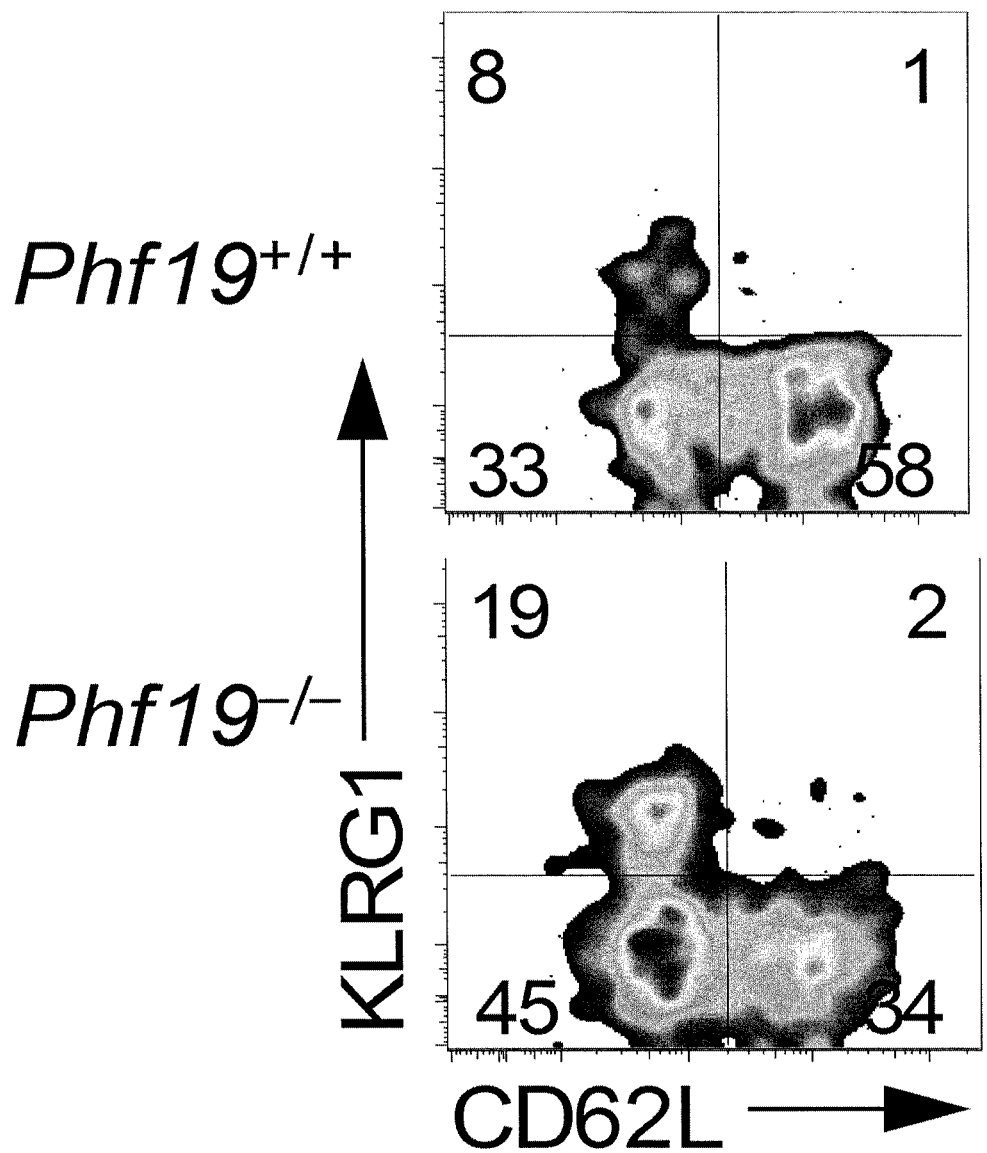

FIG. 2G is a density plot showing flow cytometry of live CD8$^+$ Ly5.1$^+$ T cells in the spleen 5 days after transfer of $3\times10^5$ naïve pmel-1 CD8$^+$Ly5.1$^+$ Phf19$^{+/+}$ or Phf19$^{-/-}$ T cells into wild-type mice in conjunction with gp100-VV. Numbers adjacent to outlined areas indicate percentage after gating on live CD8$^+$Ly5.1$^+$ T cells.

Figure 2H:
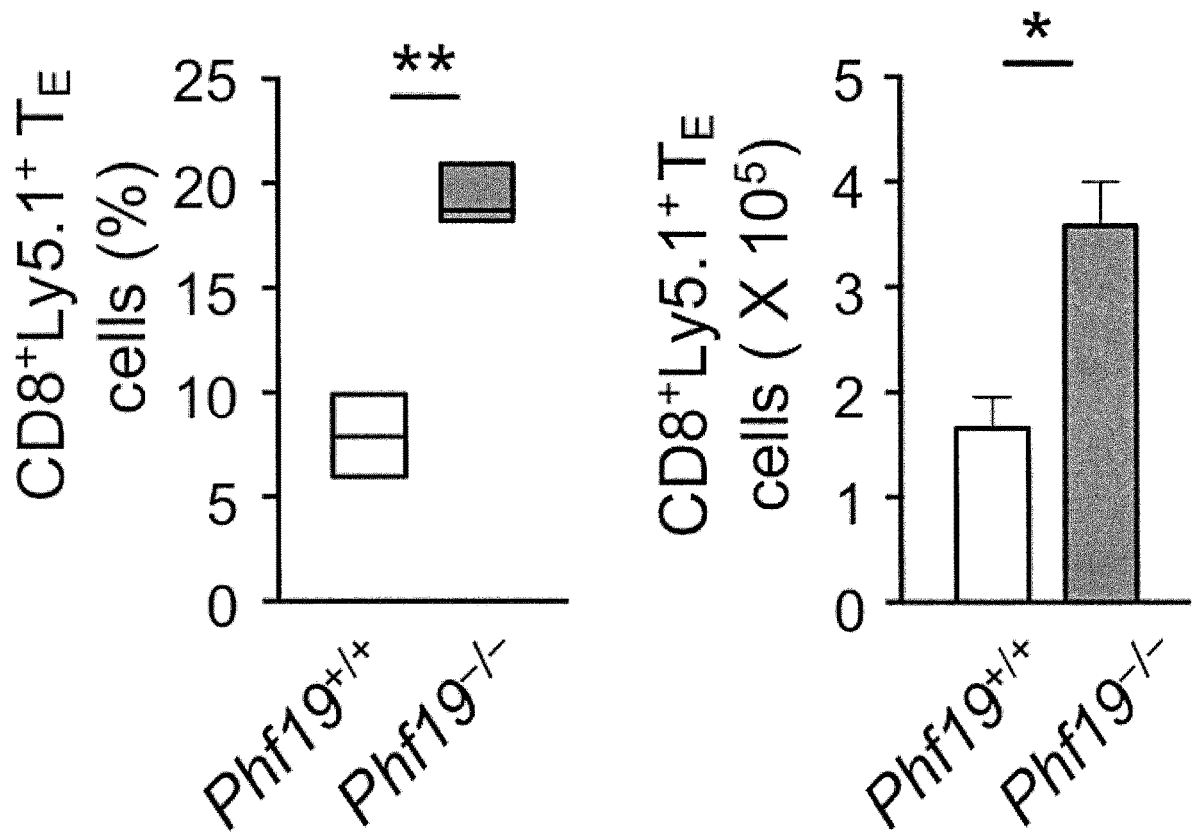

FIG. 2H is a box plot showing percentages (left) and a bar graph showing the number (right) of pmel-1 CD8$^+$Ly5.1$^+$ T$_E$ cells in the spleen 5 days after transfer of $3\times10^5$ naïve pmel-1 CD8$^+$Ly5.1$^+$ Phf19$^{+/+}$ or Phf19$^{-/-}$ T cells into wild-type mice in conjunction with gp100-VV.

Figure 2I:
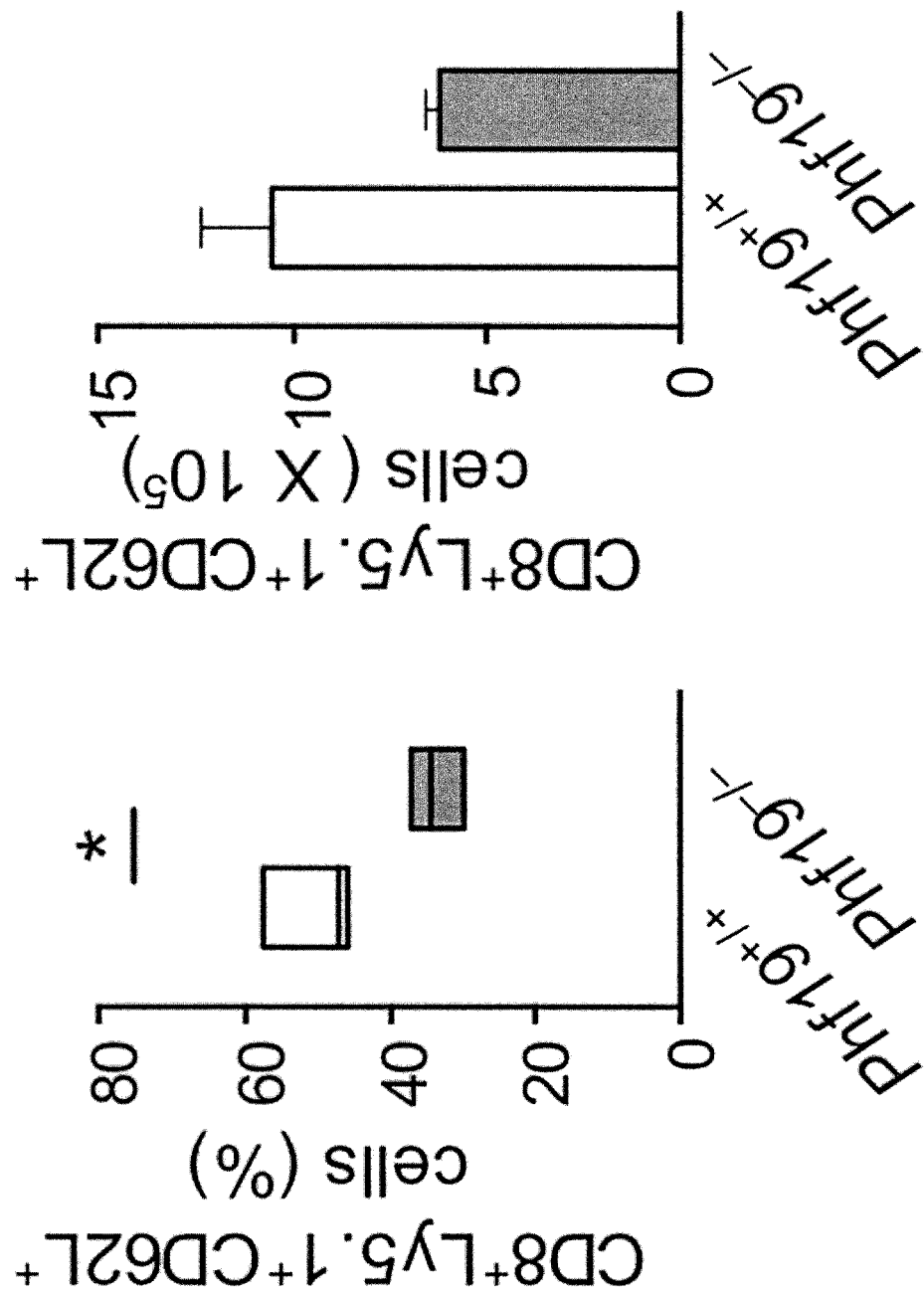

FIG. 2I is a dot plot showing the percentage (left) and a bar graph showing the number (right) of CD8$^+$ Ly5.1$^+$ CD62L$^+$ T cells in the spleen 5 days after transfer of $3\times10^5$ naïve pmel-1 CD8$^+$Ly5.1$^+$ Phf19$^{+/+}$ or Phf19$^{-/-}$ T cells into wild-type mice in conjunction with gp100-VV. Data are presented as box plots extending as a range. Bands inside the boxes represent median values of three mice.

Figures 2J, 2K:
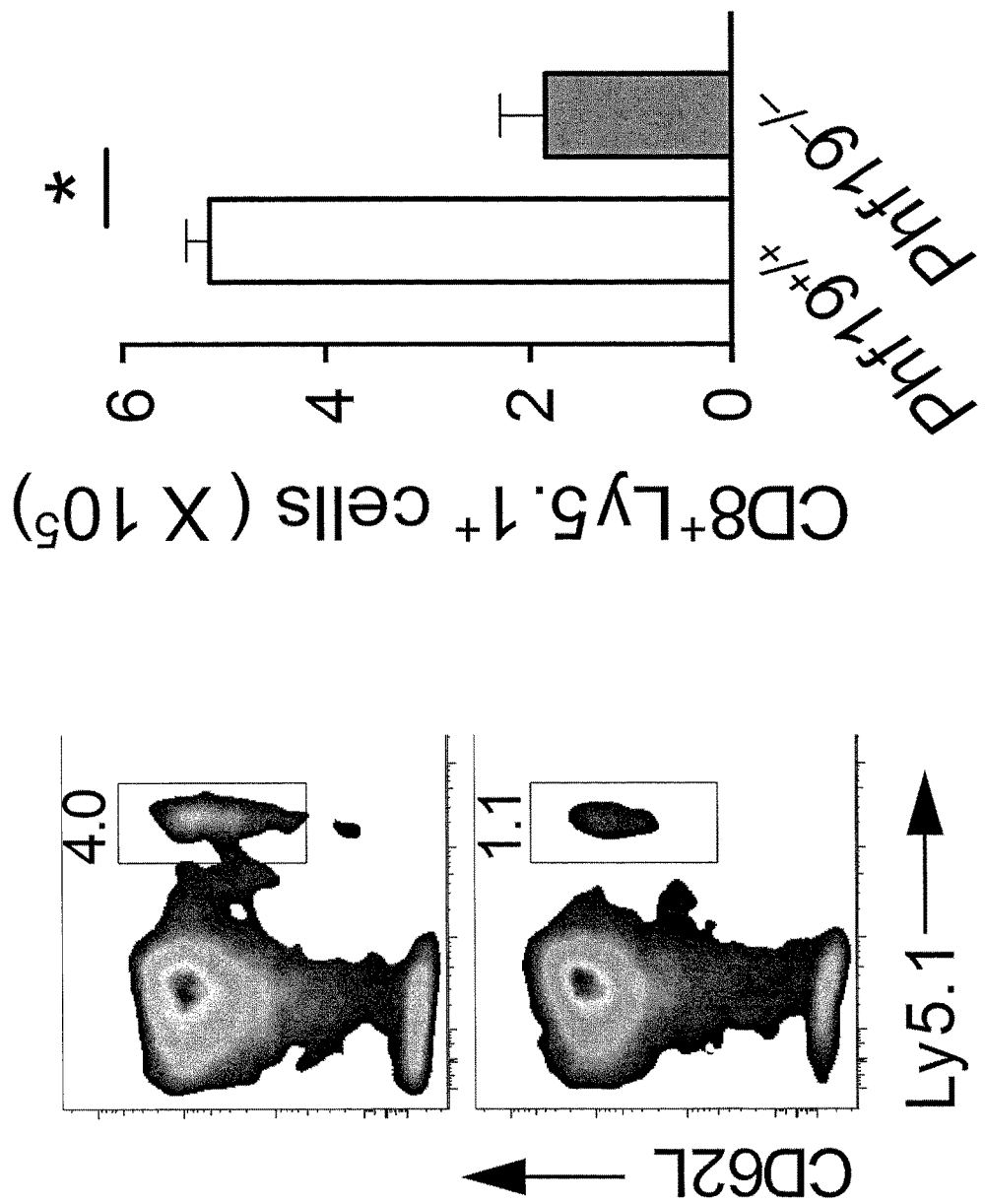

FIG. 2J shows density plots representing flow cytometry of CD8$^+$Ly5.1$^+$ T cells in the spleen 30 days after adoptive transfer of $10^5$ Phf19$^{+/+}$ and Phf1.9$^{-/-}$ naïve pmel-1 CD8$^+$ T cells into wild-type mice in conjunction with gp100-VV. Numbers adjacent to outlined areas indicate percentage after gating on live CD8$^+$ Ly5.1$^+$ T cells. Data are presented as the mean of three to four mice in two independent experiments. *=P<0.05 (unpaired two-tailed Student's t-test).

FIG. 2K is a bar graph showing the number of CD8$^+$ Ly5.1$^+$ T cells in the spleen 30 days after adoptive transfer of $10^5$ Phf1.9$^{+/+}$ and Phf19÷ naïve pmel-1 CD8$^+$ T cells into wild-type mice in conjunction with gp100-VV. Bars represent the mean±s.e.m. of three mice. Data are presented as the mean of three to four mice in two independent experiments. *=P<0.05 (unpaired two-tailed Student's t-test).

Figure 2L:
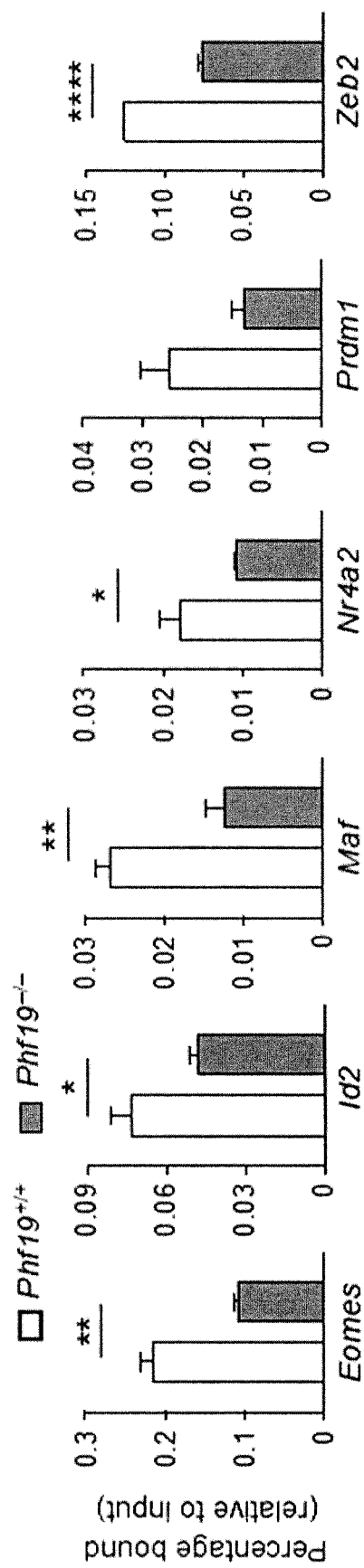

FIG. 2L is a series of bar graphs showing ChIP-qPCR analyses using H3K27me3 antibody on in vitro activated non T$_E$ KLRG1$^-$ Phf19$^{+/+}$ or Phf19$^{-/-}$ T cells with primers specific to the transcription start site of selected TFs. ChIP enrichments are presented as the percentage of protein bound, normalized to input. Bars represent the mean±s.e.m. of technical triplicates. Data are representative of two independent experiments. *=P<0.05; =P<0.01; **=P<0.001 (unpaired two-tailed Student's t-test).

Figure 3B:
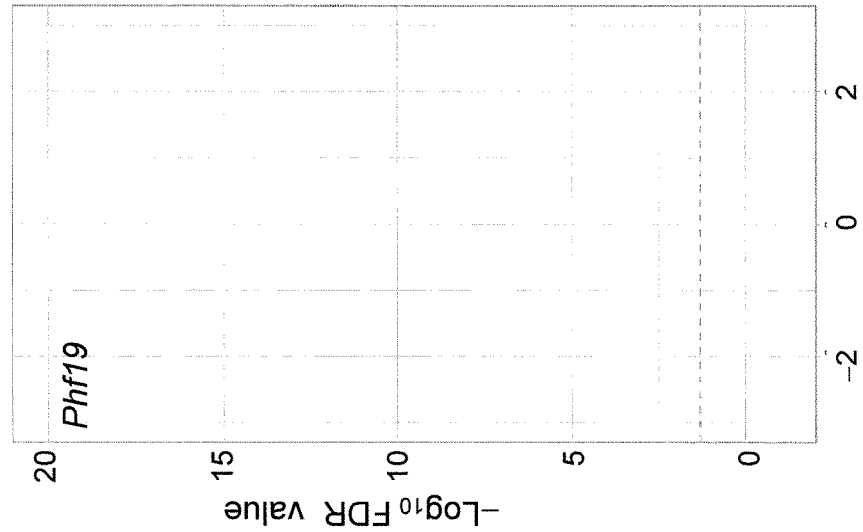
Figure 3A:
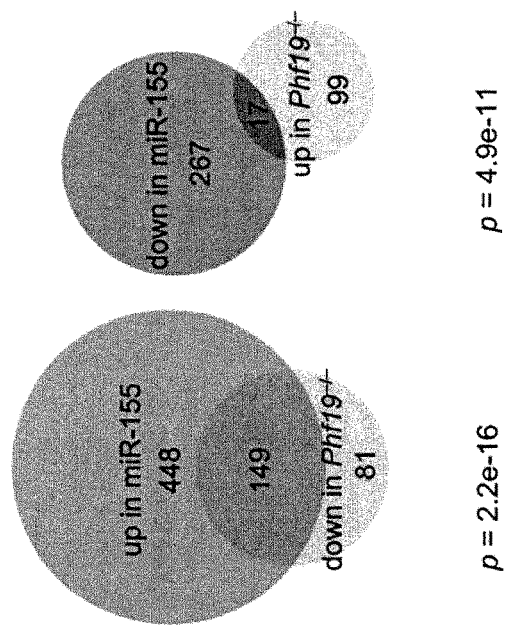

FIG. 3A shows Venn diagrams depicting the number of differentially expressed genes in miR-155-overexpressing and Phf19$^{-/-}$ KLRG1$^-$CD62L$^-$CD8$^+$ T cells 5 days after transfer of $3\times10^5$pmel-1 Phf19$^{+/+}$/Phf19$^{-/-}$ cells or pmel-1 cells overexpressing Ctrl-miR/miR-155 into wild-type mice in conjunction with gp100-VV. RNA-seq data were obtained from triplicated groups of three mice.

FIG. 3B is a volcano plot depicting the number of differentially expressed genes in miR-155-overexpressing and Phf19$^{-/-}$ KLRG1$^-$CD62L$^-$CD8$^+$ T cells 5 days after transfer of $3\times10^5$pmel-1 Phf19$^{+/+}$/Phf19$^{-/-}$ cells or pmel-1 cells overexpressing Ctrl-miR/miR-155 into wild-type mice in conjunction with gp100-VV. RNA-seq data were obtained from triplicated groups of three mice.

Figure 3C:
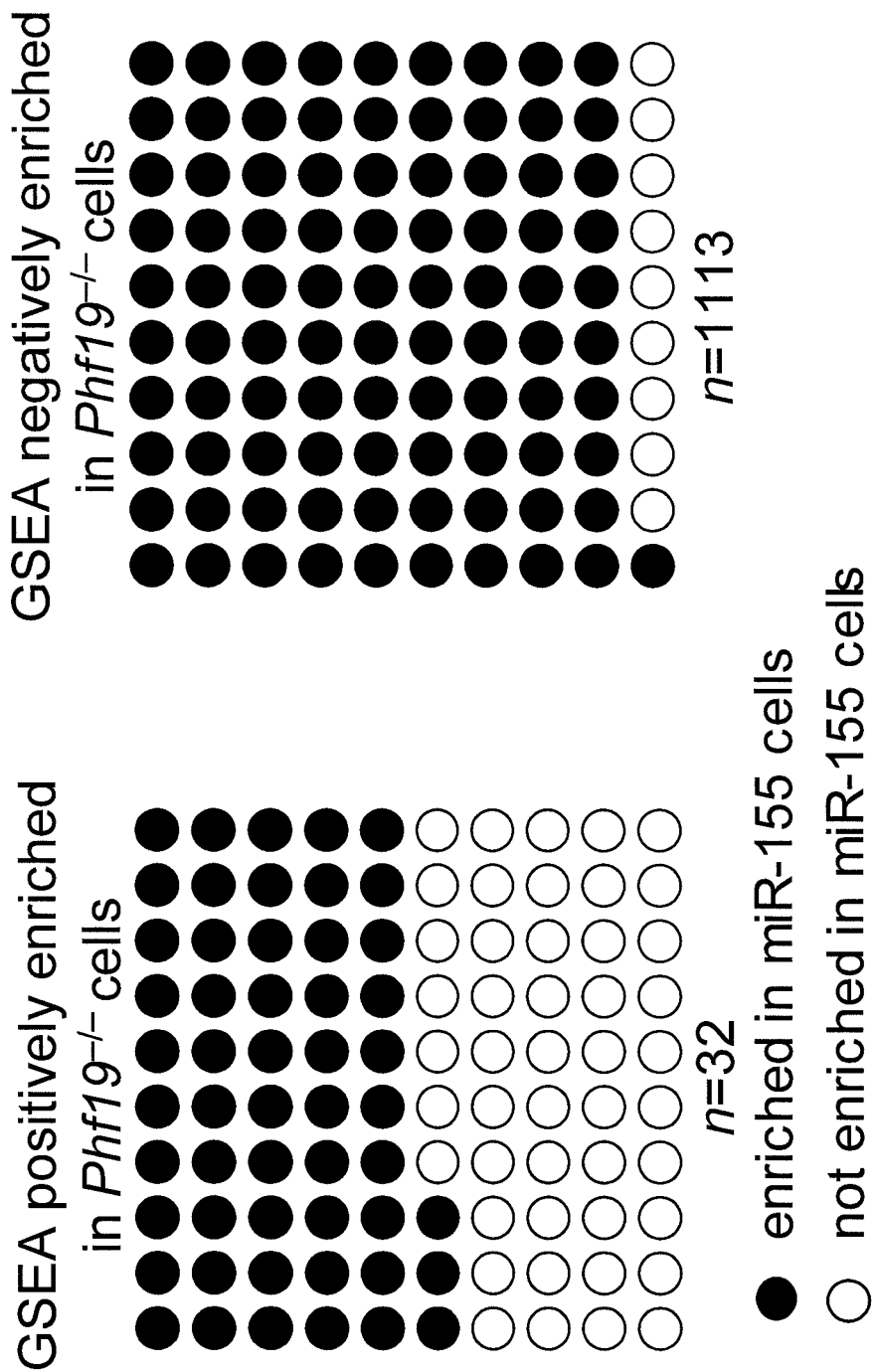

FIG. 3C shows gene sets significantly enriched (FDR<0.25) in Phf19$^{-/-}$ CD8$^+$ T cells. Gene sets also enriched in miR-155 overexpressing cells are highlighted in black.

Figure 3D:
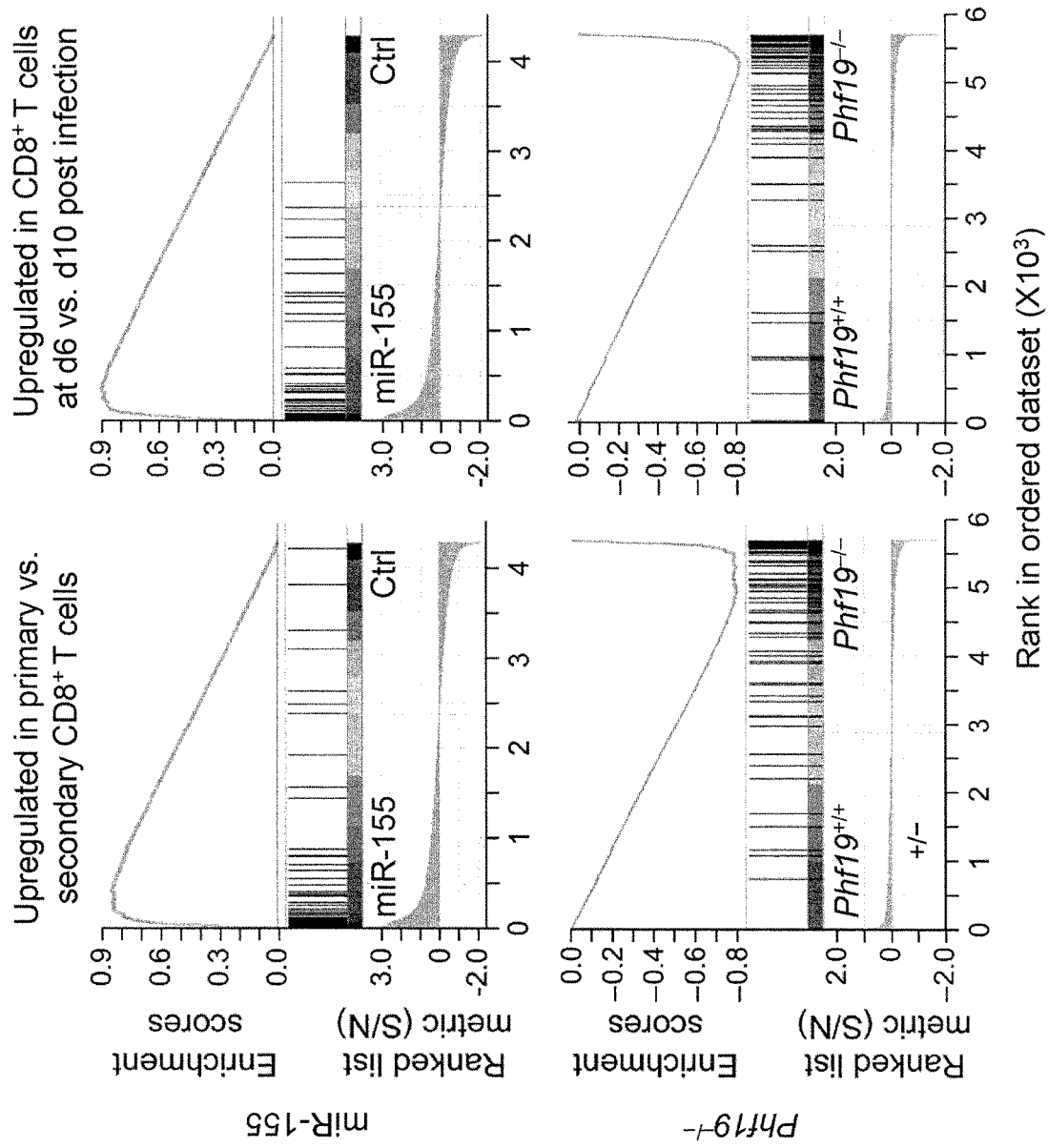

FIG. 3D shows a graphs representing the enrichment of genes upregulated in CD8$^+$ T cells responding to primary vs secondary LCMV infections (left) and enrichment of genes upregulated in CD8$^+$ T cells at d6 vs d10 post LmOVA infections (right) in miR-155-overexpressing and Phf19$^{-/-}$ CD8$^+$ T cells.

Figure 3E:
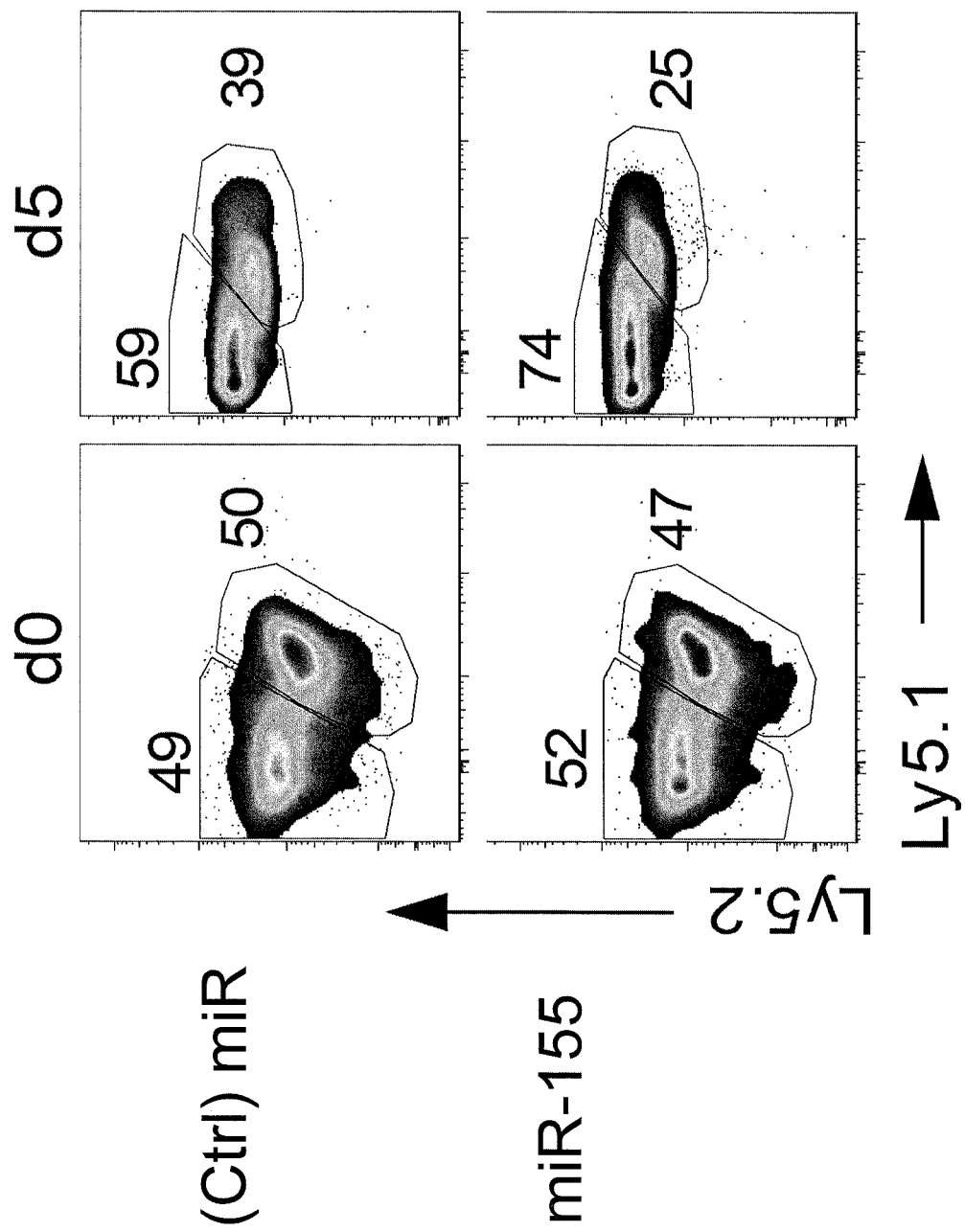

FIG. 3E shows density plots representing flow cytometry of live pmel-1 Phf19$^{+/+}$Ly5.2$^{+/+}$ and pmel-1 Phf19$^{-/-}$ Ly5.1$^{+/-}$ cells transduced with either miR-155 or Ctrl-miR assessed pre-transfer and 5 days after co-transfer of $3\times10^5$ cells into Ly5.1$^{+/+}$ mice in conjunction with gp100-VV. Numbers adjacent to outlined areas indicate percentage after gating on live CD8$^+$GFP$^+$ T cells.

Figures 3F, 3G:
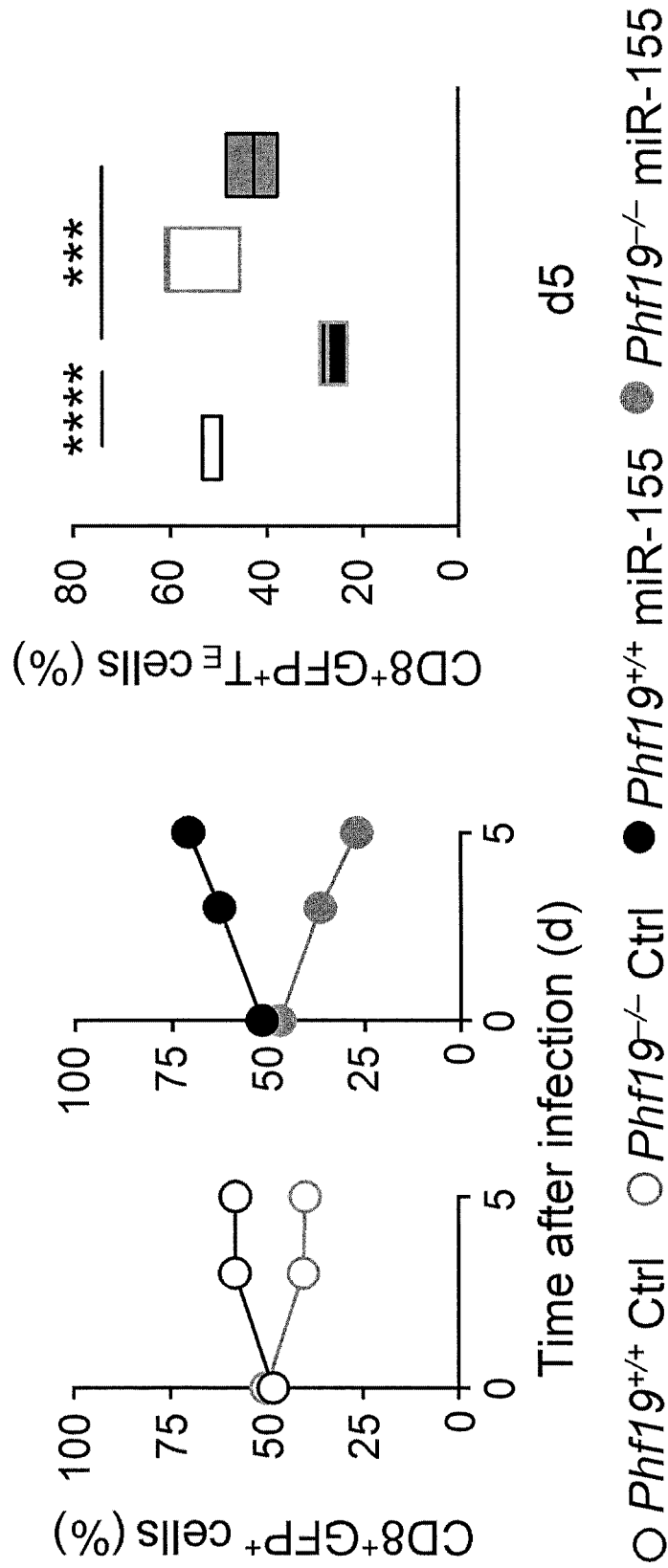

FIG. 3F is a graph showing percentages of live pmel-1 Phf19$^{+/+}$Ly5.2$^{+/+}$ and pmel-1 Phf19$^{-/-}$Ly5.1$^{+/-}$ cells transduced with either miR-155 or Ctrl-miR assessed at indicated time points after co-transfer of $3\times10^5$ cells into Ly5.1$^{+/+}$ mice in conjunction with gp100-VV. Symbols represent the mean±s.e.m. of three mice; small horizontal lines (right panel) indicate the mean±s.e.m. Data are representative of two independent experiments. *=P<0.005; **=P<0.001 (unpaired two-tailed Student's t-test).

FIG. 3G is a box plot showing percentages of live pmel-1 CD8$^+$GFP$^+$ T$_E$ cells at indicated time points after co-transferring of 3×10$^5$ pmel-1 Phf19$^{+/+}$Ly5.2$^{+/+}$ and pmel-1 Phf19$^{-/-}$ Ly5.1$^{+/-}$ cells transduced with either miR-155 or Ctrl-miR into Ly5.1$^{+/+}$ mice in conjunction with gp100-VV Symbols represent the mean±s.e.m. of three mice; small horizontal lines (right panel) indicate the mean±s.e.m. Data are representative of two independent experiments. *=P<0.005; **=P<0.001 (unpaired two-tailed Student's t-test).

Figure 4B:
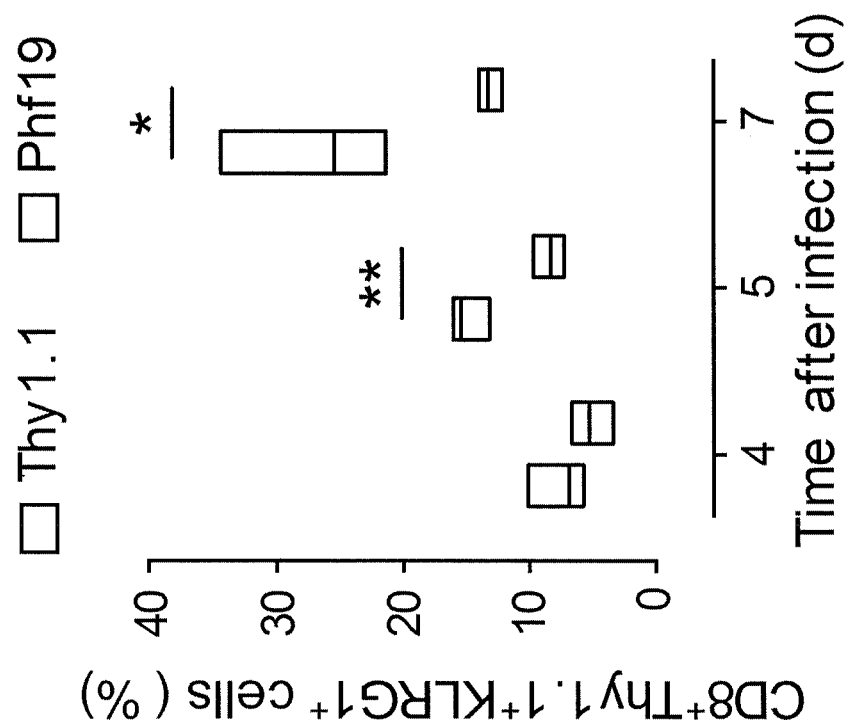
Figure 4A:
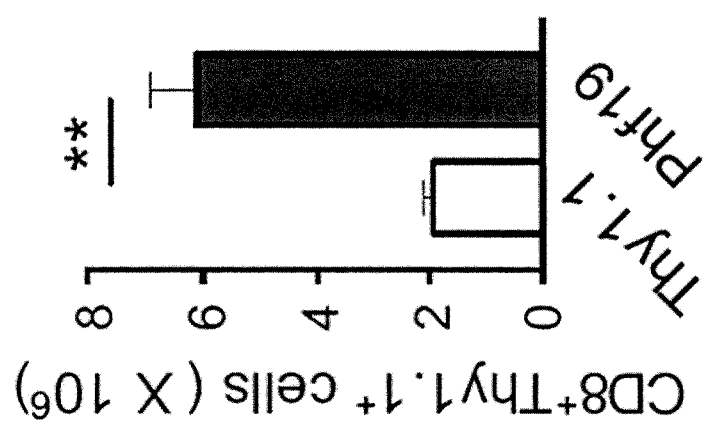

FIG. 4A is a bar graph of the number of pmel-1 CD8$^+$ Thy1.1$^+$ T cells (x 10$^6$) in the spleen following adoptive transfer of 3×10$^5$ Phf19Thy1.1 (Phf19) or Thy1.1 transduced pmel-1 CD8$^+$ T cells after gp100-VV infection. **=P<0.01 (a two-tailed Student t test).

FIG. 4B is a box plot of the percentage of pmel-1 CD8$^+$ Thy1.1$^+$KLRG1$^+$ T cells in the spleen at indicated time points following adoptive transfer of 3×10$^5$ Phf19Thy1.1 (Phf19) or Thy1.1 (Thy1.1) transduced pmel-1 CD8$^+$ T cells after gp100-VV infection. *=P<0.05; **=P<0.01 (an unpaired two-tailed Student's t test).

Figure 4C:
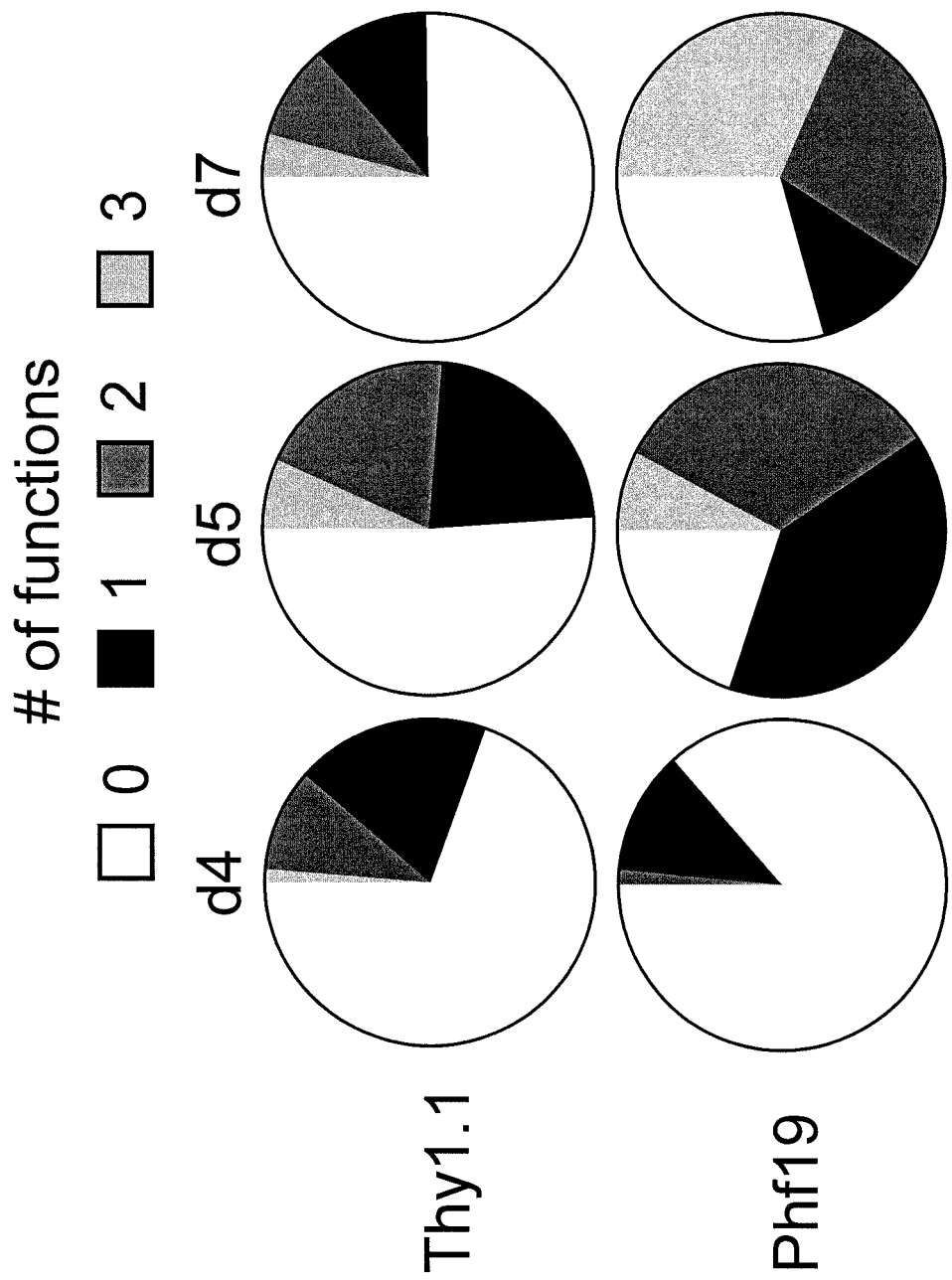

FIG. 4C presents pie charts depicting the quality of the cytokine response in CD8$^+$ Thy1.1$^+$ T cells transduced with the Phf19Thy1.1 (Phf19), or Thy1.1 control. #functions=#cytokines (IFN-γ$^+$, IL-2$^+$, and TNF-α$^+$) produced by the cell.

Figures 4D, 4E:
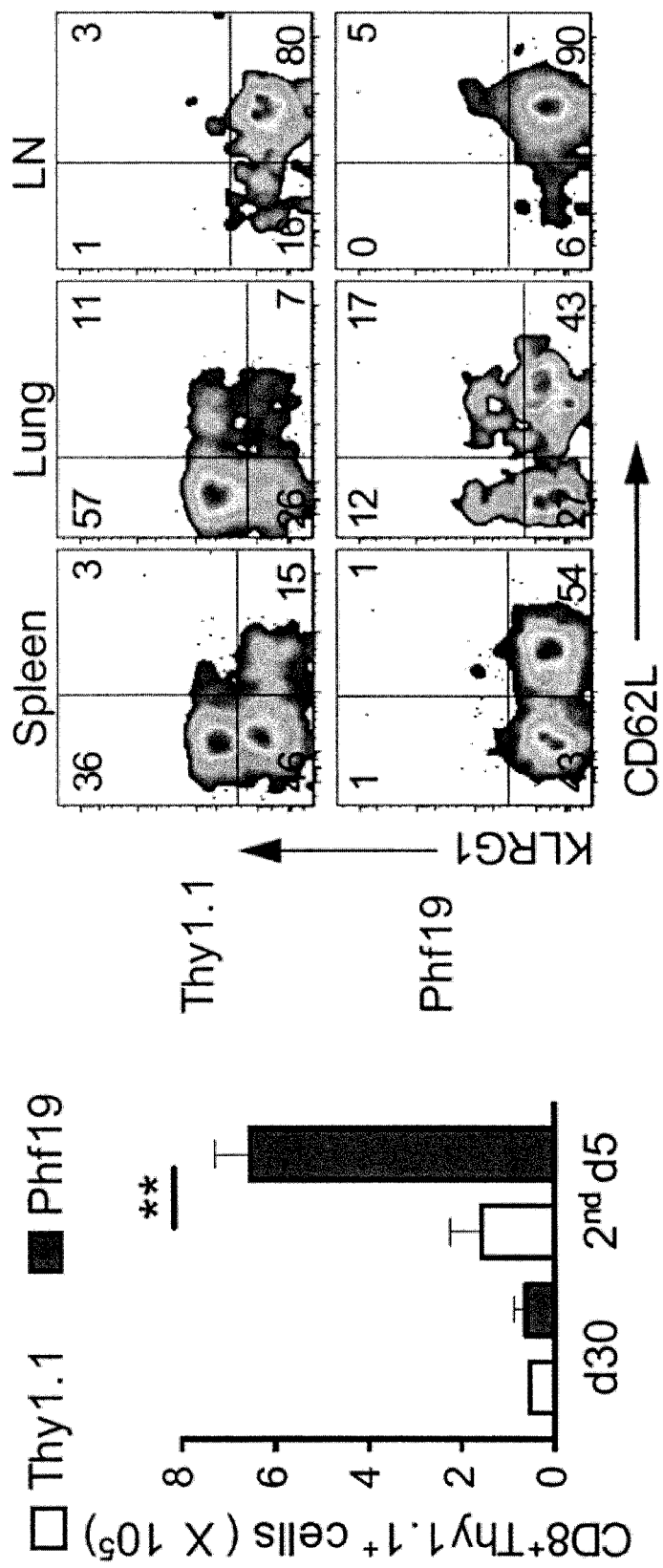

FIG. 4D shows density plots depicting flow cytometry analysis of CD8$^+$Thy1.1$^+$ T cells in the spleen, lung, and lymphoid node 30 days after adoptive transfer of 3×10$^5$ pmel-1 CD8$^+$ T cells overexpressing Phf19Thy1.1 or Thy1.1 into wild-type mice in conjunction with gp100-VV. Numbers adjacent to outlined areas indicate percent after gating on CD8$^+$ Thy1.1$^+$ T cells.

FIG. 4E is a bar graph presenting the number of CD8$^+$ Thy1.1$^+$ cells in the spleen 30 days after transfer and 5 days after re-challenging hosts 30 days post infection as described in 4D. Bars represent the mean±s.e.m. of three individual mice.

Figures 4F, 4G:
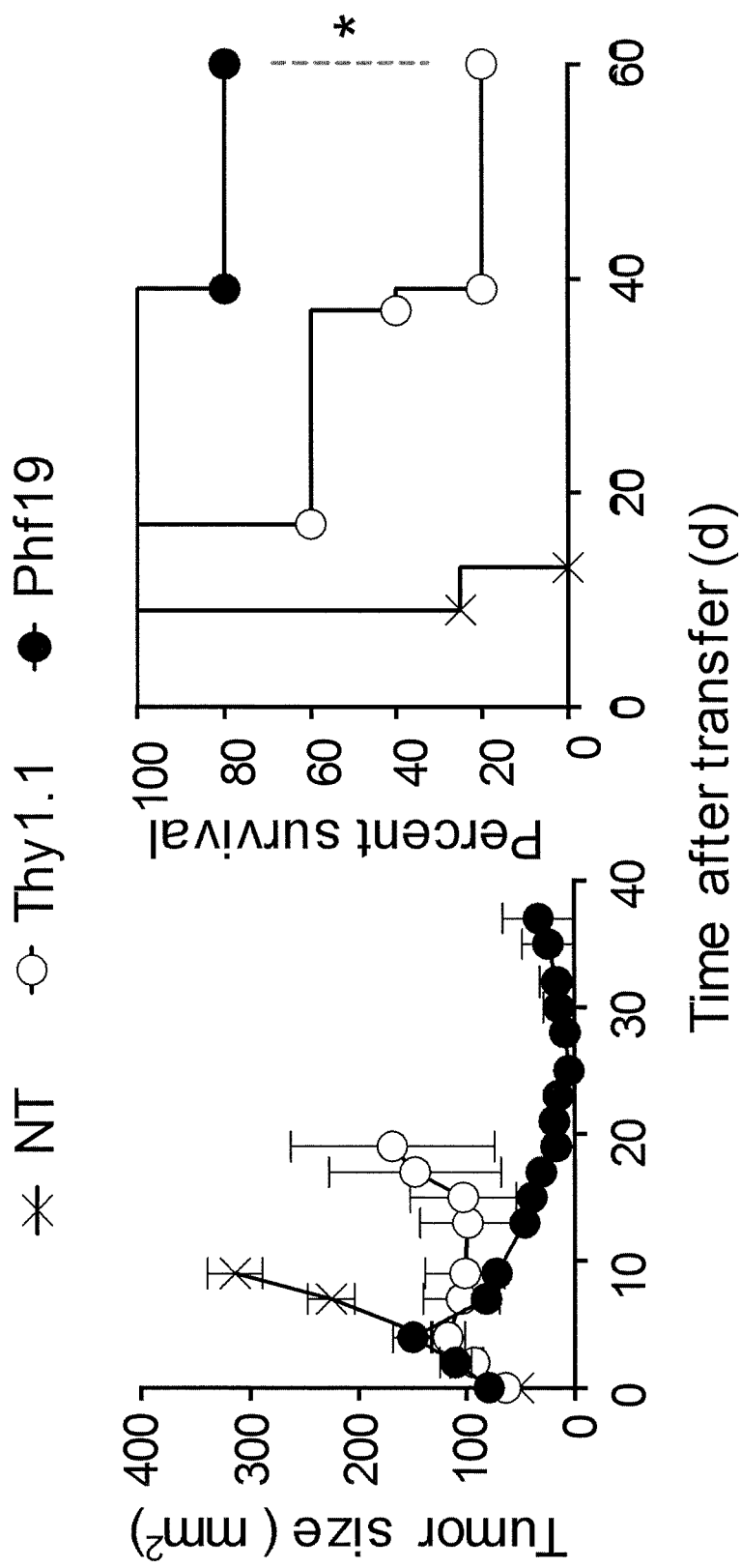

FIG. 4F depicts the tumor size in mm$^2$ of B16 tumor-bearing mice receiving 2×10$^6$ cells Phf19Thy1.1 (Phf19) or Thy1.1 transduced pmel-1 CD8$^+$ T in conjunction with gp100-VV and IL-2. NT=no treatment. *=P<0.05 (a Log-rank (Mantel-Cox) Test).

FIG. 4G depicts the survival curve of B16 tumor-bearing mice receiving 2×10$^6$ cells Phf19Thy1.1 (Phf19) or Thy1.1 transduced pmel-1 CD8$^+$ T in conjunction with gp100-VV and IL-2. NT=no treatment. *=P<0.05 (a Log-rank (Mantel-Cox) Test).

FIG. 5A is an amino acid sequence alignment of the partial aromatic cage of Phf19 indicating the location of the tryptophan (W) and tyrosine (Y) that were mutated to cysteine (C) and alanine (A), respectively, to abrogate chromatin binding of Phf19. The amino acid sequence of the wild-type region of Phf19 is set forth in SEQ ID NO: 7 (Wt), and the amino acid sequence of the mutated Phf19 region is set forth in SEQ ID NO: 8 (Mut).

Figure 5B:
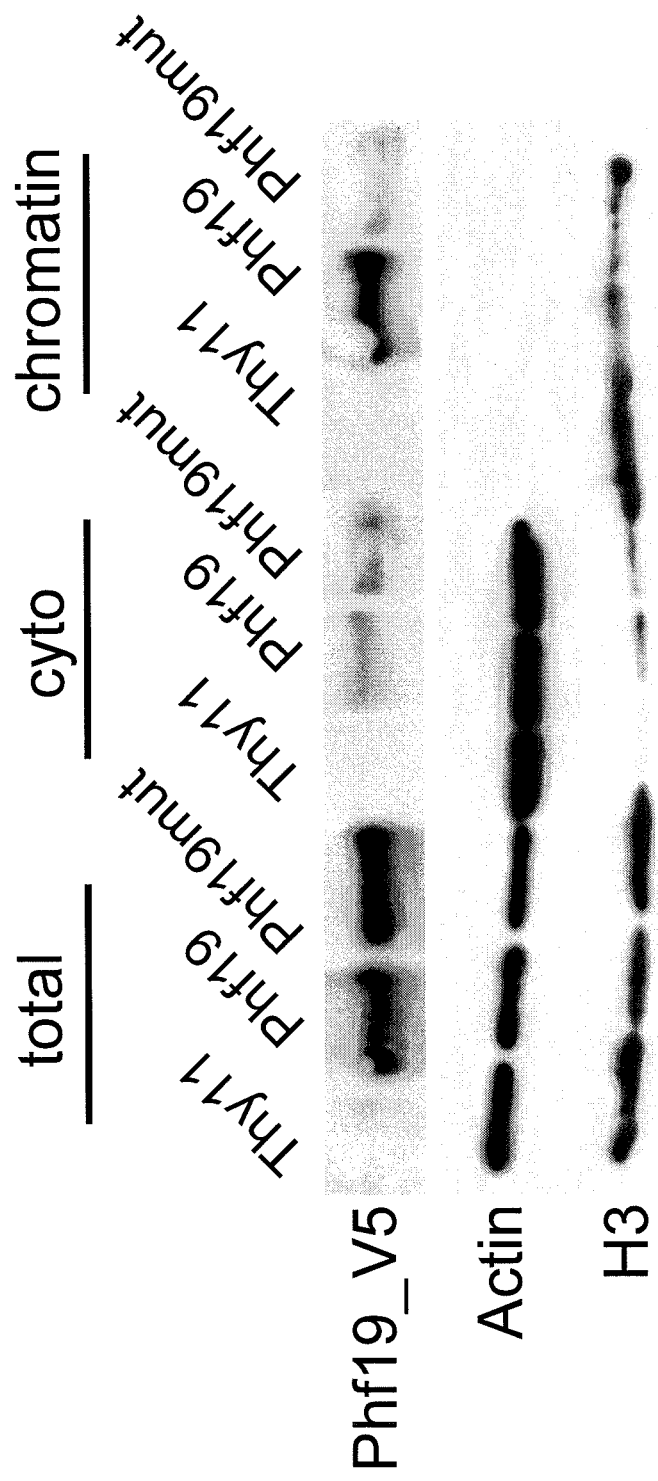

FIG. 5B is an image of a gel depicting an immunoblot of total, soluble, and chromatin-bound proteins from CD8$^+$ T cells transduced with the Phf19Thy1.1, Phf19mutThy1.1, and Thy1.1 control.

Figure 5C:
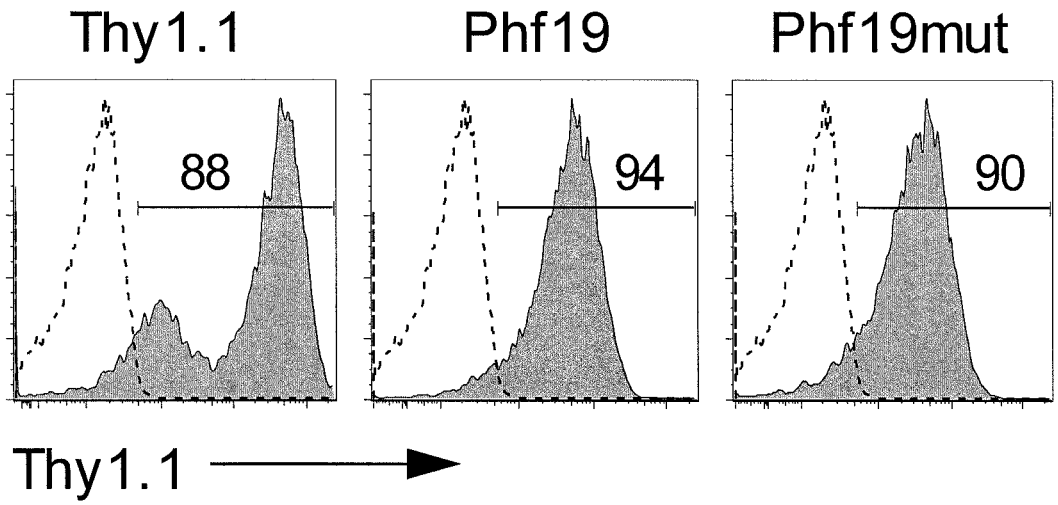

FIG. 5C shows histograms representing flow cytometry of Thy1.1 percentage in CD8$^+$ T cells overexpressing Phf19, Phf19mut, or Thy1.1. Numbers adjacent to outlined areas indicate percentage after gating on CD8$^+$ T cells.

Figure 5D:
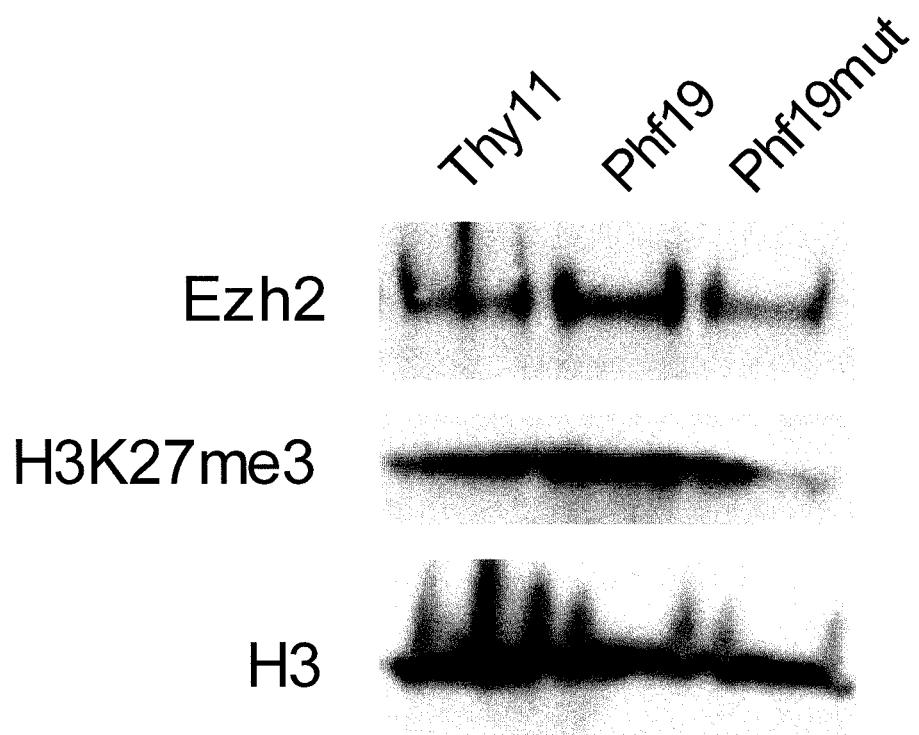

FIG. 5D is an image of a gel depicting an immunoblot of Ezh2, H3K27me3, and H3 levels in chromatin fraction of CD8$^+$ T cells transduced with Phf19, Phf19mut or Thy1.1.

Figures 5E, 5F:
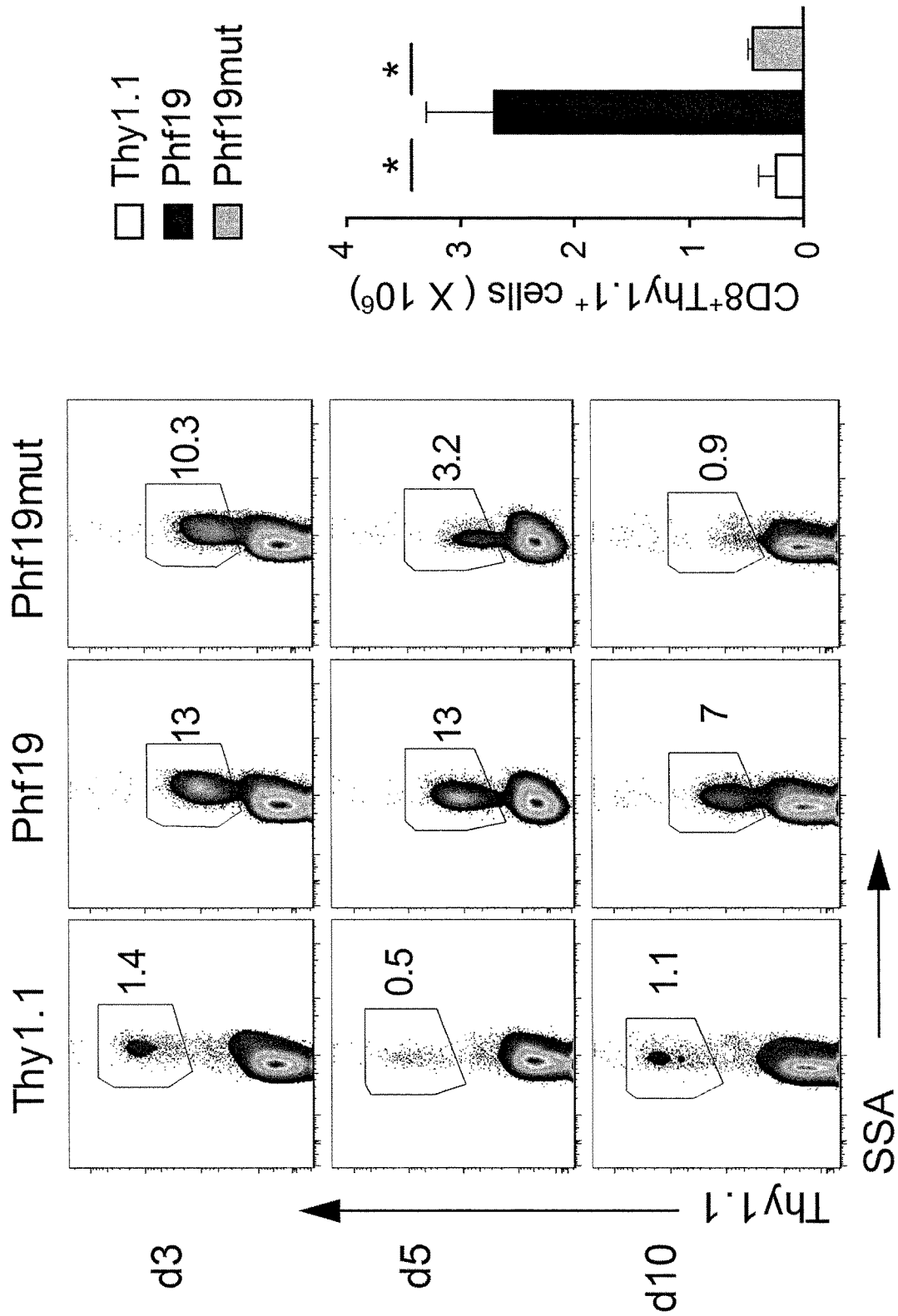

FIG. 5E shows density plots representing flow cytometry of T cells in the spleen following transfer of 3×10$^5$ pmel-1 CD8$^+$ T cells transduced with Phf19Thy1.1, Phf19mutThy1.1, or Thy1.1 into wild-type mice in conjunction with gp100-VV. Numbers adjacent to outlined areas indicate percentage after gating on CD8$^+$GFP$^+$ T cells.

FIG. 5F is a bar graph showing the number of live pmel-1 CD8$^+$ Thy1.1$^+$ T cells in the spleen 5 days following transfer of 3×10$^5$ pmel-1 CD8$^+$ T cells transduced with Phf19Thy1.1, Phf19mutThy1.1, or Thy1.1 into wild-type mice in conjunction with gp100-VV. Bars represent the mean±s.e.m. of three mice. Data are representative of two independent experiments. *=P<0.05; =P<0.01; *=P<0.005; ****=P<0.001 (unpaired two-tailed Student's t-test).

Figures 5G, 5H:
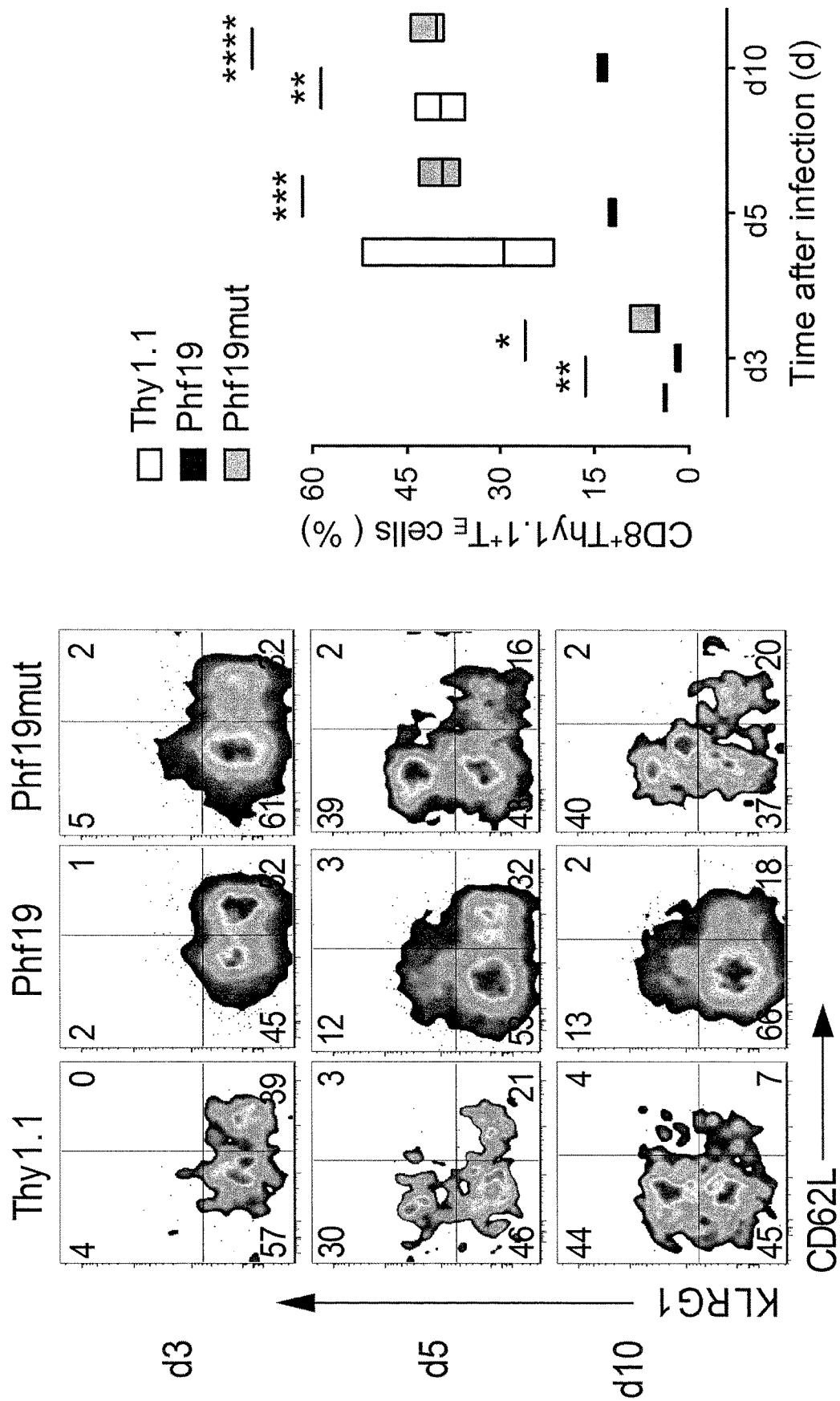

FIG. 5G shows density plots representing flow cytometry of live CD8$^+$ Thy1.1$^+$ T cells in the spleen 5 days following transfer of 3×10$^5$ pmel-1 CD8$^+$ T cells transduced with Phf19Thy1.1, Phf19mutThy1.1, or Thy1.1 into wild-type mice in conjunction with gp100-VV. Numbers adjacent to outlined areas indicate percentage after gating on live CD8$^+$ Thy1.1$^+$ T cells.

FIG. 5H is a box plot representing the percentage of live pmel-1 CD8$^+$ Thy1.1$^+$ T$_E$ cells in the spleen 5 days following transfer of 3×10$^5$ pmel-1 CD8$^+$ T cells transduced with Phf19Thy1.1, Phf19mutThy1.1, or Thy1.1 into wild-type mice in conjunction with gp100-VV. Data are presented as box plots extending as a range. Bands inside the boxes represent median values of three mice.

Figure 5J:
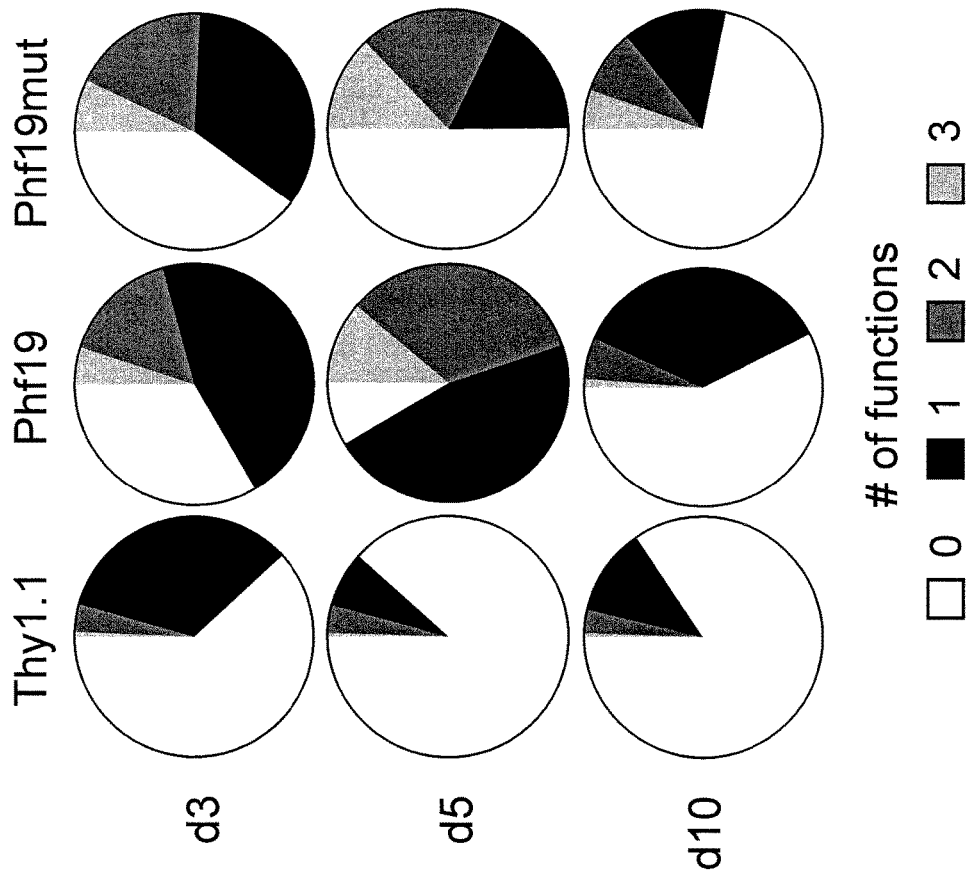
Figure 5I:
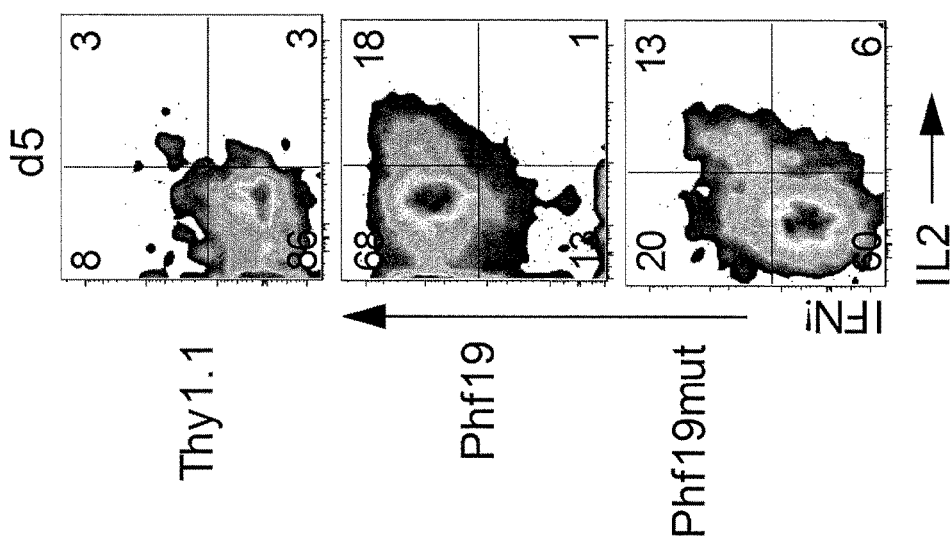

FIG. 5I shows density plots representing flow cytometry of cytokine production of live CD8$^+$ Thy1.1$^+$ T cells in the spleen 5 days after transfer of 3×10$^5$ pmel-1 CD8$^+$ T cells transduced with Phf19Thy1.1, Phf19mutThy1.1, or Thy1.1 into wild-type mice in conjunction with gp100-VV. Numbers adjacent to outlined areas indicate percentage after gating on live CD8$^+$ Thy1.1$^+$ T cells.

FIG. 5J presents pie charts depicting the quality of the cytokine response in live CD8$^+$ Thy1.1$^+$ T cells in the spleen 5 days after transfer of 3×10$^5$ pmel-1 CD8$^+$ T cells transduced with Phf19Thy1.1, Phf19mutThy1.1, or Thy1.1 into wild-type mice in conjunction with gp100-VV, as determined by the Boolean combination of gates identifying IFN-γ$^+$, IL-2+, and TNF-α$^+$ cells. Data are presented as the mean of three mice. Data are representative of two independent experiments. *=P<0.05; =P<0.01; *=P<0.005; ****=P<0.001 (unpaired two-tailed Student's t-test).

FIG. 5K is a box plot showing the percentage of CD8$^+$ Thy1.1±KLRG1$^+$ T cells in the spleen 5 days after re-challenging hosts 30 days following adoptive transfer of 3×10$^5$ Phf19Thy1.1 (Phf19), Phf19mutThy1.1 (Phf19mut), or Thy1.1 (Thy1.1) transduced pmel-1 CD8$^+$ T cells into wild-type mice in conjunction with gp100-VV. **=P<0.01 (a two-tailed Student t test).

FIG. 5L is a box plot showing the percentage of CD8$^+$ Thy1.1$^+$CD62L$^+$ T cells in the spleen 5 days after re-challenging hosts 30 days following adoptive transfer of 3×10$^5$ Phf19Thy1.1 (Phf19), Phf19mutThy1.1 (Phf19mut), or Thy1.1 (Thy1.1) transduced pmel-1 CD8$^+$ T cells into wild-type mice in conjunction with gp100-VV. **=P<0.01 (a two-tailed Student t test).

Figure 5M:
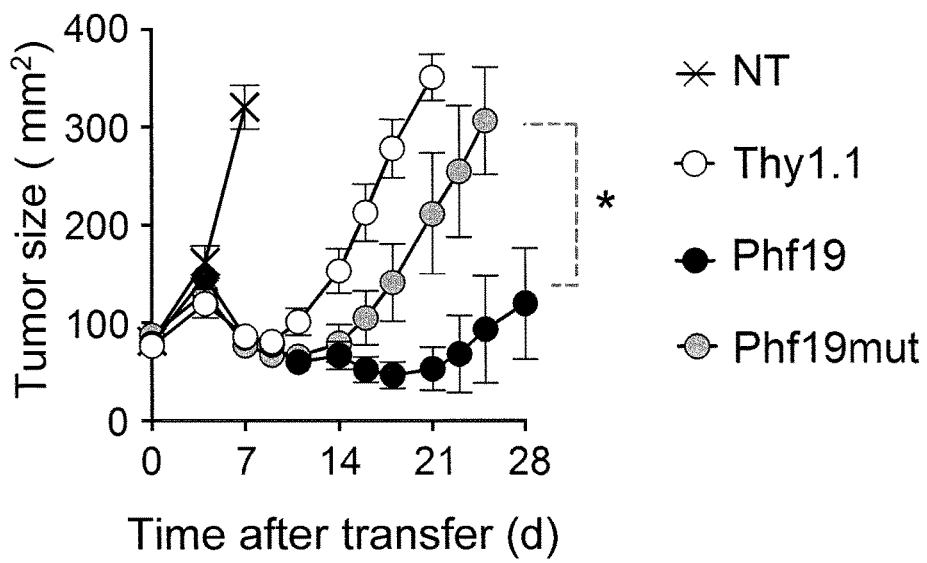

FIG. 5M is a graph showing tumor size (mean±s.e.m.) of B16 tumor-bearing mice receiving 2×10$^6$ pmel-1 CD8$^+$ T cells transduced with Phf19Thy1.1, Phf19mutThy1.1, or Thy1.1 into wild-type mice in conjunction with gp100-VV and IL-2. NT, no treatment (n=7 mice/group). Data are representative of two independent experiments. *=P<0.05; =P<0.01; *=P<0.005; ****=P<0.001 (unpaired two-tailed Student's t-test).

Figure 5N:
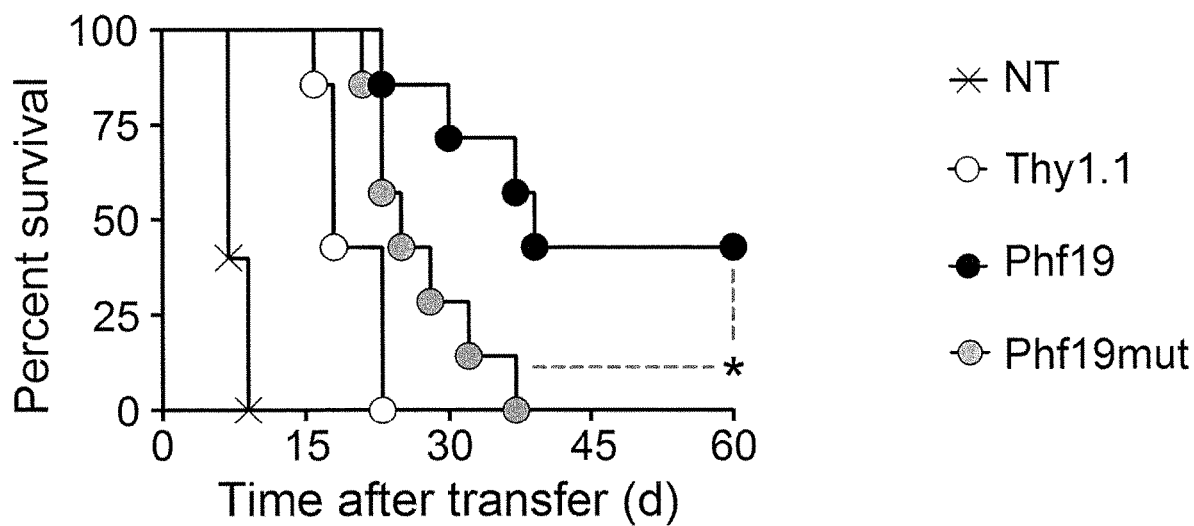

FIG. 5N is a graph showing a survival curve of B16 tumor-bearing mice receiving 2×10$^6$ pmel-1 CD8$^+$ T cells transduced with Phf19Thy1.1, Phf19mutThy1.1, or Thy1.1 into wild-type mice in conjunction with gp100-VV and IL-2. NT, no treatment (n=7 mice/group). Data are representative of two independent experiments. *=P<0.05 (a Log-rank (Mantel-Cox) Test).

Figure 6:
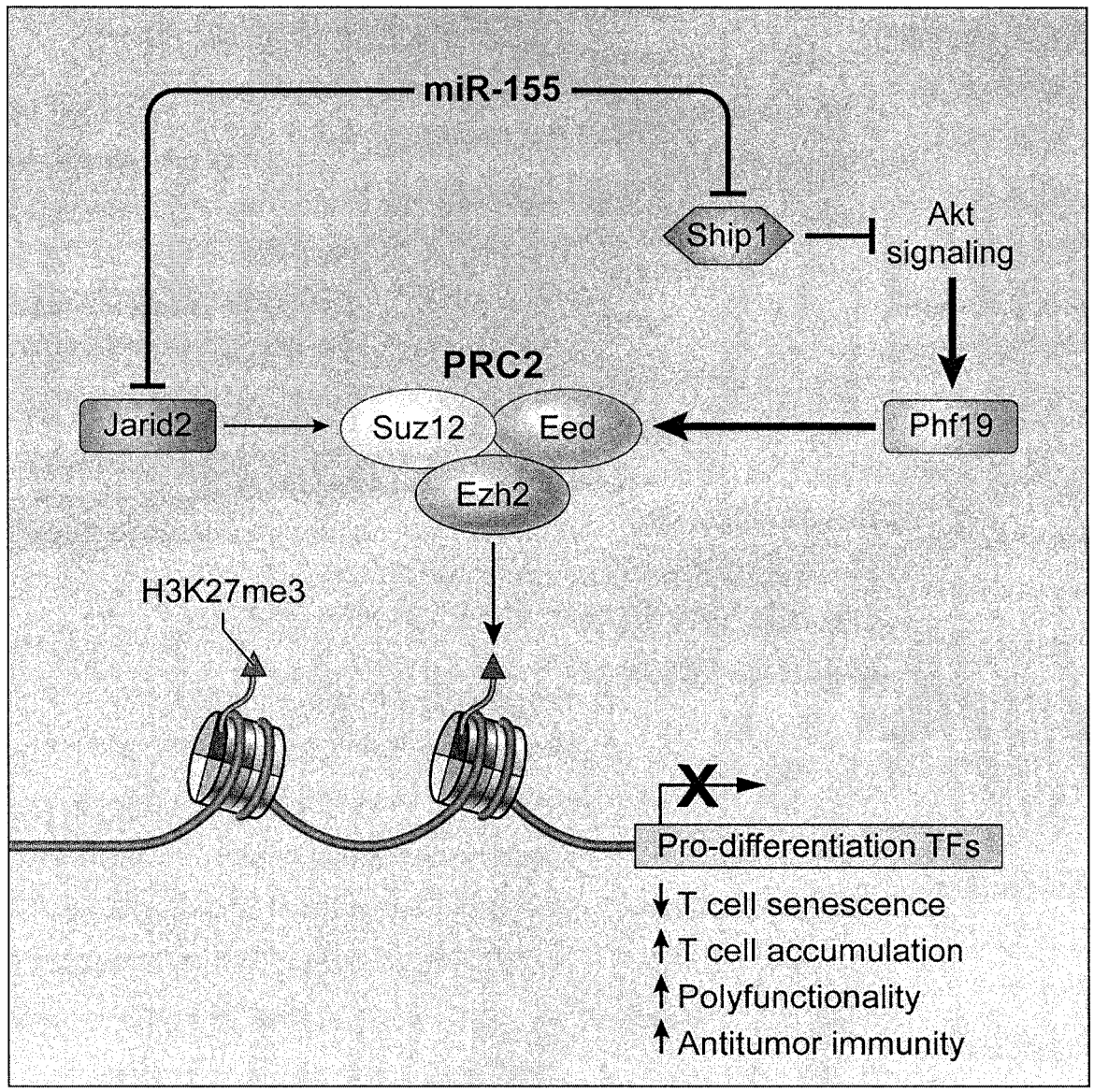

FIG. 6 is a schematic depicting the regulatory circuitry by which miR-155 epigenetically reprograms CD8$^+$ T cell fate and function via enhancement of PRC2 activity. TFs, Transcription factors.

Figure 7:
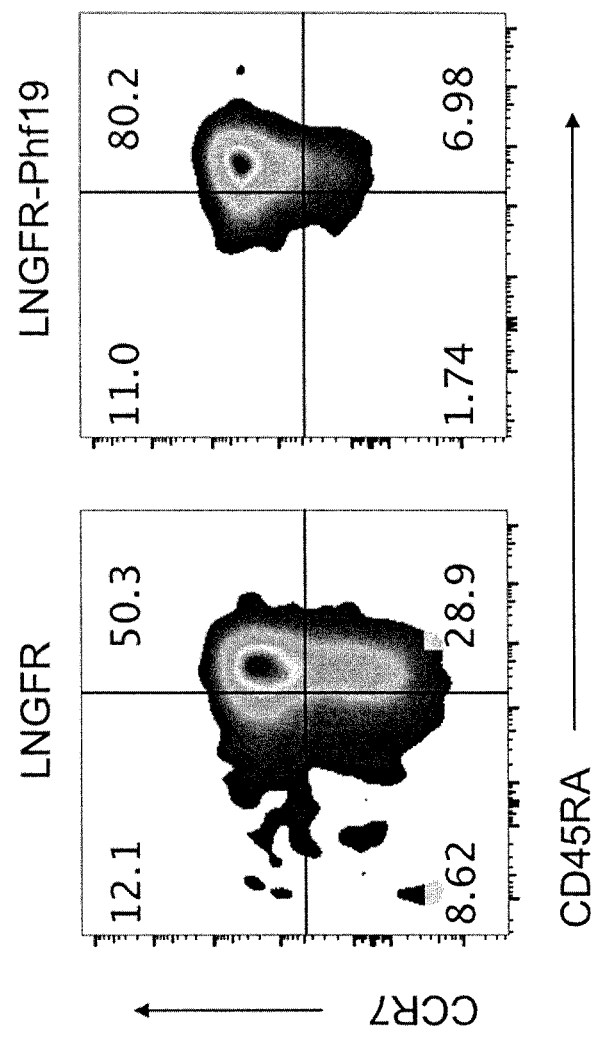

FIG. 7 shows density plots representing flow cytometry of human live CD8$^+$ T cells transduced with Phf19-LNGFR, or LNGFR control and cultured in vitro for 8 days. Numbers adjacent to outlined areas indicate percentage after gating on live CD8$^+$ T cells.

Figure 8:
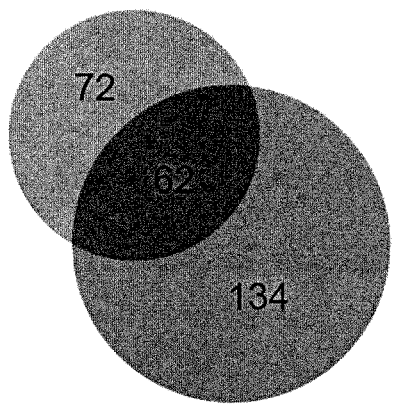

FIG. 8 is a Venn diagram showing a conserved core of genes regulated in mouse and human T cells by Phf19.

Figure 9:
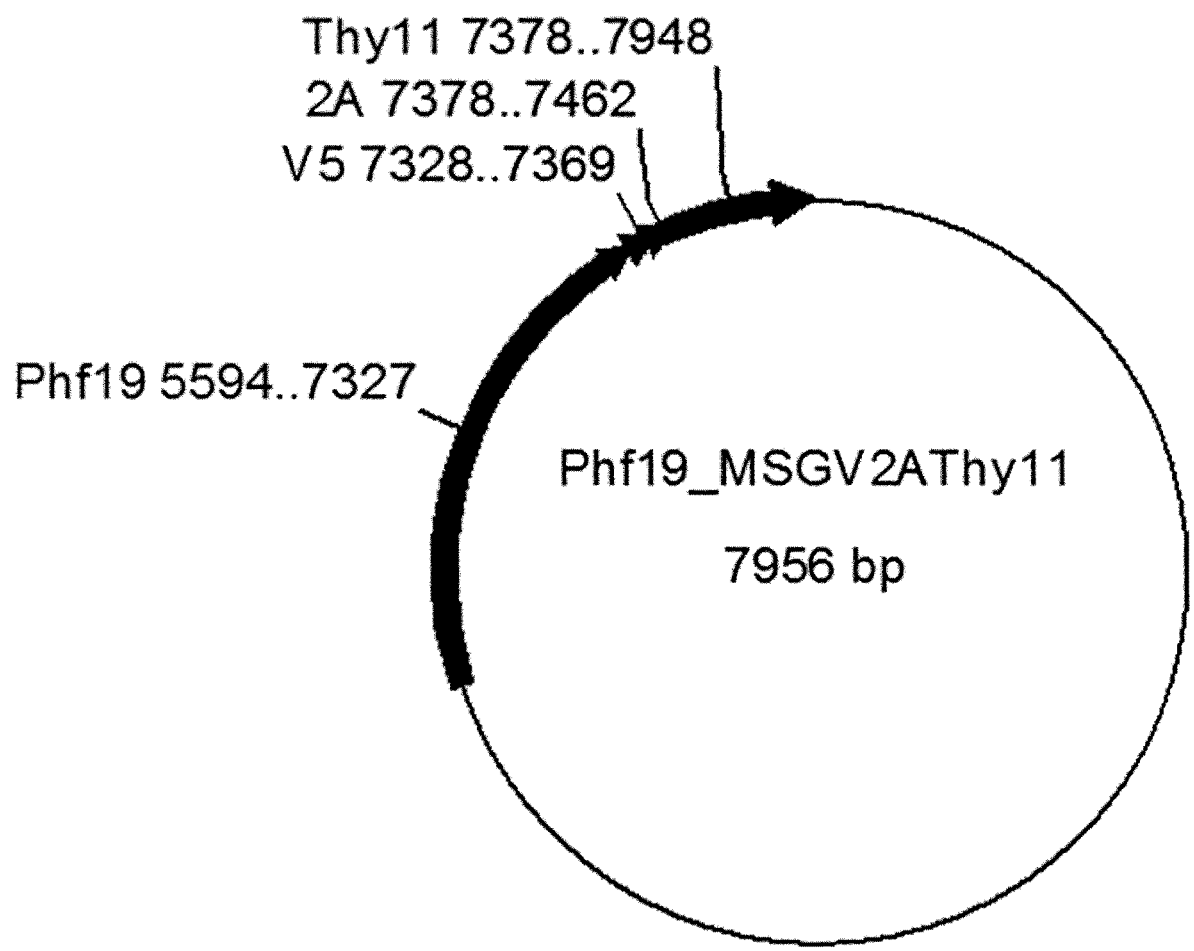

FIG. 9 is a diagram of the vector comprising mouse Phf19Thy1.1.

DETAILED DESCRIPTION OF THE INVENTION

An embodiment of the invention provides a T cell, wherein the T cell has been modified to express Phf19 at a level that is higher than the level of Phf19 expressed by a T cell that has not been modified to express Phf19. The Phf19 used to modify the T cell may be Phf19, functional variants of Phf19, or functional fragments of Phf19. The modified T cell also can be isolated or purified. The modified T cell comprises an antigen-specific receptor, wherein the antigen-specific receptor is a T cell receptor (TCR) or a chimeric antigen receptor (CAR).

The inventive T cells have been modified to overexpress Phf19. In this regard, the modified T cell expresses Phf19 at a level that is higher than the level of Phf19 expressed by a T cell that has not been modified with respect to Phf19 expression (e.g., wild-type T cells). For example, if the T cell has been modified to comprise a vector encoding Phf19, the modified T cell including such vector expresses Phf19 at a level that is higher than the level of Phf19 expressed by a control T cell that does not contain such vector.

The level of expression of Phf19 may be determined using any methods known in the art. For example, the expression level of Phf19 may be determined using quantitative RT-PCR. The level of Phf19 expression may also be determined using antibodies. Antibodies that recognize Phf19 are available from several vendors including Abcam (Cambridge, UK), Cell Signaling Technologies (Danvers, MA), Bethyl Laboratories (Montgomery, TX), among others.

The inventive T cells may provide many advantages, for example, an increase of any one or more of in vivo proliferation, survival, persistence, anti-tumor activity, and anti-viral activity as compared to T cells that have not been modified to overexpress Phf19 (e.g., T cells that lack a vector encoding Phf19, as described in more detail below). CD8$^+$ T cells overexpressing Phf19 present augmented cell expansion, reduced effector senescence, increased polyfunctionality, and superior anti-tumor responses. Also, while not wishing to be bound by theory, Example 4, below suggests that such effects may be influenced by the chromatin-binding capacity of Phf19 via two key amino acids located in the Aromatic cage within its Tudor domain. This suggests that the ability of Phf19 to bind to chromatin and recruit the PRC2 complex to the specific targets for H3K27me3 deposition may be implicated in its role in regulating CD8$^+$ T cell differentiation and functional exhaustion. These findings support a conclusion that T-cell based immunotherapy can be enhanced through epigenetic reprogramming of T cell fate.

The T cell may be isolated or purified. The term "isolated," as used herein, means having been removed from its natural environment. An "isolated" cell, therefore, can be a cell "in vitro" or "ex vivo," even if in the presence of other cells or derivative products of an organism (e.g., serum, growth factors, etc.). The term "purified," as used herein, means being separated from at least some other natural components. A "purified" T cell refers to a T cell which has been separated from at least some other natural components, such as tissues, cells, proteins, nucleic acids, etc. Preferably, the inventive T cells are in vitro or ex vivo.

The T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, thymus, spleen, tumor, or other tissues or fluids. The T cells can also be enriched or purified. Methods for enriching or purifying T cells are well known in the art and include, for example, immunomagnetic selection, centrifugation and resuspension, column separation, and immunoprecipitation. CD8$^+$ T cells may be purified from peripheral blood mononuclear cells (PBMCs) by incubating the PBMCs with antibodies against CD4 T cells, B cells, NK cells, dendritic cells, monocytes, granulocytes, and erythrocytes, and subsequently running the mixture through a magnetic column. Cells labeled with the antibodies will be bound to the column, while unlabeled cells, the CD8$^+$ T cells, will elute through.

Preferably, the T cell is a human T cell. The T cell can be any type of T cell and can be of any developmental stage, including but not limited to, CD4$^+$/CD8$^+$ double positive T cells, CD4$^+$ helper T cells, e.g., Th1, Th2, Th9, Th17, Th22 cells, CD4$^+$ T cells, CD8$^+$ T cells (e.g., cytotoxic T cells), peripheral blood mononuclear cells (PBMCs), peripheral blood leukocytes (PBLs), tumor infiltrating cells (TILs), memory T cells, naïve T cells, and the like. Preferably, the cell is a CD8$^+$ T cell.

An embodiment of the invention provides a pharmaceutical composition comprising at least one or two T cells as described herein—i.e., being modified to express Phf19 at a level that is higher than the level of Phf19 expressed by a T cell that has not been modified to express Phf19 and/or comprising a genetic expression vector comprising (a) virally-, bacterially-, or both virally- and bacterially-derived genetic sequences and (b) a genetic sequence encoding Phf19, whereby the genetic sequence encoding Phf19 within the vector is expressed within the T cell(s). Such pharmaceutical composition also comprises a pharmaceutically-acceptable carrier.

The inventive compositions can comprise a single T cell or a population thereof. The population of T cells can be a heterogeneous population comprising the T cell that has been modified to overexpress Phf19 (e.g., a T cell comprising a vector encoding Phf19, as described in more detail below), in addition to at least one other cell, e.g., a T cell, which has not been modified to overexpress Phf19 (e.g., a T cell lacking such a vector encoding Phf19, as described in more detail below), or a cell other than a T cell, e.g., a B cell, a macrophage, a neutrophil, an erythrocyte, a melanocyte, a hepatocyte, an endothelial cell, an epithelial cell, a muscle cell, a brain cell, etc. Alternatively, the population of cells can be a substantially homogeneous population, in which the population mainly comprises T cells that have been modified to overexpress Phf19 and/or comprise the genetic expression vector comprising (a) virally-, bacterially-, or both virally- and bacterially-derived genetic sequences and (b) a genetic sequence encoding Phf19, as described herein. The population also can be a clonal population of T cells, in which all T cells of the population are clones of a single T cell that has been modified to overexpress Phf19.

A T cell of the invention can be present in a population of cells or a composition in an amount of about 10% or more, e.g., about 30% or more, about 50% or more, about 60% or more, about 70% or more, about 75% or more, about 80% or more, about 85% or more, or about 90% or more, based on the total number of cells in the population or composition. Alternatively, or in addition, the T cell of the invention can be present in a population of cells or a composition in an amount of about 95% or less, e.g., about 90% or less, about 85% or less, about 80% or less, about 75% or less, about 70% or less, about 60% or less, about 40% or less, or about 30% or less based on the total number of cells in the population or composition. Thus, the T cell of the invention can be present in a population of cells or a composition in an amount bounded by any two of the above endpoints. For example, the T cell of the invention can be present in a population of cells or a composition in an amount of about 30 to about 60%, about 50 to about 90%, about 60 to about 80%, about 80 to about 90%, or about 75 to about 85%.

An embodiment of the invention provides a method for treating cancer or chronic viral disease in a mammal. The method comprises administering to the mammal an effective amount of the T cell of an embodiment of the invention.

In an embodiment of the invention, the T cell comprises an antigen-specific receptor. The phrases "antigen-specific" and "antigenic specificity," as used herein, mean that the receptor can specifically bind to and immunologically recognize an antigen, or an epitope thereof, such that binding of the receptor to antigen, or the epitope thereof, elicits an immune response. In an embodiment of the invention, the antigen-specific receptor is a T cell receptor (TCR). The antigen-specific TCR generally comprises two polypeptides (i.e., polypeptide chains), such as an α-chain of a TCR, a β-chain of a TCR, a γ-chain of a TCR, a δ-chain of a TCR, or a combination thereof. Such polypeptide chains of TCRs are known in the art. The antigen-specific receptor can comprise any amino acid sequence, provided that the receptor can specifically bind to and immunologically recognize an antigen, such as a disease-associated antigen or epitope thereof.

The antigen-specific receptor can be an endogenous TCR, i.e., the antigen-specific TCR that is endogenous or native to (naturally-occurring on) the T cell. In such a case, the T cell comprising the endogenous TCR can be a T cell that has been isolated from a mammal which is known to express the particular disease-specific antigen. In certain embodiments, the T cell is a primary T cell isolated from a host afflicted with a cancer. In some embodiments, the T cell is a tumor infiltrating lymphocyte (TIL) or a peripheral blood lymphocyte (PBL) isolated from a human cancer patient.

In some embodiments, the mammal from which a T cell is isolated is immunized with an antigen of, or specific for, a disease. Desirably, the mammal is immunized prior to obtaining the T cell from the mammal. In this way, the isolated T cells can include T cells induced to have specificity for the disease to be treated, or can include a higher proportion of cells specific for the disease.

Alternatively, a T cell comprising an endogenous antigen-specific TCR can be a T cell within a mixed population of cells isolated from a mammal, and the mixed population can be exposed to the antigen which is recognized by the endogenous TCR while being cultured in vitro. In this manner, the T cell comprising the TCR that recognizes the disease-specific antigen, expands or proliferates in vitro, thereby increasing the number of T cells having the endogenous antigen-specific receptor.

The antigen-specific TCR can be an exogenous TCR, i.e., an antigen-specific TCR that is not native to (not naturally-occurring on) the T cell. A recombinant TCR is a TCR which has been generated through recombinant expression of one or more exogenous TCR α-, β-, γ-, and/or δ-chain encoding genes. A recombinant TCR can comprise polypeptide chains derived entirely from a single mammalian species, or the antigen-specific TCR can be a chimeric or hybrid TCR comprised of amino acid sequences derived from TCRs from two different mammalian species. For example, the antigen-specific TCR can comprise a variable region derived from a murine TCR, and a constant region of a human TCR such that the TCR is "humanized." Methods of making recombinant TCRs are known in the art. See, for example, U.S. Pat. Nos. 7,820,174, 8,785,601, 8,216,565, and 9,345,748 (each of which is incorporated herein in its entirety by reference).

A T cell of the invention comprising an endogenous antigen-specific TCR can also be transformed, e.g., transduced or transfected, with one or more nucleic acids encoding an exogenous (e.g., recombinant) TCR or other recombinant chimeric receptor. Such exogenous chimeric receptors, e.g., chimeric TCRs, can confer specificity for additional antigens to the transformed T cell beyond the antigens for which the endogenous TCR is naturally specific. This can, but need not, result in the production of T cell having dual antigen specificities.

In an embodiment of the invention, the antigen-specific receptor is a "chimeric antigen receptor" (CAR). Typically, a CAR comprises the antigen binding domain of an antibody, e.g., a single-chain variable fragment (scFv), fused to the transmembrane and intracellular domains of a TCR. Thus, the antigenic specificity of a TCR of the invention can be encoded by a scFv which specifically binds to the antigen, or an epitope thereof. Methods of making such chimeric TCRs are known in the art. See, for example, U.S. Pat. Nos. 8,465,743 and 9,266,960 and U.S. Patent Application Publication No. 2014/0274909 (each of which is incorporated herein in its entirety by reference).

Any suitable nucleic acid encoding a CAR, TCR, or TCR-like protein or polypeptide can be used. In these embodiments, transformation with a nucleic acid encoding Phf19, as discussed below, can occur before, after, or simultaneously with, antigen-specific receptor transformation. The antigen-specific receptor encoded by the transformed nucleic acids can be of any suitable form including for example, a single-chain TCR or a fusion with other proteins or polypeptides (e.g., without limitation co-stimulatory molecules).

The antigen which is specifically recognized by the antigen-specific receptor can be any antigen which is characteristic of a disease. For example, the antigen may be, but is not limited to, a cancer antigen (also termed a tumor antigen or a tumor associated antigen) or a foreign antigen (viral, bacterial, parasite antigens). Foreign antigens are known in the art and include, for example, any viral protein, e.g., env, gag, pol, gp120, thymidine kinase, and the like.

The term "cancer antigen," as used herein, refers to any molecule (e.g., protein, polypeptide, peptide, lipid, carbohydrate, etc.) solely or predominantly expressed or overexpressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, whether or not normally found in an adult host. Cancer antigens are known in the art and include, for instance, mesothelin, CD19, CD22, CD276 (B7H3), gp100, MART-1, Epidermal Growth Factor Receptor Variant III (EGFRVIII), TRP-1, TRP-2, tyrosinase, NY-ESO-1 (also known as CAG-3), MAGE-1, MAGE-3, etc.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells.

The disease which is associated with or is characterized by the antigen recognized by the antigen-specific receptor can be any disease. For instance, the disease can be a cancer or a viral disease, as discussed herein.

The cancer may be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, HPV carcinoma, hypopharynx cancer, kidney cancer, larynx cancer, leukemia, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

For purposes herein, "viral disease" means a disease that can be transmitted from person to person or from organism to organism, and is caused by a virus. In an embodiment of the invention, the viral disease is caused by a virus selected from the group consisting of herpes viruses, pox viruses, hepadnaviruses, papilloma viruses, adenoviruses, coronoviruses, orthomyxoviruses, paramyxoviruses, flaviviruses, and caliciviruses. For example, the viral disease may be caused by a virus selected from the group consisting of respiratory syncytial virus (RSV), influenza virus, herpes simplex virus, Epstein-Barr virus, varicella virus, cytomegalovirus, hepatitis A virus, hepatitis B virus, hepatitis C virus, human immunodeficiency virus (HIV), human T-lymphotropic virus, calicivirus, adenovirus, and Arena virus.

The viral disease may be, for example, influenza, pneumonia, herpes, hepatitis, hepatitis A, hepatitis B, hepatitis C, chronic fatigue syndrome, sudden acute respiratory syndrome (SARS), gastroenteritis, enteritis, carditis, encephalitis, bronchiolitis, respiratory papillomatosis, meningitis, HIV/AIDS, and mononucleosis.

An isolated or purified T cell may be modified to overexpress Phf19. The T cell may be modified to overexpress Phf19 in any suitable manner. In an embodiment of the invention, the T cell may be modified to overexpress Phf19 using genome editing techniques.

Genome editing techniques can modify gene expression in a target cell by inserting, replacing, or removing DNA in the genome using an artificially engineered nuclease. Examples of such nucleases may include zinc finger nucleases (ZFNs), transcription activator-like effector nucleases (TALENs), the CRISPR/Cas system, and engineered meganucleases. The nucleases create specific double-stranded breaks (DSBs) at targeted locations in the genome, and use endogenous mechanisms in the cell to repair the induced break by homologous recombination (HR) and nonhomologous end-joining (NHEJ). Such techniques may be used to achieve overexpression of Phf19 in T cells.

In another embodiment of the invention, the T cell may be modified (e.g., transduced or transfected) so as to comprise a nucleic acid encoding Phf19. Variants of Phf19 have been identified in *Homo sapiens*, and sequences encoding homologs of Phf19 have been identified at least for *Poeciliopsis prolifica, Microcebus murinus, Meleagris gallopavo, Aptenodytes forsteri, Fukomys damarensis, Gorilla, Xenopus tropicalis*, and *Callithrix jacchus*.

```
The sequence of homo sapiens Phf19 isoform e is
found at GenBank accession No. NP 001273772.1:
MENRALDPGTRDSYGATSHLPNKGALAKVKNNFKDLMSKLTEGQYVLCRW
TDGLYYLGKIKRVSSSKQSCLVTFEDNSKYWVLWKDIQHAGVPGEEPKCN
ICLGKTSGPLNEILICGKCGLVPHPHSGQC, and
it is set forth in SEQ ID NO: 12.

The amino acid sequence of homo sapiens Phf19
isoform d is found at GenBank accession No.
NP 001273771.1:
MLQCYRCRQWFHEACTQCLNEPMMFGDRFYLFFCSVCNQGPEYIERLPLR
WVDVVHLALYNLGVQSKIKKYFDFEEILAFVNHHWELLQLGKLTSTPVTD
RGPHLLNALNSYKSRFLCGKEIKKKKCIFRLRIRVPPNPPGKLLPDKGLL
PNENSASSELKRGKSKPGLLPHEFQQQKRRVYRRKRSKFLLEDAIPSSDF
TSAWSTNHHLASIFDFTLDEIQSLKSASSGQTFFSDVDSTDAASTSGSAS
TSLSYDSRWTVGSRKRKLAAKAYMPLRAKRWAAELDGRCPSDSSAEGASV
PERPDEGIDSHTFESISEDDSSLSHLKSSITNYFGAAGRLACGEKYQVLA
RRVTPEGKVQYLVEWEGTTPY, and
it is set forth in SEQ ID NO: 13.

The amino acid sequence of homo sapiens Phf19
isoform c is found at GenBank accession No.
NP 001273769.1:
MLVLVIRGPYPSAQCQGKLMENRALDPGTRDSYGATSHLPNKGALAKVKN
NFKDLMSKLTEGQYVLCRWTDGLYYLGKIKRVSSSKQSCLVTFEDNSKYW
VLWKDIQHAGVPGEEPKCNICLGKTSGPLNEILICGKCGLGYHQQCHIPI
AGSADQPLLTPWFCRRCIFALAVRKGGALKKGAIARTLQAVKMVLSYQPE
ELEWDSPHRTNQQQCYCYCGGPGEWYLRMLQCYRCRQWFHEACTQCLNEP
MMFGDRFYLFFCSVCNQGPEYIERLPLRWVDVVHLALYNLGVQSKKKYFD
FEEILAFVNHHWELLQLGKLTSTPVTDRGPHLLNALNSYKSRFLCGKEIK
KKKCIFRLRIRVPPNPPGKLLPDKGLLPNENSASSELRKRGKSKPGLLPH
```

```
EFQQQKRRVYRRICRSKFLLEDAIPSSDFTSAWSTNHHLASIFDFTLDEI
QSLKSASSGQTFFSDVDSTDAASTSGSASTSLSYDSRWTVGSRKRKLAAK
AYMPLRAKRWAAELDGRCPSDSSAEGASVPERPDEGIDSHTFESISEDDS
SLSHLKSSITNYFGAAGRLACGEKYQVLARRVTPEGKVQYLVEWEGTTPY,
and it is set forth in SEQ ID NO: 14.

The amino acid sequence of homo sapiens Phf19
isoform b is found at GenBank accession No.
NP 001009936.1:
MENRALDPGTRDSYGATSHLPNKGALAKVKNNFKDLMSKLTEGQYVLCRW
TDGLYYLGKIKRVSSSKQSCLVTFEDNSKYWVLWKDIQHAGVPGEEPKCN
ICLGKTSGPLNEILICGKCGLGYHQQCHIPIAGSADQPLLTPWFCRRCIF
ALAVRVSLPSSPVPASPASSSGADQRLPSQSLSSKQKGHTWALETDSASA
TVLGQDL, and it is set forth in SEQ ID NO: 15.

The amino acid sequence of homo sapiens Phf19
isoform a is found at GenBank accession No.
NP 056466.1:
MENRALDPGTRDSYGATSHLPNKGALAKVKNNFKDLMSKLTEGQYVLCRW
TDGLYYLGKIKRVSSSKQSCLVTFEDNSKYWVLWKDIQHAGVPGEEPKCN
ICLGKTSGPLNEILICGKCGLGYHQQCHIPIAGSADQPLLTPWFCRRCIF
ALAVRKGGALKKGAIARTLQAVKMVLSYQPEELEWDSPHRTNQQQCYCYC
GGPGEWYLRMLQCYRCRQWFHEACTQCLNEPMMFGDRFYLFFCSVCNQGP
EYIERLPLRWVDVVHLALYNLGVQSKKKYFDPEEILAFVNHHWELLQLGK
LTSTPVTDRGPHLLNALNSYKSRFLCGKEIKKKKCIFRLRIRVPPNPPGK
LLPDKGLLPNENSASSELRKRGKSKPGLLPHEFQQQKRRVYRRKRSKFLL
EDAIPSSDFTSAWSTNHHLASIFDFTLDEIQSLKSASSGQTFFSDVDSTD
AASTSGSASTSLSYDSRWTVGSRKRKLAAKAYMPLRAKRWAAELDGRCPS
DSSAEGASVPERPDEGIDSHTFESISEDDSSLSHLKSSITNYFGAAGRLA
CGEKYQVLARRVTPEGKVQYLVEWEGTTPY, and
it is set forth in SEQ ID NO: 9.

The amino acid sequence of mouse Phf19,
NCBI reference sequence NP 082992.1 is:
METQALEPGTLEAFGATSPNKGGLSKTKKNFKDLMSKVTEGQFVLCRWTD
GLYYLGKIKRVSSPKQSCLVTFEDNSKYWVLWKDIQHAGVPGEEPKCDVC
MGKTSGPMNEILICGKCGLGYHQQCHIPIAVDANWPLLTHWFCRRCIFAL
AVRKGGALKKGAIAKTLQAVKMVLSYQPEELDWDSPHRTNQQQCYCYCGG
PGEWYLRMLQCYRCRQWFHEACTQCLSEPMVFGDRFYLFFCSVCNQGPEY
IERLPLRWVDIVHLALYNLGVQSKKRYFDFEEILAFVNHHWELLQLGKLT
STPMTERGPHLLNALNSYKSRFLCGKEIKKKKCIFRLRIRVPPAPPGKLL
PDRALMPSDKGTSELLRKKGKSKPGLLPQEPQQQKRRVYRRKRSKFLLED
AIPSSDFTSAWSTDHHLASIFDFTLDEIQSLKSGSSGQTFFSDVDSTDAA
STSGSASTSLSYDSRWTVGSRKRKLTAKVHRPLRAKQRAAELEGRCASDS
NAEGAVGPEQPDEGIDSHTLESISGDDSSLSHLKSSITNYFGAAGRLACG
EKYRVLARRVTPEGKVQYLLEWEGTTPY, and
it is set forth in SEQ ID NO: 10.
```

Genetic expression vectors useful to overexpress Phf19 are well known in the art. The vector may be a plasmid, a viral vector, a cosmid, or an artificial chromosome. Viral vectors that can be used to deliver nucleic acids into the genetic makeup of cells include engineered retrovirus, lentivirus, adenovirus, adeno-associated virus and herpes simplex virus. It will be apparent to persons or ordinary skill that genetic vectors for introduction and expression of foreign genetic sequences into mammalian cells, such as T cells, typically contain elements of virally-, bacterially-, or both virally- and bacterially-derived DNA (or RNA) in addition to containing or comprising mammalian genetic elements (such as promoters, enhancers, and the like) and the Phf19-encoding sequence. Preferred are any techniques that can efficiently introduce Phf19 into antigen-specific T cells.

Preferably, the nucleic acid is a recombinant nucleic acid. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The terms "nucleic acid" and "polynucleotide," as used herein, refer to a polymeric form of nucleotides of any length, either ribonucleotides (RNA) or deoxyribonucleotides (DNA). These terms refer to the primary structure of the molecule, and thus include double- and single-stranded DNA, double- and single-stranded RNA, and double-stranded DNA-RNA hybrids. The terms include, as equivalents, analogs of either RNA or DNA made from nucleotide analogs and modified polynucleotides such as, though not limited to, methylated and/or capped polynucleotides. Suitable nucleotide analogs are known.

Methods of preparing polynucleotides are within the ordinary skill in the art (Green and Sambrook, *Molecular Cloning: A Laboratory Manual*, (4th Ed.) Cold Spring Harbor Laboratory Press, New York (2012)).

The nucleic acid may comprise any suitable Phf19 nucleotide sequence, which may encode any suitable Phf19 amino acid sequence from any mammal, examples are discussed above.

An embodiment of the invention provides a method for inhibiting T cell terminal differentiation and exhaustion, comprising epigenetically reprogramming the T cell to express Phf19 at a level that is higher than the level of Phf19 expressed by a T cell that has not been epigenetically reprogrammed, wherein the increased expression of Phf19 inhibits T cell terminal differentiation and exhaustion when compared with a T cell not epigenetically reprogrammed by Phf19 overexpression.

The following examples further illustrate the invention but, of course, should not be construed as in any way limiting its scope.

EXAMPLES

As seen in in the Figures and described herein, particularly in these Examples, it appears as if, in the absence of Phf19, CD8+ T cells consistently display impaired expansion and enhanced exhaustion. Also seen in the figures and described herein, overexpression of Phf19 appears to enhance T cell expansion while restraining terminal differentiation and senescence. Thus, enforced expression of Phf19 can greatly augment cellular engraftment, restrict senescence, and sustain cytokine production, resulting in enhanced antitumor immunity by epigenetically reprogramming T cell fate.

The following materials and methods were employed in the experiments described in Examples 1 through 4, below.

Mice and Tumor Lines

C57BL/6 mice were obtained from Charles River Laboratories (Wilmington, MA); although the C57BL/6J strain of mice is refractory to many tumors, it is a permissive background for maximal expression of most mutations. Pmel-1 (B6.Cg-Thy1a/Cy Tg (TcraTcrb)8Rest/J) mice were obtained from the Jackson Laboratory (Bar Harbor, ME); these transgenic mice provide a tumor model system for studies related to immunotherapy, and for studying in vivo T-cell biology Phf19$^{-/-}$ cells were obtained from the Mouse Biology Program at the University of California, Davis (Davis, CA). B16 (H-2$^b$), a gp100+ mouse melanoma, was obtained from the National Cancer Institute Tumor Repository. B16 (H-2$^b$)-hgp100 was obtained from K. Hanada, (Surgery Branch, NCI/NIH, Bethesda, MD). All mouse experiments were done with the approval of the National Cancer Institute Animal Use and Care Committee.

Antibodies, Flow Cytometry and Cell Sorting

Anti-CD8α, anti-CD62L, anti-KLRG1, anti-CD3, anti-CD44, anti-CD25, anti-Ly-5.1, anti-Ly-5.2, anti-Thy-1.1, anti-IL-2, anti-IFN-γ, anti-TNF-α, were obtained from BD Biosciences (Franklin Lakes, NJ). LEUKOCYTE ACTIVATION COCKTAIL containing phorbol myristate acetate and ionomycin (BD Biosciences) was used for the stimulation of T cells for intracellular cytokine staining. A FACSCANTO II or LSR II (BD Biosciences) was used for flow cytometry acquisition. Samples were analyzed with FLOWJO software (TreeStar, Ashland, OR). CD8$^+$GFP$^+$ T cells, CD8$^+$GFP$^+$Thy-1.1$^+$ T cells, CD8$^+$Ly-5.1$^+$ T cells were sorted with a FACSAria (BD Biosciences).

Real-Time RT-PCR

RNA was isolated with a MIRNEASY Mini kit (Qiagen, Germantown, MD) and cDNA was generated by reverse transcription (Applied BioSystems, Foster City, CA), following the manufacturer's protocol. Primers from Applied BioSystems (listed in Table 1), and a PRISM 7900HT (Applied BioSytems) were used for real-time PCR analysis of all genes; results are presented relative to U6 expression.

Immunoblot Analysis

Proteins were separated by 4-20% sodium dodecyl sulfate polyacrylamide gel electrophoresis (SDS-PAGE), followed by standard immunoblot analysis. Anti-pAkt, anti-Ship1, anti-Ezh2 and anti-Suz12 were obtained from Cell Signaling Technology (Danvers, MA). Anti-Jarid2 and anti-H3 were obtained from Abcam (Cambridge, MA). Anti-H3K27me3 and anti-Gapdh were obtained from EMD Millipore (Kankakee, IL). Anti-V5 was obtained from Invitrogen (Carlsbad, CA). Anti-Actin, horseradish peroxidase-conjugated goat anti-mouse IgG, and horseradish peroxidase-conjugated goat anti-rabbit IgG were obtained from Santa Cruz Biotechnology (Dallas, TX). Cells were analyzed by immunoblot 72 hours after transduction.

Retroviral Vector Construction and Retrovirus Production

Phf19 cDNA, Phf19mut cDNA, or Thy1.1 cDNA linked by the sequence encoding the picornavirus 2A ribosomal skip peptide were cloned into the MSGV1 vector (Hughes, M. et al., *Hum. Gene Ther.* 16: 457-472 (2005) (incorporated herein in its entirety by reference)). PLATINUM ECO cell lines (Cell Biolabs, Inc. San Diego, CA) were used for gamma-retroviral production by transfection with DNA plasmids through the use of LIPOFECTAMINE 2000 (Invitrogen) and collection of virus 40 hours after transfection. The nucleotide sequence of the mouse Phf19Thy1.1 vector is set forth in SEQ ID NO: 11; FIG. 9 shows a diagram of this Phf19Thy1.1 vector.

In Vitro Activation and Transduction of CD8$^+$ T Cells

CD8$^+$ T cells were separated from non-CD8$^+$ T cells with a MACS negative selection kit (Miltenyi Biotech, Bergisch Gladbach, Germany) and were activated on plates coated with anti-CD3E (2 μg/ml; BD Biosciences) and soluble anti-CD28 (1 μg/ml; BD Biosciences) in culture medium containing rhIL-2 (120 IU/ml; Chiron, Emeryville, CA). Virus was 'spin-inoculated' at 2,000 g for 2 h at 32° C. onto plates coated with RETRONECTIN recombinant human fibronectin (Takara, Shiga, Japan). CD8$^+$ T cells activated for 24 h were transduced following standard protocols.

Adoptive Cell Transfer, Infection, and Tumor Treatment

Cells ($3 \times 10^5$ to $2 \times 10^6$ cells) were adoptively transferred into hosts followed by infection with recombinant vaccinia virus or fowlpox virus expressing human gp100 (Virapur; San Diego, CA) together with the indicated combination of exogenous cytokines ($2.4e^5$ IU/dose of rhIL-2 for 6 doses every 12 hours). Female C57BL/6 mice were injected subcutaneously with $3 \times 10^5$ B16 melanoma cells.

Enumeration of Adoptively Transferred Cells

Mice were euthanized after infection. Splenocytes were counted by TRYPAN blue exclusion cell viability assay. The frequency of transferred T cells was determined by measurement of the expression of CD8 and GFP (green fluorescent protein), Thy-1.1, by flow cytometry. The absolute number of pmel-1 cells was calculated by multiplication of the total cell count with the percentage of CD8$^+$ GFP$^+$ Thy-1.1$^+$ cells.

Nanostring

Cells were sorted ex vivo and total RNA was isolated with a miRNEASY Mini kit (Qiagen, Velno, Netherlands). Ten ng total RNA was used for Nanostring analysis following the Nanostring® nCounter® Expression CodeSet Design Manual. Background levels were calculated and subtracted from the samples, which were then normalized against the positive control and housekeeping gene probes. Expression heat maps were generated with the R package ComplexHeatmap (Bioconductor, Open Source Software for Bioinformatics), as described in Gu et., "Complex heatmaps reveal patterns and correlations in multidimensional genomic data, *Bioinformatics,* 32(18):2847-9 (2016), which is herein incorporated by reference.

RNA-seq

Ribonucleic acid (RNA) concentration was determined with the QUBIT RNA broad range assay in the QUBIT Fluorometer (Invitrogen). The RNA integrity was determined with Eukaryote TOTAL RNA NANO SERIES II ChIP on a 2100 Bioanalyzer (Agilent Technologies, Santa Clara, CA). RNA-seq libraries were prepared from 4 μg of total RNA via the TRUSEQ RNA sample prep kit according to manufacturer's protocol (Illumina, San Diego, CA). In brief, oligo-dT purified mRNA was fragmented and subjected to first and second strand cDNA synthesis. cDNA fragments were blunt-ended, ligated to ILLUMINA adaptors, and PCR amplified to enrich for the fragments ligated to adaptors. The resulting cDNA libraries were verified and quantified on Agilent Bioanalyzer and single-end 96 cycle RNA-seq was conducted with the GAIIX Genome Analyzer (Illumina).

RNA-seq analyses were performed using ≥2 biological replicates. For RNA sequencing, total RNA was prepared from cells using the RNEASY PLUS Mini Kit (Qiagen). 200 ng total RNA was subsequently used to prepare an RNA-seq library by using TRUSEQ RNA sample prep kit (FC-122-1001, Illumina) according to the manufacturer's instructions. Sequenced reads were aligned to the mouse genome (NCBI37/mm9) using TOPHAT 2.0.11 (Jonhs Hopkins University Center for Computational Biology; Baltimore, MD), and uniquely mapped reads were used to calculate gene expression. REFSEQ gene database (mm9) was downloaded from the UCSC genome browser for RNA-seq analysis. Raw counts that fell on exons of each gene were calculated, and differentially expressed genes were identified with the statistical R PACKAGE EDGER52 or CUFFDIFF53. Fisher's exact test or t-test were used to evaluate significance with indicated P value and fold-change thresholds. Expression heat maps were generated with the R package PHEATMAP.

Gene-Set Enrichment Analysis (GSEA) of RNA-Seq Data

Mouse gene symbols were first mapped to the orthologous human genes using homology information available from Mouse Genome Informatics (MGI) (see http://www.informatics.jax.org and ftp://ftp.informatics.jax.org) and were ranked by the fold changes of the gene expression as profiled by RNA-seq. Then, gene set enrichment was analyzed using GSEA software available from the Broad Institute website (www.software.broadinstitute.org).

ChIP-seq

T cells were crosslinked with 2% paraformaldehyde at room temperature for 10 min and lysed in Farnham buffer (5 mM PIPES pH 8.0; 85 mM KCl; 0.5% NP-40) and subsequently in RIPA buffer (lx PBS; 1% NP-40; 0.5% sodium deoxycholate; 0.1% SDS). Sheared chromatin was immunoprecipitated with anti-H3K27me3 antibody (Millipore, 07-449) and washed successively in buffer I (20 mM Tris HCl pH 8.0, 150 mM NaCl, 2 mM EDTA, 0.1% SDS, 1% Triton X-100); buffer II (20 mM Tris HCl pH 8.0, 500 mM NaCl, 2 mM EDTA, 0.1% SDS, 1% Triton X-100); three times of buffer III (100 mM Tris HCl pH 8.0, 500 mM LiCl, 1% NP-40; 1% sodium deoxycholate). For sequencing of immunoprecipitated DNA, DNA fragments were blunt-end ligated to Illumina adaptors, amplified, and sequenced by using the HiSeq 2000 platform (Illumina). Single-end reads of 50 bp were obtained by using the Illumina Pipeline (Illumina). Sequenced reads were aligned to the mouse genome (NCBI37/mm9) with Bowtie 2.2.8; only uniquely mapped reads were retained. H3K27me3 enriched regions were detected using SICER algorithm, described in Xu et al., "Spatial clustering for identification of ChIP-enriched regions (SICER) to map regions of histone methylation patterns in embryonic stem cells," Methods Mol Biol., 1150:97-11 (2014), herein incorporated by reference, and the window size, gap size, and FDR were set to 200 bp, 600 bp, and 5%, respectively. Genomic graphs were generated and viewed using the INTEGRATIVE GENOMICS VIEWER (IGV), described in Robinson et al., "Integrative Genomics Viewer," *Nature Biotechnology*, 29, 24-26 (2011) (incorporated herein in its entirety by reference)).

Statistical Analyses

A two-tailed student t test was used for comparison of data such as gene expression levels, cell proliferation and functionality (numbers and percent), and tumor growth slopes. A Log-rank (Mantel-Cox) Test was used for comparison of survival curves.

Primers Used

Table 1 lists the nucleotide sequences of the qPCR primers used in the experiments described herein.

TABLE 1

| Name | qPCR Primer sequence: | SEQ ID NO: |
|---|---|---|
| Phf19F | TGACAGAGGGACAGTTCGTG | 1 |
| Phf19R | GATCTCGTTCATAGGCCCTGA | 2 |
| miR-155 | mmu-miR-155-5p (002571, Life Technologies) UUAAUGCUAAUUGUGAUAGGGGU | 3 |
| U6: | U6 snRNA (001973, Life Technologies) GTGCTCGCTTCGGCAGCACATATACTAAAA TTGGAACGATACAGAGAAGATTAGCATGGC CCCTGCGCAAGGATGACACGCAAATTCGTG AAGCGTTCCATATTTT | 4 |
| Rpl13F | CGAGGCATGCTGCCCCACAA | 5 |
| Rpl13R | AGCAGGGACCACCATCCGCT | 6 |
| Ezh2F | AGTGACTTGGATTTTCCAGCAC | 16 |
| Ezh2R | AATTCTGTTGTAAGGGCGACC | 17 |

Table 2 lists the nucleotide sequences of the ChIP primers used in the experiments described herein.

TABLE 2

| Name | ChIP PCR Primer sequence: (from mouse genome assembly GRCm38.p5) | SEQ ID NO: |
|---|---|---|
| EomesF | GAGCTTGCTCTAGGGGTAGG (Chromosome 9: 118,476,227-118,476,247) | 18 |
| EomesR | ACAGCCAGAAGTAAGGTCCC (Chromosome 9: 118,476,388-118,476,408) | 19 |
| Id2F | CGCCACAATTCCGACCTTAG (Chromosome 12: 25,100,336-25,100,356) | 20 |
| Id2R | AAATATTTGCGGCGCTCCAT (Chromosome 12: 25,100,545-25,100,565) | 21 |
| Prdm1F | TTGGGGCACAGATACCATGT (Chromosome 10: 44,460,649-44,460,669) | 22 |
| Prdm1R | TCCTCCCTAGACTCAAGCCT (Chromosome 10: 44,460,841-44,460,861) | 23 |
| MafF | CTGCAGACATTTTGAGGCGT (Chromosome 8: 118,236,772-118,236,792) | 24 |
| MafR | TCTAACTGAGCCGGTGTTGT (Chromosome 8: 118,236,930-118,236,950) | 25 |
| Nr4a2F | TGGTTGTTCTAGGGCGTGAT (Chromosome 2: 56,944,999-56,945,019) | 26 |
| Nr4a2R | TACCCGGCCAAACTCTCAAT (Chromosome 2: 56,944,999-56,945,019) | 27 |
| Zeb2F | TGAAATTCCACCTCCCTCCC (Chromosome 2: 56,945,135-56,945,155) | 28 |
| Zeb2R | TCCCTTTAACTTTCGCCCCT (Chromosome 2: 45,113,439-45,113,459) | 29 |

Example 1

This example demonstrates that Phf19 is a critical downstream factor of miR-155 in CD8+ T cells.

To identify potential downstream targets of miR-155 involved in Polycomb Repressive Complex 2 (PRC2) function, the RNA-seq data set was re-examined comparing KLRG1−CD62L−CD8+ T cells overexpressing miR-155 (miR-155 cells) and the CD8+ T cells not overexpressing miR-155 (Ctrl cells). The PHD finger protein 19 (Phf19) is a polycomb-like protein that recruits the PRC2 to specific genomic targets by binding to histone H3 trimethylated at Lysine 36 (H3K36me3) (Bellaré C et al., *Nat. Struct. Mol. Biol.* 19: 1257-1265 (2012) (incorporated herein in its entirety by reference)). Phf19 was strongly upregulated in miR-155 cells as compared to Ctrl cells (FIG. 1A). This observation was further validated by qPCR analysis, which demonstrated that, as seen in FIG. 1B, miR-155 cells contained nearly 3-fold higher Phf19 transcripts than Ctrl cells. Conversely, Phf19 levels were significantly reduced in miR-155-deficient CD8+ T cells compared to wild-type cells (FIG. 1C).

Phf19 expression has been reported to be upregulated by pAkt in cancer cells, and Akt signaling is heightened by miR-155 through repression of inositol polyphosphate-5-phosphatase D (also known as Ship-1), a well-established negative regulator of Akt (Ji Y et al., *P. N. A. S. USA*, 112:476-481(2015); published electronically as doi: 10.1073/pnas.1422916112. Epub (2014) (incorporated herein in its entirety by reference)) (FIGS. 1D and 1E). To determine whether miR-155 induced Phf19 by enhancing Akt signaling, Phf19 expression was measured in miR-155 cells and Ctrl miR-overexpressing cells that were concomitantly transduced with a constitutively active form of Akt (AktCA), or the Thy1.1 control. It was found that miR-155 upregulated Phf19 in Thy1.1 co-transduced cells (FIG. 1F). Also shown in FIG. 1F, constitutive Akt signaling drove Phf19 expression to saturation, abrogating any further upregulation of Phf19 by miR-155. Next, whether downregulation of Ship1 alone would induce Phf19 was tested. To delete Ship1 in CD8$^+$ T cells, Cas9$^+$CD8$^+$ T cells were transduced with a retroviral vector encoding a sgRNA targeting Ship1 exon 5 (FIG. 1G). Ship1 knockdown resulted in both enhanced pAkt levels and a substantial upregulation of Phf19 expression in CD8$^+$ T cells (FIGS. 1G and 1H).

Next, whether Phf19 expression was dynamically regulated in CD8$^+$ T cells responding to gp100-VV infection was determined. It was found that Phf19 was strongly induced at the early stages of acute immune response, sharply downregulated at peak effector response and maintained at low levels throughout transition to memory phase (FIG. 2A). These findings suggested a potential role of Phf19 in regulating CD8$^+$ T cell effector differentiation. The rapid spike of induction was similarly observed for Ezh2, indicating coordinated expression of PRC2 and its associated factor Phf19 during the immune response (FIG. 2B). Mir155 followed a virtually identical pattern of expression, emphasizing the interplay between these molecules during physiologic immune response (FIG. 2B).

To investigate whether Phf19 phenocopies miR-155 effects in restraining CD8$^+$ T cell differentiation, the induction of short-lived KLRG1$^+$CD62L$^-$ effectors was evaluated in cells lacking Phf19 after transfer of naïve CD8$^+$ T cells into wild-type mice infected with a recombinant strain of vaccinia virus encoding the cognate antigen gp100 (gp100-VV). As seen in FIGS. 2G and 2H, the Phf19$^{-/-}$ T cells were more prone to undergo terminal differentiation as shown by the increased frequency and number of T$_E$ cells (FIGS. 2G and 2H) and reduced percentages of KLRG1$^-$CD62L$^+$ memory precursors (FIG. 2I). Although expressing minimum amounts of Phf19 no gross alterations in T cell development and homeostasis were found in Phf19 deficient animals (FIGS. 2C-2F). Consistent with this defect in memory precursor formation, reduced frequency and absolute number of memory cells in Phf19$^{-/-}$ cells was observed, though no major difference in the distribution of memory subsets was detected (FIGS. 2J and 2K).

To test whether Phf19 promoted the silencing of the pro-effector and pro-exhaustion TFs that were suppressed by miR-155 overexpression, a H3K27me3 ChIP qPCR analysis was performed on KLRG1$^-$ T cells in the presence and absence of Phf19. In Phf19$^{-/-}$ CD8$^+$ T cells a reduced deposition of H3K27me3 was observed at all previously shown TFs targeted in miR-155-overexpressing cells (FIG. 2L), suggesting that Phf19 and miR-155 regulate a common core molecular program.

Taken together, these results suggest that similar to miR-155, Phf19 enhances T cell expansion while restraining terminal differentiation and senescence.

To determine whether the transcriptional program underlying Phf19 activity overlaid with the gene expression profile of miR-155 cells, the transcriptome of KLRG1$^-$CD62L$^-$ Phf19$^{-/-}$ cells and miR-155 cells isolated at the peak of the immune response were compared. There were 346 genes significantly changed in Phf19$^{-/-}$ cells compared to wild-type cells. Of these significantly changed genes, 166 genes were also differentially regulated in miR-155 cells compared to Ctrl cells. Nearly 65% of the genes downregulated in Phf19$^{-/-}$ T cells, were significantly upregulated in miR-155-overexpressing cells (P=2.2e-16) (FIGS. 3A and 3B). About ⅙ of genes upregulated in Phf19$^{-/-}$ cells were downregulated in miR-155-overexpressing cells (P=4.9e-11) (FIGS. 3A and 3B). This high degree of overlap in the transcriptional programs of miR-155 and Phf19 was further supported by Gene Set Enrichment Analyses (GSEA analyses) which revealed that numerous gene sets displayed opposite enrichment pattern in miR-155-overexpressing cells and Phf19 deficient cells (FIGS. 3C and 3D and Tables 3 and 4, provided herein).

Among 32 datasets positively enriched in Phf19$^{-/-}$ cells, >50% were also negatively enriched in miR-155-overexpressing cells (P=1.43e-6). Of 1,113 datasets, 1,012 negatively enriched in Phf19$^{-/-}$ cells were positively enriched in miR-155-overexpressing cells (P=2.2e-16) (FIG. 3C). For instance, genes upregulated in primary versus secondary CD8$^+$ T cell responses against LCMV infection, which represent a molecular signature of less-differentiated cells, were enriched in miR-155-overexpressing cells but depleted in Phf19$^{-/-}$ cells (FIG. 3D, left panels). Likewise, genes upregulated in d6 versus d10 post LmOVA infections, which represent a molecular signature of more-proliferative cells, were enriched in miR-155-overexpressing cells but depleted in Phf19$^{-/-}$ cells (FIG. 3D, right panels). These results demonstrate that Phf19 and miR-155 orchestrate an extensively shared transcriptional program, establishing Phf19 as a downstream factor of miR-155.

Example 2

This example demonstrates that Phf19 is essential to enhance proliferation and restrict exhaustion of miR-155 cells.

The experiments in this example were performed to test whether the enhanced immune responses mediated by miR-155 were dependent on Phf19 function. The immune response of miR-155 or Ctrl-miR overexpressing T cells in Phf19 sufficient and deficient pmel-1 cells. The results are consistent with the view that Phf19 is a downstream factor contributing to the benefits conferred by miR-155 overexpression. As seen in FIGS. 3E, 3F, and 3G, the miR-155 overexpressing Phf19$^{-/-}$ T cells had a defect in expansion compared to miR-155 Phf19$^{+/+}$ T cells, which exceeded that observed in Ctrl Phf19$^{-/-}$ T cells compared to Ctrl Phf19$^{+/+}$ T cells. As seen in FIG. 3G, Phf19$^{-/-}$ T cells were more prone to undergo terminal differentiation even with enforced miR-155 expression as shown by the increased frequencies of KLRG1$^+$CD62L$^-$ cells.

These results indicate that Phf19 is a downstream factor of miR-155 in mediating T cell expansion and restricting exhaustion and senescence.

Example 3

This example demonstrates that enforced expression of Phf19 restricts CD8$^+$ T cell senescence and functional exhaustion.

Whether the enforced expression of Phf19 would mimic the functional effects induced by miR-155 overexpression was evaluated. Following gp100-VV infection, pmel-1 cells transduced with Phf19Thy1.1 or Thy1.1 alone were adoptively transferred into wild-type mice. Reminiscent of miR-155 T cells, Phf19-overexpressing cells displayed enhanced proliferation (FIG. 4A), reduced terminal differentiation (FIG. 4B), sustained polyfunctionality, and IFN-γ production (FIG. 4C). As shown in FIGS. 4D and 4E, enforced expression of Phf19 enhances CD8+ T cell long-term memory. Furthermore, as seen in FIGS. 4F and 4G, Phf19-overexpressing cells demonstrated a dramatic and long-lasting antitumor activity resulting in better overall survival.

Altogether, these findings indicate that enforced expression of Phf19 can greatly augment cellular engraftment, restrict senescence, and sustain cytokine production, resulting in enhanced efficacy of T cell-based immunotherapy.

Example 4

This example demonstrates that Phf19 overexpression enhances CD8+ T cell antitumor immunity by epigenetically reprogramming T cell differentiation.

One important feature of Phf19 for regulating PRC2 activity is to recruit the PRC2 to histone through its chromatin binding capacity. Therefore, a Phf19 mutant (Phf19mut), with attenuated chromatin binding-capacity to test whether the effects mediated by Phf19 overexpression were dependent on epigenetic mechanisms was generated. In this mutant form of Phf19, two amino acids (W41 and Y47) in the aromatic cage of the Tudor domain required to bind to chromatin, were mutated to W41C and Y47A, respectively (FIG. 5A). The amino acid sequence of the wild-type region of Phf19 is set forth in SEQ ID NO: 7 (Wt). Considerably less Phf19 protein in the chromatin fraction was consistently detected when CD8+ T cells were transduced with Phf19mut (FIG. 5B). The amino acid sequence of the mutated Phf19 region is set forth in SEQ ID NO: 8 (Mut). SEQ ID NO: 8 is SKVTEGQFVLCRCTDGLYAL-GKIKRVSSPKQ.

Overexpression of Phf19 but not Phf19mut enhanced Ezh2 association to chromatin and H3K27me3 deposition in CD8+ T cells. (FIGS. 5C and 5D). Following gp100-VV infection, pmel-1 cells transduced with Phf19Thy1.1, Phf19mutThy1.1, or Thy1.1 alone were adoptively transferred into wild-type mice and T cell expansion, function, and differentiation in response to gp100-VV infection were measured. Reminiscent of miR-155-overexpressing T cells, Phf19-transduced cells expanded more robustly than Thy.1.1 controls (FIGS. 5E and 5F), and displayed limited senescence (FIGS. 5G and 5H) and sustained cytokine production (FIGS. 5I and 5J), and augmented memory precursor formation (FIGS. 5K and 5L). These functional advantages were almost abrogated in cells transduced with Phf19mut (FIGS. 5E-5J), indicating that Phf19 activity was dependent on its capacity to remodeling chromatin. As seen in FIG. 5J, Phf19mut-overexpressing cells displayed certain advantages in sustaining polyfunctionality, but the capacity to enhance cellular engraftment and reduce terminal differentiation mediated by its wild-type allele was greatly attenuated.

Lastly, to evaluate whether the epigenetic reprogramming mediated by Phf19 resulted in augmented antitumor function, pmel-1 cells overexpressing Phf19, Phf19mut, or Thy1.1 were adoptively transferred into tumor-bearing mice in conjunction with administration of gp100-VV and IL-2. It was found that Phf19 cells mediated a dramatic and long-lasting antitumor response resulting in increased mice survival compared to Thy1.1 controls (FIGS. 5M and 5N). These therapeutic benefits, however, were greatly reduced in mice receiving Phf19mut cells resulting in increased mice survival compared to Thy1.1 controls (FIGS. 5M and 5N), indicating that the chromatin binding capacity of Phf19 was critical for the enhanced CD8+ T cell antitumor immunity.

These examples demonstrate that miR-155 enhances the anti-tumor response by epigenetically restricting CD8+ T cell differentiation and functional exhaustion. These examples further demonstrate that miR-155 promoted PRC2 activity to silence key TFs known to drive terminal differentiation and exhaustion. The miR-155-Jarid2-PRC2 axis had only a minor inhibitory role in CD8+ T cell immune responses to both virus and cancer. Instead, it was discovered that miR-155 influenced PRC2 function by indirectly inducing Phf19 expression (FIG. 6).

Furthermore, Phf19 also restrains the differentiation of human T cells, as shown in FIG. 7. A highly conserved core of genes regulated in mouse and human T cells by Phf19 is shown in FIG. 8. Taken together, the restriction of T cell terminal differentiation by Phf19 is highly conserved between mouse and human.

TABLE 3

Gene datasets shared between Phf19$^{-/-}$ (negatively) and miR-155 cells (positively) (FDR q < 0.25)

GSE13547_CTRL_VS_ANTI_IGM_STIM_BCELL_12H_UP
GOBERT_OLIGODENDROCYTE_DIFFERENTIATION_UP
GSE15750_DAY6_VS_DAY10_TRAF6KO_EFF_CD8_TCELL_UP
GSE15750_DAY6_VS_DAY10_EFF_CD8_TCELL_UP
MODULE_54
DUTERTRE_ESTRADIOL_RESPONSE_24HR_UP
GSE14415_NATURAL_TREG_VS_TCONV_DN
ROSTY_CERVICAL_CANCER_PROLIFERATION_CLUSTER
GSE39110_DAY3_VS_DAY6_POST_IMMUNIZATION_CD8_TCELL_DN
KOBAYASHI_EGFR_SIGNALING_24HR_DN
GSE13547_CTRL_VS_ANTI_IGM_STIM_BCELL_2H_UP
CHIANG_LIVER_CANCER_SUBCLASS_PROLIFERATION_UP
CHANG_CYCLING_GENES
GSE30962_PRIMARY_VS_SECONDARY_ACUTE_LCMV_INF_CD8_TCELL_UP
MARSON_BOUND_BY_E2F4_UNSTIMULATED
GSE14415_INDUCED_VS_NATURAL_TREG_DN
KONG_E2F3_TARGETS
SOTIRIOU_BREAST_CANCER_GRADE_1_VS_3_UP
ODONNELL_TFRC_TARGETS_DN
GRAHAM_CML_DIVIDING_VS_NORMAL_QUIESCENT_UP
BASAKI_YBX1_TARGETS_UP
GSE14415_INDUCED_TREG_VS_TCONV_UP
GAVIN_FOXP3_TARGETS_CLUSTER_P6
ZHOU_CELL_CYCLE_GENES_IN_IR_RESPONSE_24HR
ZHANG_TLX_TARGETS_60HR_DN
GNF2_RRM1
HALLMARK_G2M_CHECKPOINT

TABLE 3-continued

Gene datasets shared between Phf19$^{-/-}$ (negatively) and miR-155 cells (positively) (FDR q < 0.25)

GO_CHROMOSOME_SEGREGATION
GSE39556_CD8A_DC_VS_NK_CELL_MOUSE_3H_POST_POLYIC_INJ_UP
GO_KINETOCHORE
GSE36476_CTRL_VS_TSST_ACT_72H_MEMORY_CD4_TCELL_YOUNG_DN
GRAHAM_NORMAL_QUIESCENT_VS_NORMAL_DIVIDING_DN
GO_SISTER_CHROMATID_SEGREGATION
GO_CHROMOSOME_CENTROMERIC_REGION
GNF2_PCNA
GSE14415_TCONV_VS_FOXP3_KO_INDUCED_TREG_DN
MORI_IMMATURE_B_LYMPHOCYTE_DN
CROONQUIST_IL6_DEPRIVATION_DN
GNF2_CCNA2
GO_NUCLEAR_CHROMOSOME_SEGREGATION
GSE13547_2H_VS_12_H_ANTI_IGM_STIM_BCELL_DN
GO_SISTER_CHROMATID_COHESION
GNF2_CENPE
GNF2_CDC20
GSE36476_CTRL_VS_TSST_ACT_40H_MEMORY_CD4_TCELL_YOUNG_DN
GNF2_SMC4L1
GO_CONDENSED_CHROMOSOME_CENTROMERIC_REGION
BURTON_ADIPOGENESIS_3
GNF2_CCNB2
SARRIO_EPITHELIAL_MESENCHYMAL_TRANSITION_UP
REACTOME_MITOTIC_PROMETAPHASE
WHITEFORD_PEDIATRIC_CANCER_MARKERS
LEE_EARLY_T_LYMPHOCYTE_UP
GSE21063_WT_VS_NFATC1_KO_8H_ANTI_IGM_STIM_BCELL_UP
GSE27241_WT_VS_RORGT_KO_TH17_POLARIZED_CD4_TCELL_UP
ISHIDA_E2F_TARGETS
VECCHI_GASTRIC_CANCER_EARLY_UP
GSE24634_TEFF_VS_TCONV_DAY7_IN_CULTURE_UP
GNF2_HMMR
HOFFMANN_LARGE_TO_SMALL_PRE_BII_LYMPHOCYTE_UP
GOLDRATH_ANTIGEN_RESPONSE
GSE5679_CTRL_VS_PPARG_LIGAND_ROSIGLITAZONE_TREATED_DC_UP
GNF2_CDC2
HORIUCHI_WTAP_TARGETS_DN
GO_CONDENSED_CHROMOSOME
GSE2405_S_AUREUS_VS_UNTREATED_NEUTROPHIL_DN
MARKEY_RB1_ACUTE_LOF_UP
GO_MITOTIC_NUCLEAR_DIVISION
GSE45365_HEALTHY_VS_MCMV_INFECTION_CD11B_DC_DN
GNF2_CENPF
ZHANG_TLX_TARGETS_36HR_DN
REACTOME_MITOTIC_M_M_G1_PHASES
ZHANG_TLX_TARGETS_DN
REACTOME_DNA_REPLICATION
SHEDDEN_LUNG_CANCER_POOR_SURVIVAL_A6
GSE33292_WT_VS_TCF1_KO_DN3_THYMOCYTE_DN
HALLMARK_E2F_TARGETS
ZHENG_GLIOBLASTOMA_PLASTICITY_UP
KANG_DOXORUBICIN_RESISTANCE_UP
GOLDRATH_EFF_VS_MEMORY_CD8_TCELL_UP
GSE10239_NAIVE_VS_DAY4.5_EFF_CD8_TCELL_DN
GNF2_CKS2
GSE35543_IN_VITRO_ITREG_VS_CONVERTED_EX_ITREG_UP
FUJII_YBX1_TARGETS_DN
WINNEPENNINCKX_MELANOMA_METASTASIS_UP
MORI_LARGE_PRE_BII_LYMPHOCYTE_UP
AFFAR_YY1_TARGETS_DN
FURUKAWA_DUSP6_TARGETS_PCI35_DN
GOLDRATH_NAIVE_VS_EFF_CD8_TCELL_DN
ODONNELL_TARGETS_OF_MYC_AND_TFRC_DN
REACTOME_CELL_CYCLE_MITOTIC
GSE24634_TEFF_VS_TCONV_DAY10_IN_CULTURE_UP
MISSIAGLIA_REGULATED_BY_METHYLATION_DN
REACTOME_CELL_CYCLE
GNF2_RRM2
ZHAN_MULTIPLE_MYELOMA_PR_UP
GSE24634_TREG_VS_TCONV_POST_DAY7_IL4_CONVERSION_UP
GSE36476_CTRL_VS_TSST_ACT_72H_MEMORY_CD4_TCELL_OLD_DN
FERREIRA_EWINGS_SARCOMA_UNSTABLE_VS_STABLE_UP
GSE13547_2H_VS_12_H_ANTI_IGM_STIM_BCELL_UP
GSE40274_FOXP3_VS_FOXP3_AND_EOS_TRANSDUCED_ACTIVATED_CD4_TCELL_DN
LE_EGR2_TARGETS_UP
GSE25088_WT_VS_STAT6_KO_MACROPHAGE_IL4_STIM_DN
GSE10239_NAIVE_VS_KLRG1HIGH_EFF_CD8_TCELL_DN
SHEPARD_CRUSH_AND_BURN_MUTANT_DN

TABLE 3-continued

Gene datasets shared between Phf19$^{-/-}$ (negatively) and miR-155 cells (positively) (FDR q < 0.25)

RPS14_DN.V1_DN
GSE18893_TCONV_VS_TREG_24H_TNF_STIM_UP
GO_CHROMOSOMAL_REGION
CROONQUIST_NRAS_SIGNALING_DN
GO_ORGANELLE_FISSION
GNF2_BUB1
GNF2_BUB1B
GNF2_ESPL1
GSE23568_CTRL_VS_ID3_TRANSDUCED_CD8_TCELL_DN
GSE36476_CTRL_VS_TSST_ACT_40H_MEMORY_CD4_TCELL_OLD_DN
BENPORATH_CYCLING_GENES
GSE29614_CTRL_VS_DAY7_TIV_FLU_VACCINE_PBMC_DN
WHITFIELD_CELL_CYCLE_G2_M
WHITFIELD_CELL_CYCLE_LITERATURE
AMUNDSOM_GAMMA_RADIATION_RESPONSE
GSE7764_IL15_TREATED_VS_CTRL_NK_CELL_24H_UP
GNF2_MCM4
ZHOU_CELL_CYCLE_GENES_IN_IR_RESPONSE_6HR
NUYTTEN_EZH2_TARGETS_DN
GO_SPINDLE
GO_ATP_DEPENDENT_CHROMATIN_REMODELING
GSE37532_WT_VS_PPARG_KO_VISCERAL_ADIPOSE_TISSUE_TREG_UP
GNF2_CKS1B
GSE28726_NAIVE_CD4_TCELL_VS_NAIVE_VA24NEG_NKTCELL_UP
GNF2_SMC2L1
CHICAS_RB1_TARGETS_GROWING
GSE2405_HEAT_KILLED_LYSATE_VS_LIVE_A_PHAGOCYTOPHILUM_STIM_NEUTROPHIL_9H_UP
PUJANA_XPRSS_INT_NETWORK
GO_CENTROMERE_COMPLEX_ASSEMBLY
GSE22313_HEALTHY_VS_SLE_MOUSE_CD4_TCELL_DN
GSE28726_NAIVE_VS_ACTIVATED_CD4_TCELL_DN
GSE40274_CTRL_VS_FOXP3_TRANSDUCED_ACTIVATED_CD4_TCELL_UP
GSE5679_CTRL_VS_RARA_AGONIST_AM580_TREATED_DC_UP
GSE25088_WT_VS_STAT6_KO_MACROPHAGE_DN
WHITFIELD_CELL_CYCLE_G2
CHEMNITZ_RESPONSE_TO_PROSTAGLANDIN_E2_UP
NAKAYAMA_SOFT_TISSUE_TUMORS_PCA2_UP
GSE21670_UNTREATED_VS_TGFB_IL6_TREATED_CD4_TCELL_UP
GSE11386_NAIVE_VS_MEMORY_BCELL_UP
FOURNIER_ACINAR_DEVELOPMENT_LATE_2
GNF2_FEN1
GO_SPINDLE_POLE
GO_CELL_DIVISION
GSE40274_CTRL_VS_EOS_TRANSDUCED_ACTIVATED_CD4_TCELL_UP
BLUM_RESPONSE_TO_SALIRASIB_DN
GNF2_RFC4
YU_MYC_TARGETS_UP
PID_PLK1_PATHWAY
GSE39110_UNTREATED_VS_IL2_TREATED_CD8_TCELL_DAY3_POST_IMMUNIZATION_DN
CROONQUIST_NRAS_VS_STROMAL_STIMULATION_DN
GSE7852_LN_VS_THYMUS_TCONV_DN
GSE45365_WT_VS_IFNAR_KO_CD11B_DC_MCMV_INFECTION_DN
GSE45365_WT_VS_IFNAR_KO_BCELL_DN
MOLENAAR_TARGETS_OF_CCND1_AND_CDK4_DN
GSE24634_IL4_VS_CTRL_TREATED_NAIVE_CD4_TCELL_DAY7_UP
GO_DNA_REPLICATION_INDEPENDENT_NUCLEOSOME_ORGANIZATION
GSE12392_CD8A_POS_VS_NEG_SPLEEN_DC_DN
GSE22601_DOUBLE_POSITIVE_VS_CD4_SINGLE_POSITIVE_THYMOCYTE_DN
GSE26156_DOUBLE_POSITIVE_VS_CD4_SINGLE_POSITIVE_THYMOCYTE_DN
GSE32901_NAIVE_VS_TH17_NEG_CD4_TCELL_UP
GNF2_H2AFX
YANG_BCL3_TARGETS_UP
PUJANA_BRCA2_PCC_NETWORK
LINDGREN_BLADDER_CANCER_CLUSTER_1_DN
GO_HISTONE_EXCHANGE
GSE15930_NAIVE_VS_72H_IN_VITRO_STIM_TRICHOSTATINA_CD8_TCELL_DN
GSE10239_NAIVE_VS_KLRG1INT_EFF_CD8_TCELL_DN
PUJANA_BRCA_CENTERED_NETWORK
GSE40666_WT_VS_STAT1_KO_CD8_TCELL_WITH_IFNA_STIM_90MIN_DN
BERENJENO_TRANSFORMED_BY_RHOA_UP
GSE20366_EX_VIVO_VS_HOMEOSTATIC_CONVERSION_TREG_DN
GNF2_TTK
WU_APOPTOSIS_BY_CDKN1A_VIA_TP53
BENPORATH_PROLIFERATION
GSE15930_NAIVE_VS_24H_IN_VITRO_STIM_CD8_TCELL_DN
SENGUPTA_NASOPHARYNGEAL_CARCINOMA_UP
GSE14350_TREG_VS_TEFF_IN_IL2RB_KO_DN
RUIZ_TNC_TARGETS_DN

TABLE 3-continued

Gene datasets shared between Phf19−/− (negatively) and miR-155 cells (positively) (FDR q < 0.25)

GO_MITOTIC_CELL_CYCLE
GO_DNA_PACKAGING
GO_REGULATION_OF_SISTER_CHROMATID_SEGREGATION
MORF_BUB1B
LINDGREN_BLADDER_CANCER_CLUSTER_3_UP
GSE45365_HEALTHY_VS_MCMV_INFECTION_CD11B_DC_IFNAR_KO_DN
GO_DNA_REPLICATION_INDEPENDENT_NUCLEOSOME_ASSEMBLY
GSE17974_0H_VS_24H_IN_VITRO_ACT_CD4_TCELL_DN
REACTOME_CHROMOSOME_MAINTENANCE
PUJANA_BREAST_CANCER_WITH_BRCA1_MUTATED_UP
GO_REGULATION_OF_CHROMOSOME_SEGREGATION
GSE5589_WT_VS_IL10_KO_LPS_STIM_MACROPHAGE_45MIN_UP
GREENBAUM_E2A_TARGETS_UP
GSE32164_RESTING_DIFFERENTIATED_VS_ALTERNATIVELY_ACT_M2_MACROPHAGE_UP
REACTOME_G2_M_CHECKPOINTS
WILCOX_RESPONSE_TO_PROGESTERONE_UP
GSE43863_TH1_VS_LY6C_LOW_CXCR5NEG_EFFECTOR_CD4_TCELL_UP
MODULE_57
LI_WILMS_TUMOR_VS_FETAL_KIDNEY_1_DN
GSE12845_IGD_POS_BLOOD_VS_PRE_GC_TONSIL_BCELL_DN
MORI_PRE_BI_LYMPHOCYTE_UP
REACTOME_E2F_MEDIATED_REGULATION_OF_DNA_REPLICATION
KAMMINGA_EZH2_TARGETS
GSE24671_BAKIMULC_VS_SENDAI_VIRUS_INFECTED_MOUSE_SPLENOCYTES_UP
GSE9650_EFFECTOR_VS_MEMORY_CD8_TCELL_UP
KAECH_DAY8_EFF_VS_MEMORY_CD8_TCELL_UP
KAUFFMANN_MELANOMA_RELAPSE_UP
GSE24574_BCL6_LOW_TFH_VS_TCONV_CD4_TCELL_DN
REN_BOUND_BY_E2F
GSE21063_CTRL_VS_ANTI_IGM_STIM_BCELL_NFATC1_KO_8H_DN
FARMER_BREAST_CANCER_CLUSTER_2
GSE29614_CTRL_VS_TIV_FLU_VACCINE_PBMC_2007_DN
GO_DNA_REPLICATION
GARGALOVIC_RESPONSE_TO_OXIDIZED_PHOSPHOLIPIDS_TURQUOISE_DN
GSE15930_NAIVE_VS_24H_IN_VITRO_STIM_IL12_CD8_TCELL_DN
SHEPARD_BMYB_TARGETS
GSE14415_INDUCED_TREG_VS_FAILED_INDUCED_TREG_UP
GSE7568_IL4_VS_IL4_AND_DEXAMETHASONE_TREATED_MACROPHAGE_UP
SHEPARD_BMYB_MORPHOLINO_DN
PID_FOXM1_PATHWAY
GSE13547_2H_VS_12_H_ANTI_IGM_STIM_ZFX_KO_BCELL_DN
GO_DNA_CONFORMATION_CHANGE
RHODES_UNDIFFERENTIATED_CANCER
GSE24574_BCL6_HIGH_VS_LOW_TFH_CD4_TCELL_DN
RB_P107_DN.V1_UP
VANTVEER_BREAST_CANCER_METASTASIS_DN
GSE17301_CTRL_VS_48H_ACD3_ACD28_IFNA2_STIM_CD8_TCELL_DN
GO_NEGATIVE_REGUALTION_OF_CELL_DIVISION
GO_SPINDLE_MIDZONE***
WANG_RESPONSE_TO_GSK3_INHIBITOR_SB216763_DN
GSE25085_FETAL_LIVER_VS_ADULT_BM_SP4_THYMIC_IMPLANT_DN
GSE2405_0H_VS_12H_A_PHAGOCYTOPHILUM_STIM_NEUTROPHIL_DN
GSE15930_NAIVE_VS_24H_IN_VITRO_STIM_INFAB_CD8_TCELL_DN
PID_ATR_PATHWAY
GSE33162_UNTREATED_VS_4H_LPS_STIM_HDAC3_KO_MACROPHAGE_DN
GAL_LEUKEMIC_STEM_CELL_DN
GSE39110_DAY3_VS_DAY6_POST_IMMUNIZATION_CD8_TCELL_WITH_IL2_TREATMENT_UP
GSE33424_CD161_HIGH_VS_NEG_CD8_TCELL_DN
MANALO_HYPOXIA_DN
GSE15930_NAIVE_VS_72H_IN_VITRO_STIM_IFNAB_CD8_TCELL_DN
MITSIADES_RESPONSE_TO_APLIDIN_DN
GSE3982_NKCELL_VS_TH2_DN
GSE3982_DC_VS_MAC_DN
MODULE_158
FRASOR_RESPONSE_TO_SERM_OR_FULVESTRANT_DN
TOYOTA_TARGETS_OF_MIR34B_AND_MIR34C
WONG_EMBRYONIC_STEM_CELL_CORE
GO_CHROMATIN_ASSEMBLY_OR_DISASSEMBLY
GSE15930_NAIVE_VS_72H_IN_VITRO_STIM_CD8_TCELL_DN
MODULE_252
GSE21063_CTRL_VS_ANTI_IGM_STIM_BCELL_16H_UP
GO_REGULATION_OF_CELL_DIVISION
GSE19941_UNSTIM_VS_LPS_AND_IL10_STIM_IL10_KO_MACROPHAGEDN
GO_MITOTIC_SISTER_CHROMATID_SEGREGATION
GSE19941_LPS_VS_LPS_AND_IL10_STIM_IL10_KO_MACROPHAGE_UP
MODULE_125
GSE29614_DAY3_VS_DAY7_TIV_FLU_VACCINE_PBMC_DN
GSE30962_ACUTE_VS_CHRONIC_LCMV_SECONDARY_INF_CD8_TCELL_DN

TABLE 3-continued

Gene datasets shared between Phf19$^{-/-}$ (negatively) and miR-155 cells (positively) (FDR q < 0.25)

GSE45365_WT_VS_IFNAR_KO_BCELL_MCMV_INFECTION_DN
MODULE_397
GNF2_RFC3
FEVR_CTNNB1_TARGETS_DN
REACTOME_MITOTIC_G2_G2_M_PHASES
PRC2_EZH2_UP.V1_UP
GO_CONDENSED_NUCLEAR_CHROMOSOME
GSE25146_UNSTIM_VS_HELIOBACTER_PYLORI_LPS_STIM_AGS_CELL_UP
REACTOME_ACTIVATION_OF_THE_PRE_REPLICATIVE_COMPLEX
CSR_LATE_UP.V1_UP
GO_CYTOSKELETON_DEPENDENT_CYTOKINESIS
GCNP_SHH_UP_LATE.V1_UP
GSE21670_UNTREATED_VS_TGFB_IL6_TREATED_STAT3_KO_CD4_TCELL_UP
GSE16451_CTRL_VS_WEST_EQUINE_ENC_VIRUS_IMMATURE_NEURON_CELL_LINE_DN
GSE20727_DNFB_ALLERGEN_VS_ROS_INH_AND_DNFB_ALLERGEN_TREATED_DC_DN
GSE17301_ACD3_ACD28_VS_ACD3_ACD28_AND_IFNA5_STIM_CD8_TCELL_UP
WEST_ADRENOCORTICAL_TUMOR_UP
GO_MITOTIC_SPINDLE
GSE14699_DELETIONAL_TOLERANCE_VS_ACTIVATED_CD8_TCELL_DN
CONCANNON_APOPTOSIS_BY_EPOXOMICIN_DN
KAECH_DAY8_EFF_VS_DAY15_EFF_CD8_TCELL_UP
GSE39556_UNTREATED_VS_3H_POLYIC_INJ_MOUSE_NK_CELL_UP
GSE5589_IL6_KO_VS_IL10_KO_LPS_AND_IL6_STIM_MACROPHAGE_45MIN_UP
GO_POSITIVE_REGULATION_OF_CELL_DIVISION
BIDUS_METASTASIS_UP
KEGG_CELL_CYCLE
GSE12366_GC_VS_NAIVE_BCELL_UP
MODULE_303
MODULE_244
GO_CHROMOSOME_ORGANIZATION
MORF_BUB1
TARTE_PLASMA_CELL_VS_PLASMABLAST_DN
GO_DNA_REPLICATION_INITIATION
GO_CELL_CYCLE_CHECKPOINT
GSE18203_CTRL_VS_INTRATUMORAL_CPG_INJ_MC38_TUMOR_DN
GSE1460_INTRATHYMIC_T_PROGENITOR_VS_NAIVE_CD4_TCELL_ADULT_BLOOD_UP
MODULE_198
ALCALAY_AML_BY_NPM1_LOCALIZATION_DN
PUJANA_BREAST_CANCER_LIT_INT_NETWORK
SCIBETTA_KDM5B_TARGETS_DN
GO_REGULATION_OF_NUCLEAR_DIVISION
GO_CHROMOSOME
GSE3982_NKCELL_VS_TH1_DN
GSE32164_ALTERNATIVELY_ACT_M2_VS_CMYC_INHIBITED_MACROPHAGE_DN
CASORELLI_ACUTE_PROMYELOCYTIC_LEUKEMIA_DN
GO_PROTEIN_DNA_COMPLEX_SUBUNIT_ORGANIZATION
GSE22886_UNSTIM_VS_IL15_STIM_NKCELL_DN
GRAHAM_CML_QUIESCENT_VS_NORMAL_QUIESCENT_UP
GSE23502_WT_VS_HDC_KO_MYELOID_DERIVED_SUPPRESSOR_CELL_COLON_TUMOR_UP
GO_DNA_SYNTHESIS_INVOLVED_IN_DNA_REPAIR
REACTOME_ACTIVATION_OF_ATR_IN_RESPONSE_TO_REPLICATION_STRESS
PID_AURORA_B_PATHWAY
GO_NEGATIVE_REGULATION_OF_CELL_CYCLE_PROCESS
RODRIGUES_THYROID_CARCINOMA_POORLY_DIFFERENTIATED_UP
MODULE_126
GEORGES_CELL_CYCLE_MIR192_TARGETS
GSE21670_IL6_VS_TGFB_AND_IL6_TREATED_STAT3_KO_CD4_TCELL_UP
GO_CELL_CYCLE_G1_S_PHASE_TRANSITION
REACTOME_G1_S_TRANSITION
GSE5542_IFNA_VS_IFNA_AND_IFNG_TREATED_EPITHELIAL_CELLS_24H_DN
MODULE_403
GSE17186_NAIVE_VS_CD21LOW_TRANSITIONAL_BCELL_CORD_BLOOD_DN
LY_AGING_OLD_DN
GSE13547_WT_VS_ZFX_KO_BCELL_ANTI_IGM_STIM_2H_UP
GSE5503_LIVER_DC_VS_MLN_DC_ACTIVATED_ALLOGENIC_TCELL_UP
KAUFFMANN_DNA_REPLICATION_GENES
GSE17974_CTRL_VS_ACT_IL4_AND_ANTI_IL12_24H_CD4T_CELL_DN
GSE43863_TH1_VS_LY6C_INT_CXCR5POS_EFFECTOR_CD4_TCELL_UP
GO_G1_S_TRANSITION_OF_MITOTIC_CELL_CYCLE
GO_CELL_CYCLE_PHASE_TRANSITION
GSE30962_ACUTE_VS_CHRONIC_LCMV_PRIMARY_INF_CD8_TCELL_DN
GO_REGULATION_OF_DNA_DEPENDENT_DNA_REPLICATION
GO_REGULATION_OF_TRANSCRIPTION_INVOLVED_IN_G1_S_TRANSITION_OF_MITOTIC_CELL_CYCLE
GO_MICROTUBULE_ORGANIZING_CENTER_ORGANIZATION
GO_TELOMERE_MAINTENANCE_VIA_RECOMBINATION
GO_SPINDLE_MICROTUBULE
PETROVA_ENDOTHELIUM_LYMPHATIC_VS_BLOOD_UP
GSE10240_CTRL_VS_IL17_AND_IL22_STIM_PRIMARY_BRONCHIAL_EPITHELIAL_CELLS_UP

TABLE 3-continued

Gene datasets shared between Phf19$^{-/-}$ (negatively) and miR-155 cells (positively) (FDR q < 0.25)

MODULE_485
GO_DNA_DEPENDENT_DNA_REPLICATION
BURTON_ADIPOGENESIS_PEAK_AT_24HR
GO_CHROMATIN_REMODELING
NAKAMURA_CANCER_MICROENVIRONMENT_DN
GSE2770_UNTREATED_VS_IL4_TREATED_ACT_CD4_TCELL_48H_DN
GO_REGULATION_OF_DNA_REPLICATION
GSE40068_BCL6_POS_VS_NEG_CXCR5_POS_TFH_UP
GSE24634_TREG_VS_TCONV_POST_DAY10_IL4_CONVERSION_UP
GO_CYTOKINESIS
GO_MIDBODY
GSE37532_TREG_VS_TCONV_PPARG_KO_CD4_TCELL_FROM_LN_UP
CAIRO_HEPATOBLASTOMA_CLASSES_UP
GSE21546_UNSTIM_VS_ANTI_CD3_STIM_DP_THYMOCYTES_DN
GSE17186_NAIVE_VS_CD21HIGH_TRANSITIONAL_BCELL_DN
GSE41867_NAIVE_VS_EFFECTOR_CD8_TCELL_UP
RIGGI_EWING_SARCOMA_PROGENITOR_DN
GSE5589_WT_VS_IL6_KO_LPS_AND_IL10_STIM_MACROPHAGE_45MIN_UP
WHITFIELD_CELL_CYCLE_S
REACTOME_MITOTIC_G1_G1_S_PHASES
GSE12963_UNINF_VS_ENV_AND_NEF_DEFICIENT_HIV1_INF_CD4_TCELL_DN
GSE7218_IGM_VS_IGG_SIGNAL_THGOUGH_ANTIGEN_BCELL_UP
GO_POSITIVE_REGULATION_OF_CELL_CYCLE_PROCESS
REACTOME_CELL_CYCLE_CHECKPOINTS
GSE5542_IFNG_VS_IFNA_TREATED_EPITHELIAL_CELLS_6H_UP
GSE23568_ID3_KO_VS_WT_CD8_TCELL_UP
GO_NEGATIVE_REGULATION_OF_NUCLEAR_DIVISION
GSE13547_CTRL_VS_ANTI_IGM_STIM_ZFX_KO_BCELL_2H_UP
GSE37301_HEMATOPOIETIC_STEM_CELL_VS_CD4_TCELL_UP
GSE37532_WT_VS_PPARG_KO_LN_TCONV_DN
GO_REGULATION_OF_CYTOKINESIS
GSE19941_UNSTIM_VS_LPS_STIM_IL10_KO_NFKBP50_KO_MACROPHAGE_UP
GSE33424_CD161_HIGH_VS_INT_CD8_TCELL_DN
GSE12963_ENV_NEF_VS_ENV_NEF_AND_VPR_DEFICIENT_HIV1_INF_CD4_TCELL_DN
MODULE_124
GSE24634_NAIVE_CD4_TCELL_VS_DAY7_IL4_CONV_TREG_DN
GO_CHROMOSOME_LOCALIZATION
GSE7460_CTRL_VS_TGFB_TREATED_ACT_TREG_UP
HALLMARK_MITOTIC_SPINDLE
MORI_MATURE_B_LYMPHOCYTE_DN
GSE21546_ELK1_KO_VS_SAP1A_KO_AND_ELK1_KO_DP_THYMOCYTES_DN
GSE40274_CTRL_VS_FOXP3_AND_XBP1_TRANSDUCED_ACTIVATED_CD4_TCELL_UP
MODULE_337
POOLA_INVASIVE_BREAST_CANCER_UP
GSE10239_MEMORY_VS_KLRG1INT_EFF_CD8_TCELL_DN
GSE7509_UNSTIM_VS_IFNA_STIM_IMMATURE_DC_UP
GSE2585_CD80_HIGH_VS_LOW_AIRE_KO_MTEC_DN
PATIL_LIVER_CANCER
GSE28237_FOLLICULAR_VS_EARLY_GC_BCELL_DN
GSE26030_TH1_VS_TH17_RESTIMULATED_DAY15_POST_POLARIZATION_UP
SASAKI_ADULT_T_CELL_LEUKEMIA
GSE10273_LOW_IL7_VS_HIGH_IL7_AND_IRF4_IN_IRF4_8_NULL_PRE_BCELL_UP
GSE7460_CD8_TCELL_VS_TREG_ACT_DN
BENPORATH_ES_1
ZHANG_BREAST_CANCER_PROGENITORS_UP
GSE27786_LIN_NEG_VS_ERYTHROBLAST_DN
GSE10273_HIGH_IL7_VS_HIGH_IL7_AND_IRF4_IN_IRF4_8_NULL_PRE_BCELL_DN
GSE9509_LPS_VS_LPS_AND_IL10_STIM_IL10_KO_MACROPHAGE_20MIN_DN
PYEON_HPV_POSITIVE_TUMORS_UP
MODULE_98
GO_POSITIVE_REGULATION_OF_MITOTIC_CELL_CYCLE
GSE45365_WT_VS_IFNAR_KO_CD11B_DC_DN
GO_DNA_BIOSYNTHETIC_PROCESS
LEE_LIVER_CANCER_SURVIVAL_DN
GSE5142_HTERT_TRANSDUCED_VS_CTRL_CD8_TCELL_LATE_PASSAGE_CLONE_UP
GO_MEIOTIC_CELL_CYCLE_PROCESS
TANG_SENESCENCE_TP53_TARGETS_DN
RHEIN_ALL_GLUCOCORTICOID_THERAPY_DN
GO_MEIOTIC_CHROMOSOME_SEGREGATION***
CHANG_CORE_SERUM_RESPONSE_UP
GO_DNA_INTEGRITY_CHECKPOINT
GO_MEMBRANE_DISASSEMBLY
GSE3039_B2_VS_B1_BCELL_DN
MUELLER_PLURINET
GSE24634_TEFF_VS_TCONV_DAY5_IN_CULTURE_UP
GO_NEGATIVE_REGULATION_OF_CYTOSKELETON_ORGANIZATION
GSE7768_OVA_ALONE_VS_OVA_WITH_MPL_IMMUNIZED_MOUSE_WHOLE_SPLEEN_6H_UP
PID_FANCONI_PATHWAY

TABLE 3-continued

Gene datasets shared between Phf19$^{-/-}$ (negatively) and miR-155 cells (positively) (FDR q < 0.25)

GSE17974_0.5H_VS_72H_UNTREATED_IN_VITRO_CD4_TCELL_DN
GSE3982_EFF_MEMORY_CD4_TCELL_VS_TH2_DN
GSE23505_IL6_IL1_VS_IL6_IL1_IL23_TREATED_CD4_TCELL_UP
KEGG_DNA_REPLICATION
RODRIGUES_THYROID_CARCINOMA_ANAPLASTIC_UP
ZHAN_MULTIPLE_MYELOMA_SUBGROUPS
GO_PROTEIN_LOCALIZATION_TO_CHROMOSOME
NADERI_BREAST_CANCER_PROGNOSIS_UP
GO_NEGATIVE_REGULATION_OF_PROTEIN_COMPLEX_DISASSEMBLY
REACTOME_EXTENSION_OF_TELOMERES
REACTOME_S_PHASE
GSE8685_IL2_STARVED_VS_IL2_ACT_IL2_STARVED_CD4_TCELL_DN
GSE19888_CTRL_VS_A3R_INHIBITOR_TREATED_MAST_CELL_UP
GSE8921_UNSTIM_VS_TLR1_2_STIM_MONOCYTE_6H_DN
GSE24726_WT_VS_E2-2_KO_PDC_UP
GO_POSITIVE_REGULATION_OF_MITOTIC_NUCLEAR_DIVISION
GO_REPLICATION_FORK
GSE24634_TEFF_VS_TCONV_DAY3_IN_CULTURE_UP
GO_NUCLEAR_ENVELOPE_DISASSEMBLY
REACTOME_TELOMERE_MAINTENANCE
REACTOME_DNA_STRAND_ELONGATION
CHIARADONNA_NEOPLASTIC_TRANSFORMATION_KRAS_UP
GO_MITOTIC_RECOMBINATION
SGCGSSAAA_V$E2F1DP2_01
GO_REGULATION_OF_CHROMOSOME_ORGANIZATION
MODULE_438***
LEE_LIVER_CANCER_MYC_E2F1_UP***
BIOCARTA_G2_PATHWAY
GSE40274_FOXP3_VS_FOXP3_AND_SATB1_TRANSDUCED_ACTIVATED_CD4_TCELL_UP***
REACTOME_SYNTHESIS_OF_DNA
GO_REGULATION_OF_MICROTUBULE_BASED_PROCESS
PUJANA_CHEK2_PCC_NETWORK
V$E2F_Q6
MORF_ESPL1
GSE17186_CD21LOW_VS_CD21HIGH_TRANSITIONAL_BCELL_UP
GSE19888_ADENOSINE_A3R_ACT_VS_A3R_ACT_WITH_A3R_INH_PRETREATMENT_IN_MAST_CELL_UP
V$E2F4DP1_01
GSE16450_IMMATURE_VS_MATURE_NEURON_CELL_LINE_DN
GSE32901_TH1_VS_TH17_NEG_CD4_TCELL_DN
GSE6259_FLT3L_INDUCED_DEC205_POS_DC_VS_BCELL_DN
GO_REGULATION_OF_CELL_CYCLE_G2_M_PHASE_TRANSITION
VEGF_A_UP.V1_DN
RAY_TUMORIGENESIS_BY_ERBB2_CDC25A_UP
KEGG_OOCYTE_MEIOSIS
GO_POSITIVE_REGULATION_OF_CHROMOSOME_SEGREGATION
GO_TELOMERE_ORGANIZATION
PID_E2F_PATHWAY
GSE25123_CTRL_VS_IL4_STIM_PPARG_KO_MACROPHAGE_UP
GSE369_SOCS3_KO_VS_IFNG_KO_LIVER_DN
GSE17186_CD21LOW_VS_CD21HIGH_TRANSITIONAL_BCELL_DN
GSE3920_UNTREATED_VS_IFNB_TREATED_ENDOTHELIAL_CELL_DN
GO_MITOTIC_CELL_CYCLE_CHECKPOINT
V$E2F1DP1RB_01
TURASHVILI_BREAST_DUCTAL_CARCINOMA_VS_LOBULAR_NORMAL_UP
GO_POSITIVE_REGULATION_OF_NUCLEAR_DIVISION
GSE27786_LIN_NEG_VS_BCELL_UP
GSE3982_CENT_MEMORY_CD4_TCELL_VS_TH1_DN
GARCIA_TARGETS_OF_FLI1_AND_DAX1_DN
GO_DNA_STRAND_ELONGATION_INVOLVED_IN_DNA_REPLICATION
MODULE_325
REACTOME_M_G1_TRANSITION
HAHTOLA_SEZARY_SYNDROM_UP
GO_DNA_DEPENDENT_ATPASE_ACTIVITY
V$E2F1_Q6
JOHNSTONE_PARVB_TARGETS_3_DN
SESTO_RESPONSE_TO_UV_C7
GO_NEGATIVE_REGULATION_OF_ORGANELLE_ORGANIZATION
GSE21063_3H_VS_16H_ANTI_IGM_STIM_NFATC1_KOBCELL_DN
GSE3982_DC_VS_MAC_LPS_STIM_DN
GO_NEGATIVE_REGULATION_OF_CELL_CYCLE_PHASE_TRANSITION
V$E2F_03
V$E2F_Q4
GO_STRAND_DISPLACEMENT
GO_METAPHASE_PLATE_CONGRESSION
GSE19941_IL10_KO_VS_IL10_KO_AND_NFKBP50_KO_LPS_AND_IL10_STIM_MACROPHAGE_DN
GSE9878_CTRL_VS_EBF_TRANSDUCED_PAX5_KO_PRO_BCELL_DN
GO_MICROTUBULE
GSE22886_UNSTIM_VS_IL2_STIM_NKCELL_DN

TABLE 3-continued

Gene datasets shared between Phf19$^{-/-}$ (negatively) and miR-155 cells (positively) (FDR q < 0.25)

GO_NUCLEAR_ENVELOPE_ORGANIZATION
DELPUECH_FOXO3_TARGETS_DN
KIM_WT1_TARGETS_DN
SMIRNOV_RESPONSE_TO_IR_6HR_DN
V$E2F_Q3_01
OXFORD_RALA_OR_RALB_TARGETS_UP
REACTOME_REGULATION_OF_MITOTIC_CELL_CYCLE
GO_POSTREPLICATION_REPAIR
GO_DNA_STRAND_ELONGATION
GSE17301_CTRL_VS_48H_ACD3_ACD28_IFNA5_STIM_CD8_TCELL_DN***
GSE17301_ACD3_ACD28_VS_ACD3_ACD28_AND_IFNA2_STIMCD8_TCELL_UP
GSE10240_CTRL_VS_IL17_AND_IL22_STIM_PRIMARY_BRONCHIAL_EPITHELIAL_CELLS_DN
GO_REGULATION_OF_DNA_METABOLIC_PROCESS
CUI_TCF21_TARGETS_2_UP
GO_POSITIVE_REGULATION_OF_DNA_REPLICATION
GSE3982_BCELL_VS_TH2_DN
GSE17974_CTRL_VS_ACT_IL4_AND_ANTI_IL12_48H_CD4_TCELL_DN
GSE14415_ACT_VS_CTRL_NATURAL_TREG_UP
GSE22886_NAIVE_CD4_TCELL_VS_12H_ACT_TH1_DN
GSE7218_UNSTIM_VS_ANTIGEN_STIM_THROUGH_IGG_BCELL_UP
GO_CENTROSOME_CYCLE
GSE21670_IL6_VS_TGFB_AND_IL6_TREATED_CD4_TCELL_DN
GNF2_PA2G4
GSE10239_MEMORY_VS_KLRG1HIGH_EFF_CD8_TCELL_DN
GSE23505_UNTREATED_VS_4DAY_IL6_IL1_TREATED_CD4_TCELL_UP
SHETH_LIVER_CANCER_VS_TXNIP_LOSS_PAM5
GSE2405_0H_VS_24H_A_PHAGOCYTOPHILUM_STIM_NEUTROPHIL_DN
V$E2F_Q6_01
GO_MICROTUBULE_CYTOSKELETON
MODULE_308
GSE45365_WT_VS_IFNAR_KO_BCELL_MCMV_INFECTION_UP
GO_REGULATION_OF_MICROTUBULE_POLYMERIZATION_OR_DEPOLYMERIZATION
GSE31082_CD4_VS_CD8_SP_THYMOCYTE_DN
GSE15930_NAIVE_VS_72H_IN_VITRO_STIM_IL12_CD8_TCELL_DN
GSE26351_WNT_VS_BMP_PATHWAY_STIM_HEMATOPOIETIC_PROGENITORS_UP
GO_DNA_HELICASE_ACTIVITY
V$E2F1_Q4_01
GO_MICROTUBULE_CYTOSKELETON_ORGANIZATION
SERVITJA_LIVER_HNF1A_TARGETS_UP
V$E2F1DP1_01
GO_POSITIVE_REGULATION_OF_CELL_CYCLE_PHASE_TRANSITION
GO_DNA_RECOMBINATION
MODULE_197
GSE17721_LPS_VS_CPG_24H_BMDC_DN
GSE33162_UNTREATED_VS_4H_LPS_STIM_HDAC3_KO_MACROPHAGE_UP
VERNELL_RETINOBLASTOMA_PATHWAY_UP
GSE25085_FETAL_LIVER_VS_FETAL_BM_SP4_THYMIC_IMPLANT_UP
BOYAULT_LIVER_CANCER_SUBCLASS_G23_UP
GSE18893_TCONV_VS_TREG_24H_CULTURE_DN
REACTOME_RECRUITMENT_OF_MITOTIC_CENTROSOME_PROTEINS_AND_COMPLEXES
GSE14415_ACT_TCONV_VS_ACT_NATURAL_TREG_DN
GSE10273_HIGH_IL7_VS_HIGH_IL7_AND_IRF4_IN_IRF4_8_NULL_PRE_BCELL_UP
GSE6259_33D1_POS_DC_VS_CD4_TCELL_UP
V$E2F_Q3
KAUFFMANN_DNA_REPAIR_GENES
GSE9650_NAIVE_VS_EFF_CD8_TCELL_DN
SLEBOS_HEAD_AND_NECK_CANCER_WITH_HPV_UP
BHATI_G2M_ARREST_BY_2METHOXYESTRADIOL_UP
GSE27786_ERYTHROBLAST_VS_MONO_MAC_UP
V$E2F1DP2_01
GSE17812_WT_VS_THPOK_KO_MEMORY_CD8_TCELL_DN
V$E2F_02
GSE20715_OH_VS_48H_OZONE_LUNG_DN
GSE3982_CENT_MEMORY_CD4_TCELL_VS_TH2_DN
GSE31082_DP_VS_CD8_SP_THYMOCYTE_UP
GO_MEIOTIC_CELL_CYCLE
GO_POSITIVE_REGULATION_OF_CELL_CYCLE
V$E2F1_Q3
GSE22432_CDC_VS_COMMON_DC_PROGENITOR_DN
GSE36095_WT_VS_HDAC9_KO_TREG_UP
GSE12366_GC_VS_MEMORY_BCELL_UP
GSE10239_KLRG1INT_VS_KLRG1HIGH_EFF_CD8_TCELL_DN
V$E2F4DP2_01
GO_POSITIVE_REGULATION_OF_HISTONE_METHYLATION***
NAKAMURA_TUMOR_ZONE_PERIPHERAL_VS_CENTRAL_UP
GSE1460_DP_THYMOCYTE_VS_NAIVE_CD4_TCELL_ADULT_BLOOD_UP
GEORGES_TARGETS_OF_MIR192_AND_MIR215
GSE3039_CD4_TCELL_VS_NKT_CELL_DN

TABLE 3-continued

Gene datasets shared between Phf19$^{-/-}$ (negatively) and miR-155 cells (positively) (FDR q < 0.25)

GO_NEGATIVE_REGULATION_OF_CELLULAR_PROTEIN_CATABOLIC_PROCESS
GSE41867_DAY8_VS_DAY15_LCMV_CLONE13_EFFECTOR_CD8_TCELL_DN
GO_CYTOSKELETAL_PART
CHIANG_LIVER_CANCER_SUBCLASS_UNANNOTATED_DN
CHIARADONNA_NEOPLASTIC_TRANSFORMATION_KRAS_CDC25_UP
GO_REGULATION_OF_CELL_CYCLE_PROCESS
WANG_CISPLATIN_RESPONSE_AND_XPC_UP
GO_NUCLEAR_CHROMOSOME
GO_ATP_DEPENDENT_DNA_HELICASE_ACTIVITY
GSE32986_UNSTIM_VS_GMCSF_AND_CURDLAN_HIGHDOSE_STIM_DC_UP
MODULE_312
GO_SPINDLE_ASSEMBLY
VANTVEER_BREAST_CANCER_ESR1_DN
GSE15330_HSC_VS_LYMPHOID_PRIMED_MULTIPOTENT_PROGENITOR_DN
GSE27786_LIN_NEG_VS_CD8_TCELL_UP
MORF_RRM1
GSE37416_CTRL_VS_0H_F_TULARENSIS_LVS_NEUTROPHIL_UP***
GO_POSITIVE_REGULATION_OF_DNA_METABOLIC_PROCESS
PAL_PRMT5_TARGETS_UP
BOYAULT_LIVER_CANCER_SUBCLASS_G3_UP
GSE2770_UNTREATED_VS_TGFB_AND_IL12_TREATED_ACT_CD4T_CELL_2H_DN
GSE5503_PLN_DC_VS_SPLEEN_DC_ACTIVATED_ALLOGENIC_TCELL_UP
MODULE_254
GSE9239_CTRL_VS_TNF_INHIBITOR_TREATED_DC_DN
GO_CENTROSOME
SMID_BREAST_CANCER_BASAL_UP
GSE15930_NAIVE_VS_48H_IN_VITRO_STIM_IL12_CD8_TCELL_DN
GSE37532_VISCERAL_ADIPOSE_TISSUE_VS_LN_DERIVED_TCONV_CD4_TCELL_UP
GSE16451_IMMATURE_VS_MATURE_NEURON_CELL_LINE_WEST_EQUINE_ENC_VIRUS_UP
MORF_CCNF
GSE411_WT_VS_SOCS3_KO_MACROPHAGE_UP
KOKKINAKIS_METHIONINE_DEPRIVATION_96HR_DN
THILLAINADESAN_ZNF217_TARGETS_UP
GSE17301_IFNA2_VS_IFNA5_STIM_ACD3_ACD28_ACT_CD8_TCELL_DN
GSE2770_IL12_AND_TGFB_VS_IL4_TREATED_ACT_CD4_TCELL_6H_UP
BOHN_PRIMARY_IMMUNODEFICIENCY_SYNDROM_UP
GSE36888_STAT5_AB_KNOCKIN_VS_WT_TCELL_IL2_TREATED_6H_DN
GNF2_MCM5
REACTOME_G0_AND_EARLY_G1***
RHODES_CANCER_META_SIGNATURE
KUNINGER_IGF1_VS_PDGFB_TARGETS_DN***
TIEN_INTESTINE_PROBIOTICS_24HR_UP
SHETH_LIVER_CANCER_VS_TXNIP_LOSS_PAM3***
CHR2Q33***
GO_CELL_CYCLE_G2_M_PHASE_TRANSITION
GO_MICROTUBULE_ASSOCIATED_COMPLEX
GSE11961_UNSTIM_VS_ANTI_IGM_AND_CD40_STIM_6H_FOLLICULAR_BCELL_UP
LEE_TARGETS_OF_PTCH1_AND_SUFU_UP***
GSE33425_CD8_ALPHAALPHA_VS_ALPHABETA_CD161_HIGH_TCELL_DN
GSE32986_GMCSF_VS_GMCSF_AND_CURDLAN_LOWDOSE_STIM_DC_UP
GSE21063_WT_VS_NFATC1_KO_BCELL_DN
KAECH_NAIVE_VS_DAY8_EFF_CD8_TCELL_DN
GSE17721_CTRL_VS_CPG_24H_BMDC_UP
GSE22601_DOUBLE_POSITIVE_VS_CD8_SINGLE_POSITIVE_THYMOCYTE_DN
GO_POSITIVE_REGULATION_OF_CHROMOSOME_ORGANIZATION
GSE12963_UNINF_VS_ENV_AND_NEF_AND_VPR_DEFICIENT_HIV1_INF_CD4T_CELL_DN
PEDERSEN_METASTASIS_BY_ERBB2_ISOFORM_7
V$E2F_Q4_01
SHIPP_DLBCL_VS_FOLLICULAR_LYMPHOMA_UP
GSE13547_WT_VS_ZFX_KO_BCELL_DN
GSE9037_WT_VS_IRAK4_KO_BMDM_DN
GSE411_WT_VS_SOCS3_KO_MACROPHAGE_IL6_STIM_100MIN_UP
GSE27786_ERYTHROBLAST_VS_NEUTROPHIL_UP
GO_REGULATION_OF_PROTEIN_COMPLEX_DISASSEMBLY
GO_ANAPHASE_PROMOTING_COMPLEX
GO_POSITIVE_REGULATION_OF_FIBROBLAST_PROLIFERATION
GO_NEGATIVE_REGULATION_OF_MITOTIC_CELL_CYCLE
KEGG_PROGESTERONE_MEDIATED_OOCYTE_MATURATION
GO_TRANSLESION_SYNTHESIS
GO_POSITIVE_REGULATION_OF_CHROMATIN_MODIFICATION***
PYEON_CANCER_HEAD_AND_NECK_VS_CERVICAL_UP
PEART_HDAC_PROLIFERATION_CLUSTER_DN
SU_TESTIS
LABBE_WNT3A_TARGETS_UP
GSE13306_RA_VS_UNTREATED_TREG_DN***
GO_MICROTUBULE_ORGANIZING_CENTER
GSE27786_NEUTROPHIL_VS_MONO_MAC_DN
GO_REGULATION_OF_HISTONE_METHYLATION***

TABLE 3-continued

Gene datasets shared between Phf19$^{-/-}$ (negatively) and miR-155 cells (positively) (FDR q < 0.25)

GO_NUCLEUS_ORGANIZATION
GO_REGULATION_OF_CELL_CYCLE_PHASE_TRANSITION
GO_SUPRAMOLECULAR_FIBER
GO_DNA_REPAIR
GSE36826_WT_VS_IL1R_KO_SKIN_STAPH_AUREUS_INF_UP
MODULE_53
GO_INTERCELLULAR_BRIDGE
GO_ANAPHASE_PROMOTING_COMPLEX_DEPENDENT_CATABOLIC_PROCESS
E2F1_UP.V1_UP
GSE7219_WT_VS_NIK_NFKB2_KO_LPS_AND_ANTI_CD40_STIM_DC_UP
GNF2_HAT1
GSE37532_VISCERAL_ADIPOSE_TISSUE_VS_LN_DERIVED_PPARG_KO_TCONV_CD4_TCELL_UP
BURTON_ADIPOGENESIS_PEAK_AT_16HR
GSE20754_WT_VS_TCF1_KO_MEMORY_CD8_TCELL_DN
REACTOME_MEIOSIS
GSE3982_MEMORY_CD4_TCELL_VS_TH2_DN
GSE36078_UNTREATED_VS_AD5_INF_MOUSE_LUNG_DC_DN
WHITFIELD_CELL_CYCLE_G1_S
GO_PROTEIN_COMPLEX_BIOGENESIS
MODULE_18
GO_REGULATION_OF_DNA_RECOMBINATION
GSE13485_CTRL_VS_DAY3_YF17D_VACCINE_PBMC_DN***
GO_MICROTUBULE_BASED_PROCESS
GSE1448_CTRL_VS_ANTI_VALPHA2_DP_THYMOCYTE_UP
BRACHAT_RESPONSE_TO_CAMPTOTHECIN_DN
GSE10239_MEMORY_VS_DAY4.5_EFF_CD8_TCELL_DN
MORF_FEN1
MODULE_52
GSE21546_WT_VS_ELK1_KO_ANTI_CD3_STIM_DP_THYMOCYTES_DN
JOHANSSON_GLIOMAGENESIS_BY_PDGFB_UP
GSE19825_NAIVE_VS_DAY3_EFF_CD8_TCELL_DN
GSE39556_CD8A_DC_VS_NK_CELL_UP
GO_PROTEIN_COMPLEX_ASSEMBLY
GSE40274_CTRL_VS_FOXP3_AND_HELIOS_TRANSDUCED_ACTIVATED_CD4_TCELL_DN
GSE17186_BLOOD_VS_CORD_BLOOD_CD21HIGH_TRANSITIONAL_BCELL_UP
GSE27786_NKCELL_VS_MONO_MAC_DN
GSE6259_CD4_TCELL_VS_CD8_TCELL_UP
GSE28408_LY6G_POS_VS_NEG_DC_DN
GSE34179_THPOK_KO_VS_WT_VA14I_NKTCELL_DN
GO_DNA_METABOLIC_PROCESS
GSE4590_SMALL_VS_VPREB_POS_LARGE_PRE_BCELL_DN
GSE32901_NAIVE_VS_TH17_NEG_CD4_TCELL_DN
PLASARI_TGFB1_TARGETS_10HR_DN
GSE24210_TCONV_VS_TREG_DN
SUNG_METASTASIS_STROMA_DN
MODULE_8
GSE20366_EX_VIVO_VS_DEC205_CONVERSION_NAIVE_CD4_TCELL_UP
GO_DOUBLE_STRAND_BREAK_REPAIR
GSE31082_DP_VS_CD4_SP_THYMOCYTE_UP
GSE17974_1.5H_VS_72H_IL4_AND_ANTI_IL12_ACT_CD4_TCELL_DN
REACTOME_NEP_NS2_INTERACTS_WITH_THE_CELLULAR_EXPORT_MACHINERY
YU_BAP1_TARGETS
GSE27786_LIN_NEG_VS_NKTCELL_UP
GSE42021_CD24HI_VS_CD24LOW_TCONV_THYMUS_UP
GSE21670_TGFB_VS_TGFB_AND_IL6_TREATED_CD4_TCELL_UP
SONG_TARGETS_OF_IE86_CMV_PROTEIN
GSE20727_CTRL_VS_ROS_INH_AND_DNFB_ALLERGEN_TREATED_DC_DN
PID_P73PATHWAY
GRADE_COLON_AND_RECTAL_CANCER_UP
GSE12845_NAIVE_VS_PRE_GC_TONSIL_BCELL_DN
GSE22033_WT_VS_PPARG_KO_MEF_DN
GO_REGULATION_OF_SIGNAL_TRANSDUCTION_BY_P53_CLASS_MEDIATOR
GSE24026_PD1_LIGATION_VS_CTRL_IN_ACT_TCELL_LINE_DN
GSE9988_LPS_VS_LOW_LPS_MONOCYTE_UP
GSE360_HIGH_VS_LOW_DOSE_B_MALAYI_DC_DN
GSE9509_LPS_VS_LPS_AND_IL10_STIM_IL10_KO_MACROPHAGE_30MIN_DN
GSE22886_NAIVE_CD4_TCELL_VS_48H_ACT_TH2_DN
GSE24634_NAIVE_CD4_TCELL_VS_DAY10_IL4_CONV_TREG_DN
VANTVEER_BREAST_CANCER_POOR_PROGNOSIS
GO_MOTOR_ACTIVITY***
GSE17974_CTRL_VS_ACT_IL4_AND_ANTI_IL12_72H_CD4_TCELL_DN
GSE5503_MLN_DC_VS_SPLEEN_DC_ACTIVATED_ALLOGENIC_TCELL_DN
GO_CENTRIOLE_ASSEMBLY
GSE3720_UNSTIM_VS_PMA_STIM_VD2_GAMMADELTA_TCELL_DN
GSE8921_UNSTIM_0H_VS_TLR1_2_STIM_MONOCYTE_6H_UP
GSE8921_UNSTIM_0H_VS_TLR1_2_STIM_MONOCYTE_12H_UP
GSE17974_2H_VS_72H_UNTREATED_IN_VITRO_CD4_TCELL_DN
GSE37532_TREG_VS_TCONV_CD4_TCELL_FROM_VISCERAL_ADIPOSE_TISSUE_DN

TABLE 3-continued

Gene datasets shared between Phf19$^{-/-}$ (negatively) and miR-155 cells (positively) (FDR q < 0.25)

GSE22886_NAIVE_CD4_TCELL_VS_48H_ACT_TH1_DN
GSE1460_NAIVE_CD4_TCELL_ADULT_BLOOD_VS_THYMIC_STROMAL_CELL_DN
GSE2770_UNTREATED_VS_IL4_TREATED_ACT_CD4_TCELL_2H_DN
LEE_BMP2_TARGETS_DN
GSE3982_BCELL_VS_TH1_DN
MORF_RFC4
GSE36476_YOUNG_VS_OLD_DONOR_MEMORY_CD4_TCELL_72H_TSST_ACT_UP
SMIRNOV_RESPONSE_TO_IR_2HR_DN
GO_NUCLEAR_CHROMOSOME_TELOMERIC_REGION
REACTOME_LOSS_OF_NLP_FROM_MITOTIC_CENTROSOMES
GSE15930_NAIVE_VS_48H_IN_VITRO_STIM_CD8_TCELL_DN
GSE7460_CTRL_VS_FOXP3_OVEREXPR_TCONV_UP***
GSE27786_LSK_VS_NKTCELL_UP
GSE21670_STAT3_KO_VS_WT_CD4_TCELL_TGFB_TREATED_DN
GO_PROTEIN_COMPLEX_SUBUNIT_ORGANIZATION
GO_CARBON_CARBON_LYASE_ACTIVITY***
GSE24726_WT_VS_E2-2_KO_PDC_DAY6_POST_DELETION_UP
GSE24634_NAIVE_CD4_TCELL_VS_DAY3_IL4_CONV_TREG_DN
GSE37534_UNTREATED_VS_GW1929_TREATED_CD4_TCELL_PPARG1_AND_FOXP3_TRASDUCED_DN
GO_MITOTIC_SPINDLE_ORGANIZATION
GSE4811_CLASSSICALY_ACTIVATED_VS_TYPE_2_ACTIVATED_MACROPHAGE_UP
LIAO_METASTASIS
MODULE_3
MORF_PCNA
GO_NEGATIVE_REGULATION_OF_CHROMOSOME_ORGANIZATION
GSE360_L_DONOVANI_VS_T_GONDII_DC_DN
GSE2770_UNTREATED_VS_IL4_TREATED_ACT_CD4_TCELL_2H_UP
GSE12507_PDC_CELL_LINE_VS_IMMATUE_T_CELL_LINE_DN
GSE40273_XBP1_KO_VS_WT_TREG_DN
GSE27786_NKTCELL_VS_MONO_MAC_DN
PID_AURORA_A_PATHWAY
BIOCARTA_CELLCYCLE_PATHWAY
GSE13411_PLASMA_CELL_VS_MEMORY_BCELL_UP
GSE32986_UNSTIM_VS_CURDLAN_HIGHDOSE_STIM_DC_UP
V$E2F1_Q6_01
GO_DAMAGED_DNA_BINDING
GSE8835_HEALTHY_VS_CLL_CD4_TCELL_DN
GO_NEGATIVE_REGULATION_OF_CELL_CYCLE
NUNODA_RESPONSE_TO_DASATINIB_IMATINIB_UP
BOYAULT_LIVER_CANCER_SUBCLASS_G123_UP
IVANOVA_HEMATOPOIESIS_LATE_PROGENITOR
GSE32901_NAIVE_VS_TH1_CD4_TCELL_DN
GO_POSITIVE_REGULATION_OF_DNA_BIOSYNTHETIC_PROCESS
GSE41978_WT_VS_ID2_KO_AND_BIM_KO_KLRG1_LOW_EFFECTOR_CD8_TCELL_UP
GO_NEGATIVE_REGULATION_OF_DNA_METABOLIC_PROCESS
SANSOM_APC_TARGETS_REQUIRE_MYC
GSE20715_0H_VS_48H_OZONE_TLR4_KO_LUNG_DN
CHR7P13***
GSE14308_TH1_VS_TH17_UP
GO_CHROMATIN_ORGANIZATION
GO_REGULATION_OF_CYCLIN_DEPENDENT_PROTEIN_KINASE_ACTIVITY
GO_REGULATION_OF_DOUBLE_STRAND_BREAK_REPAIR***
GO_PROTEIN_DNA_COMPLEX
GO_MICROTUBULE_ORGANIZING_CENTER_PART
GO_MEIOSIS_I
REACTOME_REGULATION_OF_GLUCOKINASE_BY_GLUCOKINASE_REGULATORY_PROTEIN
GO_REGULATION_OF_DNA_BIOSYNTHETIC_PROCESS
AMUNDSOM_GENOTOXIC_SIGNATURE
GSE8685_IL15_ACT_IL2_STARVED_VS_IL21_ACT_IL2_STARVED_CD4_TCELL_UP
HALLMARK_SPERMATOGENESIS
GO_CENTROSOME_DUPLICATION
GSE22103_UNSTIM_VS_GMCSF_AND_IFNG_STIM_NEUTROPHIL_DN
GSE7831_1H_VS_4H_CPG_STIM_PDC_DN
GSE18281_PERIMEDULLARY_CORTICAL_REGION_VS_WHOLE_CORTEX_THYMUS_UP
GSE24142_EARLY_THYMIC_PROGENITOR_VS_DN2_THYMOCYTE_ADULT_DN
GO_ORGANELLE_LOCALIZATION
GSE7768_OVA_WITH_LPS_VS_OVA_WITH_MPL_IMMUNIZED_MOUSE_WHOLE_SPLEEN_6H_UP
GSE3982_BASOPHIL_VS_TH2_DN
PICCALUGA_ANGIOIMMUNOBLASTIC_LYMPHOMA_UP***
GSE39022_LN_VS_SPLEEN_DC_UP
GO_MITOTIC_DNA_INTEGRITY_CHECKPOINT
HAMAI_APOPTOSIS_VIA_TRAIL_UP
GO_CHROMATIN_MODIFICATION
GO_CELLULAR_RESPONSE_TO_DNA_DAMAGE_STIMULUS
REACTOME_INTERACTIONS_OF_VPR_WITH_HOST_CELLULAR_PROTEINS
GSE24142_EARLY_THYMIC_PROGENITOR_VS_DN2_THYMOCYTE_DN
GSE12507_PDC_CELL_LINE_VS_IMMATUE_T_CELL_LINE_UP
BIOCARTA_G1_PATHWAY

TABLE 3-continued

Gene datasets shared between Phf19$^{-/-}$ (negatively) and miR-155 cells (positively) (FDR q < 0.25)

GSE29164_CD8_TCELL_VS_CD8_TCELL_AND_IL12_TREATED_MELANOMA_DAY7_DN
GSE18804_SPLEEN_MACROPHAGE_VS_BRAIN_TUMORAL_MACROPHAGE_UP***
BIOCARTA_MPR_PATHWAY
CHR15Q22
ZHONG_RESPONSE_TO_AZACITIDINE_AND_TSA_DN
GO_CELLULAR_RESPONSE_TO_RADIATION
XU_GH1_EXOGENOUS_TARGETS_UP***
MARKEY_RB1_CHRONIC_LOF_UP
GO_REGULATION_OF_PROTEASOMAL_UBIQUITIN_DEPENDENT_PROTEIN_CATABOLIC_PROCESS
GSE5542_IFNG_VS_IFNA_TREATED_EPITHELIAL_CELLS_24H_UP
GSE3982_DC_VS_TH2_DN
GSE21360_SECONDARY_VS_TERTIARY_MEMORY_CD8_TCELL_DN
REACTOME_TRANSPORT_OF_RIBONUCLEOPROTEINS_INTO_THE_HOST_NUCLEUS
GOTZMANN_EPITHELIAL_TO_MESENCHYMAL_TRANSITION_UP***
GO_CYCLIN_DEPENDENT_PROTEIN_KINASE_ACTIVITY
MODULE_17
GO_REGULATION_OF_FIBROBLAST_PROLIFERATION
GSE37563_WT_VS_CTLA4_KO_CD4_TCELL_D4_POST_IMMUNIZATION_DN
GO_ORGANELLE_ASSEMBLY
GSE29618_PRE_VS_DAY7_FLU_VACCINE_MDC_UP***
GSE40655_FOXO1_KO_VS_WT_NTREG_DN
GO_CENTRIOLE
GSE37301_HEMATOPOIETIC_STEM_CELL_VS_COMMON_LYMPHOID_PROGENITOR_DN
GO_ONE_CARBON_METABOLIC_PROCESS***
GO_CARDIAC_MUSCLE_CELL_DIFFERENTIATION***
GSE23505_IL6_IL1_IL23_VS_IL6_1L1_TGFB_TREATED_CD4_TCELL_DN
GO_DNA_DAMAGE_RESPONSE_DETECTION_OF_DNA_DAMAGE
GSE19923_E2A_KO_VS_E2A_AND_HEB_KO_DP_THYMOCYTE_UP
RB_DN.V1_UP
GSE8921_UNSTIM_VS_TLR1_2_STIM_MONOCYTE_3H_UP
CTIP_DN.V1_UP***
GO_REGULATION_OF_CELL_CYCLE
GSE40225_WT_VS_RIP_B7X_DIABETIC_MOUSE_PANCREATIC_CD8_TCELL_DN
GSE4O274_CTRL_VS_XBP1_TRANSDUCED_ACTIVATED_CD4_TCELL_DN
BHATTACHARYA_EMBRYONIC_STEM_CELL
WEI_MYCN_TARGETS_WITH_E_BOX
GSE21670_STAT3_KO_VS_WT_CD4_TCELL_TGFB_TREATED_UP
GO_INTRAMOLECULAR_OXIDOREDUCTASE_ACTIVITY***
GSE29617_CTRL_VS_TIV_FLU_VACCINE_PBMC_2008_DN
GSE42088_UNINF_VS_LEISHMANIA_INF_DC_8H_DN***
GSE41978_WT_VS_ID2_KO_AND_BIM_KO_KLRG1_LOW_EFFECTOR_CD8_TCELL_DN***
GAVIN_FOXP3_TARGETS_CLUSTER_P4***
GSE11961_GERMINAL_CENTER_BCELL_DAY7_VS_GERMINAL_CENTER_BCELL_DAY40_UP
SANSOM_APC_TARGETS_UP
GSE41867_NAIVE_VS_DAY30_LCMV_ARMSTRONG_MEMORY_CD8_TCELL_UP
GSE27786_CD8_TCELL_VS_NKCELL_DN
DUTERTRE_ESTRADIOL_RESPONSE_6HR_UP
V$E2F1_Q4
GSE27786_BCELL_VS_MONO_MAC_DN
GO_REPLISOME
GSE10211_UV_INACT_SENDAI_VS_LIVE_SENDAI_VIRUS_TRACHEAL_EPITHELIAL_CELLS_DN***
GSE3982_DC_VS_TH1_DN
MOHANKUMAR_TLX1_TARGETS_UP
LABBE_TGFB1_TARGETS_DN
GSE7509_UNSTIM_VS_FCGRIIB_STIM_DC_UP
YIH_RESPONSE_TO_ARSENITE_C3
GO_SITE_OF_DOUBLE_STRAND_BREAK
GSE23925_LIGHT_ZONE_VS_DARK_ZONE_BCELL_UP***
GO_DNA_GEOMETRIC_CHANGE
NFE2L2.V2
GSE24972_WT_VS_IRF8_KO_SPLEEN_FOLLICULAR_BCELL_DN
GSE7831_CPG_VS_INFLUENZA_STIM_PDC_4H_DN
GO_ANATOMICAL_STRUCTURE_HOMEOSTASIS
CHR2Q31***
GSE2770_TGFB_AND_IL4_VS_TGFB_AND_IL12-TREATED_ACT_CD4_TCELL_6H_UP***
HOFFMANN_SMALL_PRE_BII_TO_IMMATURE_B_LYMPHOCYTE_DN***
ONO_FOXP3_TARGETS_DN
GO_TRNA_TRANSPORT
GSE20366_EX_VIVO_VS_HOMEOSTATIC_CONVERSION_NAIVE_CD4_TCELL_DN
GSE12845_IGD_NEG_BLOOD_VS_PRE_GC_TONSIL_BCELL_DN
GO_REGULATION_OF_CHROMATIN_ORGANIZATION
GO_REGULATION_OF_REPRODUCTIVE_PROCESS
GSE1460_INTRATHYMIC_T_PROGENITOR_VS_NAIVE_CD4_TCELL_CORD_BLOOD_UP
GSE11961_PLASMA_CELL_DAY7_VS_INVENTORY_BCELL_DAY40_DN***
GSE14308_TH17_VS_NATURAL_TREG_UP***
GSE2770_IL12_VS_IL4_TREATED_ACT_CD4_TCELL_48H_UP
GO_CHROMOSOME_TELOMERIC_REGION
GO_REGULATION_OF_CYTOSKELETON_ORGANIZATION

TABLE 3-continued

Gene datasets shared between Phf19$^{-/-}$ (negatively) and miR-155 cells (positively) (FDR q < 0.25)

CAFFAREL_RESPONSE_TO_THC_24HR_5_DN
GSE36888_UNTREATED_VS_IL2_TREATED_TCELL_2H_UP***
REACTOME_G1_PHASE
GSE360_L_MAJOR_VS_T_GONDII_MAC_DN
GSE14308_TH2_VS_TH17_UP
GSE43955_TH0_VS_TGFB_IL6_IL23_TH17_ACT_CD4_TCELL_52H_UP***
GSE26669_CTRL_VS_COSTIM_BLOCK_MLR_CD4_TCELL_UP
FERRANDO_T_ALL_WITH_MLL_ENL_FUSION_DN
GSE17186_BLOOD_VS_CORD_BLOOD_CD21LOW_TRANSITIONAL_BCELL_DN
GO_AMMONIUM_TRANSPORT***
GSE3920_IFNB_VS_IFNG_TREATED_ENDOTHELIAL_CELL_DN
GSE25123_IL4_VS_IL4_AND_ROSIGLITAZONE_STIM_MACROPHAGE_DAY10_UP
BR0WNE_HCMV_INFECTION_2HR_DN
GSE2128_C57BL6_VS_NOD_THYMOCYTE_UP
GSE26912_TUMORICIDAL_VS_CTRL_MACROPHAGE_DN
GO_NEGATIVE_REGULATION_OF_DNA_REPLICATION
GSE3982_NEUTROPHIL_VS_TH2_DN
GO_BICARBONATE_TRANSPORT***
GO_POSITIVE_REGULATION_OF_CELL_CYCLE_ARREST
GSE14350_TREG_VS_TEFF_DN
CHICAS_RB1_TARGETS_SENESCENT
GSE22432_MULTIPOTENT_VS_COMMON_DC_PROGENITOR_UP
GSE12003_MIR223_KO_VS_WT_BM_PROGENITOR_8D_CULTURE_DN
GSE41087_WT_VS_FOXP3_MUT_ANTI_CD3_CD28_STIM_CD4_TCELL_DN
GO_CELLULAR_RESPONSE_TO_IONIZING_RADIATION
GO_RETROGRADE_VESICLE_MEDIATED_TRANSPORT_GOLGI_TO_ER***
GSE28737_WT_VS_BCL6_KO_MARGINAL_ZONE_BCELL_DN***
GSE25123_WT_VS_PPARG_KO_MACROPHAGE_IL4_STIM_DN
GSE17974_0H_VS_48H_IN_VITRO_ACT_CD4_TCEL_LDN
GSE1925_CTRL_VS_IFNG_PRIMED_MACROPHAGE_UP
GSE25088_WT_VS_STAT6_KO_MACROPHAGE_ROSIGLITAZONE_AND_IL4_STIM_UP
GSE8621_LPS_PRIMED_UNSTIM_VS_LPS_PRIMED_AND_LPS_STIM_MACROPHAGE_DN
GSE24634_TREG_VS_TCONV_POST_DAY5_IL4_CONVERSION_UP
GSE37301_COMMON_LYMPHOID_PROGENITOR_VS_PRO_BCELL_DN
GO_REGULATION_OF_PROTEIN_UBIQUITINATION_INVOLVED_IN_UBIQUITIN_DEPENDENT_PROTEIN_CATABOLIC_PROCESS
GSE8685_IL2_ACT_IL2_STARVED_VS_IL21_ACT_IL2_STARVED_CD4_TCELL_UP***
ACEVEDO_LIVER_CANCER_WITH_H3K27ME3_DN
SANSOM_APC_TARGETS
GO_PALMITOYLTRANSFERASE_ACTIVITY***
REACTOME_METABOLISM_OF_NUCLEOTIDES
CHICAS_RB1_TARGETS_LOW_SERUM
REACTOME_APC_C_CDC20_MEDIATED_DEGRADATION_OF_MITOTIC_PROTEINS
GSE17186_MEMORY_VS_CD21LOW_TRANSITIONAL_BCELL_UP
KEGG_CELL_ADHESION_MOLECULES_CAMS***
REACTOME_INNATE_IMMUNE_SYSTEM***
GSE29164_UNTREATED_VS_CD8_TCELL_AND_IL12_TREATED_MELANOMA_DAY3_DN
GO_S_ACYLTRANSFERASE_ACTIVITY***
GSE27896_HDAC6_KO_VS_WT_TREG_DN
GSE41176_UNSTIM_VS_ANTI_IGM_STIM_TAK1_KO_BCELL_6H_DN***
GSE17974_1H_VS_72H_UNTREATED_IN_VITRO_CD4_TCELL_DN
GO_REGULATION_OF_MITOTIC_CELL_CYCLE
BORCZUK_MALIGNANT_MESOTHELIOMA_UP
MODULE_118
GSE3039_CD4_TCELL_VS_ALPHAALPHA_CD8_TCELL_DN
GSE40273_GATA1_KO_VS_WT_TREG_UP
GO_PROTEIN_PALMITOYLATION***
GSE22601_IMMATURE_CD4_SINGLE_POSITIVE_VS_CD4_SINGLE_POSITIVE_THYMOCYTE_DN***
GSE3982_MEMORY_CD4_TCELL_VS_TH1_DN
MORF_PRKDC
GSE15324_ELF4_KO_VS_WT_NAIVE_CD8_TCELL_UP
GSE43955_TGFB_IL6_VS_TGFB_IL6_IL23_TH17_ACT_CD4_TCELL_60H_DN
GSE16385_MONOCYTE_VS_12H_IL4_TREATED_MACROPHAGE_UP***
GO_REGULATION_OF_CENTROSOME_CYCLE
REACTOME_TRANSPORT_OF_MATURE_MRNA_DERIVED_FROM_AN_INTRONLESS_TRANSCRIPT
GSE6674_CPG_VS_CPG_AND_ANTI_IGM_STIM_BCELL-UP
PRC2_EED_UP.V1_DN
GSE15930_NAIVE_VS_48H_IN_VITRO_STIM_IFNAB_CD8_TCELL_DN
GP_NEGATIVE_REGULATION_OF_GENE_EXPRESSION_EPIGENETIC***
GSE21927_SPLEEN_VS_4T1_TUMOR_MONOCYTE_BALBC_DN
REACTOME_APC_C_CDH1_MEDIATED_DEGRADATION_OF_CDC20_AND_OTHER_APC_C_CDH1_TARGETED_PROTEINS_IN_LATE_
MIT GSE19888_CTRL_VS_A3R_ACTIVATION_MAST_CELL_UP***
GSE27786_CD4_TCELL_VS_MONO_MAC_DN
GSE7460_CTRL_VS_FOXP3_OVEREXPR_TCONV_1_UP
FLECHNER_PBL_KIDNEY_TRANSPLANT_OK_VS_DONOR_DN***
GALE_APL_WITH_FLT3_MUTATED_UP***
GSE21670_UNTREATED_VS_TGFB_TREATED_CD4_TCELL_UP
GSE15624_CTRL_VS_6H_HALOFUGINONE_TREATED_CD4_TCELL_DN

TABLE 3-continued

Gene datasets shared between Phf19$^{-/-}$ (negatively) and miR-155 cells (positively) (FDR q < 0.25)

GSE40277_EOS_AND_LEF1_TRANSDUCED_VS_CTRL_CD4_TCELL_DN
PEART_HDAC_PROLIFERATION_CLUSTER_UP
GO_SIGNAL_TRANSDUCTION_IN_RESPONSE_TO_DNA_DAMAGE
GSE22443_IL2_VS_IL12_TREATED_ACT_CD8_TCELL_DN
GSE17974_IL4_AND_ANTI_IL12_VS_UNTREATED_1H_ACT_CD4_TCELL_DN
GSE3982_EOSINOPHIL_VS_DC_DN
GSE36392_TYPE_2_MYELOID_VS_EOSINOPHIL_IL25_TREATED_LUNG_UP***
HALLMARK_MYC_TARGETS_V1
IRITANI_MAD1_TARGETS_DN
REACTOME_NUCLEOTIDE_BINDING_DOMAIN_LEUCINE_RICH_REPEAT_CONTAINING_RECEPTOR_NLR_
SIGNALING_PATHWAYS***
HOXA9_DN.V1_DN
E2F3_UP.V1_UP
GNF2_TAL1***
GSE3982_EOSINOPHIL_VS_BCELL_DN
CHICAS_RB1_TARGETS_CONFLUENT
MORF_RAD54L
GSE27786_LSK_VS_ERYTHROBLAST_DN
GSE22229_RENAL_TRANSPLANT_IMMUNOSUPP_THERAPY_VS_HEALTHY_PBMC_UP
GSE40277_EOS_AND_LEF1_TRANSDUCED_VS_GATA1_AND_SATB1_TRANSDUCED_CD4_TCELL_DN
GO_REGULATION_OF_ORGANELLE_ORGANIZATION
GENTILE_UV_LOW_DOSE_DN***
GSE6259_FLT3L_INDUCED_33D1_POS_DC_VS_CD4_TCELL_DN
GO_MULTI_ORGANISM_LOCALIZATION
GSE21670_TGFB_VS_TGFB_AND_IL6_TREATED_STAT3_KO_CD4_TCELL_DN
GSE14699_DELETIONAL_TOLERANCE_VS_ACTIVATED_CD8_TCELL_UP
GO_CELLULAR_RESPONSE_TO_ABIOTIC_STIMULUS
GO_MULTI_ORGANISM_TRANSPORT
GSE39820_TGFBETA1_VS_TGFBETA3_IN_IL6_IL23A_TREATED_CD4_TCELL_DN***
COLINA_TARGETS_OF_4EBP1_AND_4EBP2
MORI_EMU_MYC_LYMPHOMA_BY_ONSET_TIME_UP
GO_CELLULAR_AMINO_ACID_BIOSYNTHETIC_PROCESS
GSE9037_WT_VS_IRAK4_KO_LPS_4H_STIM_BMDM_DN
PENG_GLUCOSE_DEPRIVATION_UP
GSE21927_SPLENIC_C26GM_TUMOROUS_VS_4T1_TUMOR_MONOCYTES_UP
INGRAM_SHH_TARGETS_DN***
GSE22886_NAIVE_BCELL_VS_BLOOD_PLASMA_CELL_DN
GSE18791_CTRL_VS_NEWCASTLE_VIRUS_DC_18H_UP
GSE339_CD4POS_VS_CD4CD8DN_DC_DN
GSE13411_NAIVE_BCELL_VS_PLASMA_CELL_DN
RIZ_ERYTHROID_DIFFERENTIATION
GSE25123_ROSIGLITAZONE_VS_IL4_AND_ROSIGLITAZONE_STIM_PPARG_KO_MACROPHAGE_DAY10_UP
GO_REGULATION_OF_DNA_REPAIR
GSE12839_CTRL_VS_IL12_TREATED_PBMC_UP
SNF5_DN.V1_UP
GSE27786_LSK_VS_LIN_NEG_CELL_DN
STEIN_ESRRA_TARGETS_RESPONSIVE_TO_ESTROGEN_DN***
GSE40666_UNTREATED_VS_IFNA_STIM_STAT4_KO_EFFECTOR_CD8_TCELL_90MIN_UP
GSE13762_CTRL_VS_125_VITAMIND_DAY12_DC_UP***
GSE39820_CTRL_VS_TGFBETA3_IL6_IL23A_CD4_TCELL_UP
GSE19401_PAM2CSK4_VS_RETINOIC_ACID_STIM_FOLLICULAR_DC_UP
GO_PEPTIDYL_SERINE_MODIFICATION
GO_RESPONSE_TO_FATTY_ACID***
GSE37301_PRO_BCELL_VS_RAG2_KO_NK_CELL_DN
REACTOME_PURINE_METABOLISM
GSE36476_YOUNG_VS_OLD_DONOR_MEMORY_CD4_TCELL_UP
GSE22611_NOD2_TRANSD_VS_CTRL_TRANSD_HEK293_MDP_STIM_6H_UP
GSE22886_CD8_TCELL_VS_BCELL_NAIVE_DN***
GO_AMINO_ACID_TRANSMEMBRANE_TRANSPORT***
GSE3982_EOSINOPHIL_VS_TH2_DN
YAMAZAKI_TCEB3_TARGETS_DN
REACTOME_METABOLISM_OF_NON_CODING_RNA
GO_MICROTUBULE_BINDING
GSE4535_BM_DERIVED_DC_VS_FOLLICULAR_DC_UP***
GSE17974_0H_VS_72H_IN_VITRO_ACT_CD4T_CELL_DN
GNF2_MAP2K3***
GO_AMINO_ACID_BINDING
EPPERT_PROGENITOR
REACTOME_TRANSPORT_OF_MATURE_TRANSCRIPT_TO_CYTOPLASM
BROWNE_HCMV_INFECTION_14HR_DN
GSE19941_UNSTIM_VS_LPS_AND_IL10_STIM_IL10_KO_NFKBP50_KO_MACROPHAGE_DN
GSE23502_BM_VS_COLON_TUMOR_MYELOID_DERIVED_SUPPRESSOR_CELL_DN***
LU_EZH2_TARGETS_UP***
GSE6875_WT_VS_FOXP3_KO_TREG_DN
GO_REGULATION_OF_TELOMERASE_ACTIVITY***
GSE34205_HEALTHY_VS_RSV_INF_INFANT_PBMC_DN
GO_POST_TRANSLATIONAL_PROTEIN_MODIFICATION***
GSE3982_BASOPHIL_VS_TH1_DN

TABLE 3-continued

Gene datasets shared between Phf19$^{-/-}$ (negatively) and miR-155 cells (positively) (FDR q < 0.25)

GSE22611_NOD2_TRANSDUCED_VS_CTRL_HEK293T_STIMULATED_WITH_MDP_2H_DN
GO_DNA_DIRECTED_DNA_POLYMERASE_ACTIVITY
GNF2_SPTB***
GSE46242_TH1_VS_ANERGIC_TH1_CD4_TCELL_DN***
GSE36078_UNTREATED_VS_AD5_T425A_HEXON_INF_MOUSE_LUNG_DC_DN
REACTOME_GLUCOSE_TRANSPORT
GSE22886_CD4_TCELL_VS_BCELL_NAIVE_DN***
CHR5P15***
GSE27859_MACROPHAGE_VS_CD11C_INT_F480_INT_DC_DN
GSE27241_CTRL_VS_DIGOXIN_TREATED_RORGT_KO_CD4_TCELL_IN_TH17_POLARIZING_CONDITIONS_UP
GO_REGULATION_OF_CELL_CYCLE_ARREST
GSE12845_IGD_POS_VS_NEG_BLOOD_BCELL_DN
HERNANDEZ_MITOTIC_ARREST_BY_DOCETAXEL_1_DN
GO_REPRODUCTION
SHETH_LIVER_CANCER_VS_TXNIP_LOSS_PAM1***
KTGGYRSGAA_UNKNOWN
GSE40274_CTRL_VS_HELIOS_TRANSDUCED_ACTIVATED_CD4_TCELL_UP***
GSE2706_UNSTIM_VS_8H_R848_DC_UP***
GSE21033_3H_VS_24H_POLYIC_STIM_DC_DN
GSE25085_FETAL_LIVER_VS_ADULT_BM_SP4_THYMIC_IMPLANT_UP
GO_CILIARY_BASAL_BODY
GSE26669_CTRL_VS_COSTIM_BLOCK_MLR_CD8_TCELL_UP
GSE33292_DN3_THYMOCYTE_VS_TCELL_LYMPHOMA_FROM_TCF1_KO_DN
GSE17974_0.5H_VS_72H_IL4_AND_ANTI_IL12_ACT_CD4_TCELL_DN
GSE27786_LIN_NEG_VS_NKCELL_UP
GSE29615_DAY3_VS_DAY7_LAIV_FLU_VACCINE_PBMC_UP
MCBRYAN_PUBERTAL_BREAST_6_7WK_DN***
GSE22229_RENAL_TRANSPLANT_VS_HEALTHY_PBMC_UP
GO_POSITIVE_REGULATION_OF_REACTIVE_OXYGEN_SPECIES_METABOLIC_PROCESS***
GO_MACROMOLECULAR_COMPLEX_ASSEMBLY
TCTAGAG, MIR-517***
GO_CARDIOCYTE_DIFFERENTIATION***
GO_REGULATION_OF_RESPONSE_TO_DNA_DAMAGE_STIMULUS
GO_NUCLEAR_REPLICATION_FORK
GSE9316_CD4_TCELL_BALBC_VS_TH17_ENRI_CD4_TCELL_SKG_PMA_IONO_STIM_FR4NEG_UP
GSE13485_PRE_VS_POST_YF17D_VACCINATION_PBMC_DN***
GO_G1_DNA_DAMAGE_CHECKPOINT
GO_RECOMBINATIONAL_REPAIR
GSE25088_CTRL_VS_ROSIGLITAZONE_STIM_MACROPHAGE_DN
GSE21380_TFH_VS_GERMINAL_CENTER_TFH_CD4_TCELL_DN
GO_METHYLATED_HISTONE_BINDING***
GSE17974_CTRL_VS_ACT_IL4_AND_ANTI_IL12_6H_CD4_TCELL_DN
CREIGHTON_ENDOCRINE_THERAPY_RESISTANCE_1
GCM_BECN1***
GSE33425_CD161_HIGH_VS_NEG_CD8_TCELL_DN***
GO_ORGAN_REGENERATION
GSE14308_TH2_VS_NATURAL_TREG_UP
REACTOME_TRNA_AMINOACYLATION
GO_HISTONE_METHYLTRANSFERASE_COMPLEX***
GSE41867_DAY8_VS_DAY15_LCMV_ARMSTRONG_EFFECTOR_CD8_TCELL_DN
GSE2770_IL12_AND_TGFB_VS_IL4_TREATED_ACT_CD4_TCELL_2H_UP***
BOYLAN_MULTIPLE_MYELOMA_C_CLUSTER_UP***
GSE24210_CTRL_VS_IL35_TREATED_TCONV_CD4_TCELL_DN
GSE21927_SPLENIC_C26GM_TUMOROUS_VS_4T1_TUMOR_MONOCYTES_DN***
CHR10Q11***
GSE27786_LSK_VS_BCELL_UP
GNF2_ANK1***
LEE_LIVER_CANCER_MYC_TGFA_DN***
ZWANG_DOWN_BY_2ND_EGF_PULSE
GSE8835_HEALTHY_VS_CLL_CD8_TCELL_UP
GRABARCZYK_BCL11B_TARGETS_DN***
GROSS_HYPOXIA_VIA_ELK3_UP
GSE29949_CD8_NEG_DC_SPLEEN_VS_DC_BRAIN_UP***
GO_PROTEIN_UBIQUITINATION_INVOLVED_IN_UBIQUITIN_DEPENDENT_PROTEIN_CATABOLIC_PROCESS
GO_REGENERATION
GSE40274_CTRL_VS_FOXP3_AND_LEF1_TRANSDUCED_ACTIVATED_CD4_TCELL_DN
GSE27786_LSK_VS_CD8_TCELL_UP
GSE27786_LSK_VS_NKCELL_UP
GSE13484_UNSTIM_VS_YF17D_VACCINE_STIIVI_PBIVIC_DN***
GSE369_SOCS3_KO_VS_WT_LIVER_POST_IL6_INJECTION_UP
GSE27786_NKCELL_VS_ERYTHROBLAST_DN
GSE12845_IGD_POS_BLOOD_VS_DARKZONE_GC_TONSIL_BCELL_DN
GSE24634_TREG_VS_TCONV_POST_DAY3_IL4_CONVERSION_UP
GSE8685_IL2_ACT_IL2_STARVED_VS_IL21_ACT_IL2_STARVED_CD4_TCELL_DN*** datasets are shared unless marked with***

TABLE 4

Gene datasets shared between Phf19<sup>−/−</sup> (positively) and miR-155 cells (negatively) (FDR q < 0.25)

GSE13547_WT_VS_ZFX_KO_BCELL_ANTI_IGM_STIM_12H_DN
ZHENG_IL22_SIGNALING_UP***
AZARE_NEOPLASTIC_TRANSFORMATION_BY_STAT3_UP***
MODULE_188
GO_CARDIAC_CHAMBER_DEVELOPMENT***
ACCATTT, MIR-522***
BOYLAN_MULTIPLE_MYELOMA_PCA1_UP***
ALK_DN.V1_DN
GO_REGULATION_OF_TRANSFORMING_GROWTH_FACTOR_BETA_RECEPTOR_SIGNALING_PATHWAY
JAATINEN_HEMATOPOIETIC_STEM_CELL_DN
GSE39110_DAY3_VS_DAY6_POST_IMMUNIZATION_CD8_TCELL_WITH_IL2_TREATMENT_DN
GSE30962_ACUTE_VS_CHRONIC_LCMV_SECONDARY_INF_CD8_TCELL_UP
BAKKER_FOXO3_TARGETS_UP
GSE17974_0H_VS_72H_IN_VITRO_ACT_CD4_TCELL_UP
GO_GRANULOCYTE_MIGRATION***
GO_REGULATION_OF_CELLULAR_RESPONSE_TO_TRANSFORMING_GROWTH_FACTOR_BETA_STIMULUS
GARGALOVIC_RESPONSE_TO_OXIDIZED_PHOSPHOLIPIDS_BLUE_UP
RAF_UP.V1_UP***
TAVOR_CEBPA_TARGETS_UP***
GSE39110_UNTREATED_VS_IL2_TREATED_CD8_TCELL_DAY3_POST_IMIVIUNIZATION_UP
PICCALUGA_ANGIOIMMUNOBLASTIC_LYMPHOMA_DN
GO_POSITIVE_REGULATION_OF_CELL_GROWTH***
GO_NEGATIVE_REGULATION_OF_TRANSFORMING_GROWTH_FACTOR_BETA_RECEPTOR_SIGNALING_PATHWAY***
CHR1P35***
GO_POSITIVE_REGULATION_OF_INFLAMMATORY_RESPONSE
GO_MYELOID_LEUKOCYTE_MIGRATION***
DAVICIONI_TARGETS_OF_PAX_FOXO1_FUSIONS_DN***
GSE14415_NATURAL_TREG_VS_FOXP3_KO_NATURAL_TREG_DN
GO_NEGATIVE_REGULATION_OF_CELLULAR_RESPONSE_TO_TRANSFORMING_GROWTH_FACTOR_BETA_STIMULUS***
GSE7219_WT_VS_NIK_NFKB2_KO_DC_UP
GSE39110_DAY3_VS_DAY6_POST_IMMUNIZATION_CD8_TCELL_UP
GO_LEUKOCYTE_CHEMOTAXIS*** datasets are shared unless marked with***

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A mammalian T cell, comprising an antigen-specific receptor, wherein the antigen-specific receptor is a T cell receptor (TCR) or a chimeric antigen receptor (CAR), wherein the T cell comprises a genetic expression vector comprising a genetic sequence encoding Phf19.

2. The T cell of claim 1, comprising an antigen-specific receptor, wherein the antigen-specific receptor is a T cell receptor (TCR) or a chimeric antigen receptor (CAR), wherein the T cell comprises a genetic expression vector comprising (a) virally-, bacterially-, or both virally- and bacterially-derived genetic sequences and (b) a genetic sequence encoding Phf19, wherein the genetic sequence encoding Phf19 within the vector is expressed within the T cell.

3. The T cell of claim 1, wherein the T cell is a CD8+ T cell.

4. The T cell of claim 1, wherein the T cell is human.

5. The T cell of claim 1, wherein the Phf19 is a human isoform of Phf19.

6. The T cell of claim 1, wherein the T cell is in vitro or ex vivo.

7. The T cell of claim 1, wherein the antigen-specific receptor has antigenic specificity for a cancer antigen.

8. The T cell of claim 1, wherein the antigen-specific receptor has antigenic specificity for a viral, bacterial, or parasite antigen.

9. The T cell of claim 1, wherein the antigen-specific receptor is a recombinant TCR.

10. The T cell of claim 1, wherein the antigen-specific receptor is an endogenous TCR.

11. The T cell of claim 1, wherein the antigen-specific receptor is a recombinant CAR.

12. A population of T cells comprising at least two T cells of claim 1.

13. A pharmaceutical composition comprising the T cell of claim 1, and a pharmaceutically acceptable carrier.

14. A method for treating cancer or chronic viral disease in a mammal, comprising administering to the mammal an effective amount of the T cell of claim 1, wherein said antigen specific receptor is specific for an antigen associated with the cancer or chronic viral disease in the mammal.

15. The method of claim 14, wherein the cancer is selected from the group consisting of melanoma, leukemia, and HPV carcinoma.

16. The method of claim 14, wherein the T cell is a CD8+ T cell.

17. The method of claim 14, wherein the T cell is human.

* * * * *

SEQUENCE LISTING

<160> NUMBER OF SEQ ID NOS: 29

<210> SEQ ID NO 1
<211> LENGTH: 20
<212> TYPE: DNA
<213> ORGANISM: Artificial Sequence
<220> FEATURE:

<223> OTHER INFORMATION: synthetic

<400> SEQUENCE: 1
tgacagaggg acagttcgtg                                                     20

<210> SEQ ID NO 2
<211> LENGTH: 21
<212> TYPE: DNA
<213> ORGANISM: Artificial Sequence
<220> FEATURE:
<223> OTHER INFORMATION: synthetic

<400> SEQUENCE: 2
gatctcgttc ataggccctg a                                                   21

<210> SEQ ID NO 3
<211> LENGTH: 23
<212> TYPE: RNA
<213> ORGANISM: Mus musculus

<400> SEQUENCE: 3
uuaaugcuaa uugugauagg ggu                                                 23

<210> SEQ ID NO 4
<211> LENGTH: 106
<212> TYPE: DNA
<213> ORGANISM: Homo sapiens

<400> SEQUENCE: 4
gtgctcgctt cggcagcaca tatactaaaa ttggaacgat acagagaaga ttagcatggc         60
ccctgcgcaa ggatgacacg caaattcgtg aagcgttcca tatttt                       106

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
cgaggcatgc tgccccacaa                                                     20

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
agcagggacc accatccgct                                                     20

<210> SEQ ID NO 7
<211> LENGTH: 31
<212> TYPE: PRT
<213> ORGANISM: Mus musculus

<400> SEQUENCE: 7

Ser Lys Val Thr Glu Gly Gln Phe Val Leu Cys Arg Trp Thr Asp Gly
1               5                   10                  15

Leu Tyr Tyr Leu Gly Lys Ile Lys Arg Val Ser Ser Pro Lys Gln
            20                  25                  30

-continued

```
<210> SEQ ID NO 8
<211> LENGTH: 31
<212> TYPE: PRT
<213> ORGANISM: Artificial Sequence
<220> FEATURE:
<223> OTHER INFORMATION: synthetic

<400> SEQUENCE: 8

Ser Lys Val Thr Glu Gly Gln Phe Val Leu Cys Arg Cys Thr Asp Gly
1               5                   10                  15

Leu Tyr Ala Leu Gly Lys Ile Lys Arg Val Ser Ser Pro Lys Gln
            20                  25                  30

<210> SEQ ID NO 9
<211> LENGTH: 580
<212> TYPE: PRT
<213> ORGANISM: Homo sapiens

<400> SEQUENCE: 9

Met Glu Asn Arg Ala Leu Asp Pro Gly Thr Arg Asp Ser Tyr Gly Ala
1               5                   10                  15

Thr Ser His Leu Pro Asn Lys Gly Ala Leu Ala Lys Val Lys Asn Asn
            20                  25                  30

Phe Lys Asp Leu Met Ser Lys Leu Thr Glu Gly Gln Tyr Val Leu Cys
        35                  40                  45

Arg Trp Thr Asp Gly Leu Tyr Tyr Leu Gly Lys Ile Lys Arg Val Ser
    50                  55                  60

Ser Ser Lys Gln Ser Cys Leu Val Thr Phe Glu Asp Asn Ser Lys Tyr
65                  70                  75                  80

Trp Val Leu Trp Lys Asp Ile Gln His Ala Gly Val Pro Gly Glu Glu
                85                  90                  95

Pro Lys Cys Asn Ile Cys Leu Gly Lys Thr Ser Gly Pro Leu Asn Glu
            100                 105                 110

Ile Leu Ile Cys Gly Lys Cys Gly Leu Gly Tyr His Gln Gln Cys His
        115                 120                 125

Ile Pro Ile Ala Gly Ser Ala Asp Gln Pro Leu Leu Thr Pro Trp Phe
    130                 135                 140

Cys Arg Arg Cys Ile Phe Ala Leu Ala Val Arg Lys Gly Gly Ala Leu
145                 150                 155                 160

Lys Lys Gly Ala Ile Ala Arg Thr Leu Gln Ala Val Lys Met Val Leu
                165                 170                 175

Ser Tyr Gln Pro Glu Glu Leu Glu Trp Asp Ser Pro His Arg Thr Asn
            180                 185                 190

Gln Gln Gln Cys Tyr Cys Tyr Cys Gly Gly Pro Gly Glu Trp Tyr Leu
        195                 200                 205

Arg Met Leu Gln Cys Tyr Arg Cys Arg Gln Trp Phe His Glu Ala Cys
    210                 215                 220

Thr Gln Cys Leu Asn Glu Pro Met Met Phe Gly Asp Arg Phe Tyr Leu
225                 230                 235                 240

Phe Phe Cys Ser Val Cys Asn Gln Gly Pro Glu Tyr Ile Glu Arg Leu
                245                 250                 255

Pro Leu Arg Trp Val Asp Val Val His Leu Ala Leu Tyr Asn Leu Gly
            260                 265                 270

Val Gln Ser Lys Lys Lys Tyr Phe Asp Phe Glu Glu Ile Leu Ala Phe
        275                 280                 285

Val Asn His His Trp Glu Leu Leu Gln Leu Gly Lys Leu Thr Ser Thr
    290                 295                 300
```

-continued

```
Pro Val Thr Asp Arg Gly Pro His Leu Leu Asn Ala Leu Asn Ser Tyr
305                 310                 315                 320

Lys Ser Arg Phe Leu Cys Gly Lys Glu Ile Lys Lys Lys Cys Ile
            325                 330                 335

Phe Arg Leu Arg Ile Arg Val Pro Pro Asn Pro Pro Gly Lys Leu Leu
            340                 345                 350

Pro Asp Lys Gly Leu Leu Pro Asn Glu Asn Ser Ala Ser Ser Glu Leu
            355                 360                 365

Arg Lys Arg Gly Lys Ser Lys Pro Gly Leu Leu Pro His Glu Phe Gln
370                 375                 380

Gln Gln Lys Arg Arg Val Tyr Arg Arg Lys Arg Ser Lys Phe Leu Leu
385                 390                 395                 400

Glu Asp Ala Ile Pro Ser Ser Asp Phe Thr Ser Ala Trp Ser Thr Asn
            405                 410                 415

His His Leu Ala Ser Ile Phe Asp Phe Thr Leu Asp Glu Ile Gln Ser
            420                 425                 430

Leu Lys Ser Ala Ser Ser Gly Gln Thr Phe Phe Ser Asp Val Asp Ser
            435                 440                 445

Thr Asp Ala Ala Ser Thr Ser Gly Ser Ala Ser Thr Ser Leu Ser Tyr
450                 455                 460

Asp Ser Arg Trp Thr Val Gly Ser Arg Lys Arg Lys Leu Ala Ala Lys
465                 470                 475                 480

Ala Tyr Met Pro Leu Arg Ala Lys Arg Trp Ala Ala Glu Leu Asp Gly
            485                 490                 495

Arg Cys Pro Ser Asp Ser Ser Ala Glu Gly Ala Ser Val Pro Glu Arg
            500                 505                 510

Pro Asp Glu Gly Ile Asp Ser His Thr Phe Glu Ser Ile Ser Glu Asp
            515                 520                 525

Asp Ser Ser Leu Ser His Leu Lys Ser Ser Ile Thr Asn Tyr Phe Gly
530                 535                 540

Ala Ala Gly Arg Leu Ala Cys Gly Glu Lys Tyr Gln Val Leu Ala Arg
545                 550                 555                 560

Arg Val Thr Pro Glu Gly Lys Val Gln Tyr Leu Val Glu Trp Glu Gly
            565                 570                 575

Thr Thr Pro Tyr
            580

<210> SEQ ID NO 10
<211> LENGTH: 578
<212> TYPE: PRT
<213> ORGANISM: Mus musculus

<400> SEQUENCE: 10

Met Glu Thr Gln Ala Leu Glu Pro Gly Thr Leu Glu Ala Phe Gly Ala
1               5                   10                  15

Thr Ser Pro Asn Lys Gly Gly Leu Ser Lys Thr Lys Lys Asn Phe Lys
            20                  25                  30

Asp Leu Met Ser Lys Val Thr Glu Gly Gln Phe Val Leu Cys Arg Trp
        35                  40                  45

Thr Asp Gly Leu Tyr Tyr Leu Gly Lys Ile Lys Arg Val Ser Ser Pro
    50                  55                  60

Lys Gln Ser Cys Leu Val Thr Phe Glu Asp Asn Ser Lys Tyr Trp Val
65                  70                  75                  80

Leu Trp Lys Asp Ile Gln His Ala Gly Val Pro Gly Glu Glu Pro Lys
```

```
                85                  90                  95
Cys Asp Val Cys Met Gly Lys Thr Ser Gly Pro Met Asn Glu Ile Leu
            100                 105                 110

Ile Cys Gly Lys Cys Gly Leu Gly Tyr His Gln Gln Cys His Ile Pro
            115                 120                 125

Ile Ala Val Asp Ala Asn Trp Pro Leu Leu Thr His Trp Phe Cys Arg
            130                 135                 140

Arg Cys Ile Phe Ala Leu Ala Val Arg Lys Gly Gly Ala Leu Lys Lys
145                 150                 155                 160

Gly Ala Ile Ala Lys Thr Leu Gln Ala Val Lys Met Val Leu Ser Tyr
                165                 170                 175

Gln Pro Glu Glu Leu Asp Trp Asp Ser Pro His Arg Thr Asn Gln Gln
            180                 185                 190

Gln Cys Tyr Cys Tyr Cys Gly Gly Pro Gly Glu Trp Tyr Leu Arg Met
            195                 200                 205

Leu Gln Cys Tyr Arg Cys Arg Gln Trp Phe His Glu Ala Cys Thr Gln
            210                 215                 220

Cys Leu Ser Glu Pro Met Val Phe Gly Asp Arg Phe Tyr Leu Phe Phe
225                 230                 235                 240

Cys Ser Val Cys Asn Gln Gly Pro Glu Tyr Ile Glu Arg Leu Pro Leu
                245                 250                 255

Arg Trp Val Asp Ile Val His Leu Ala Leu Tyr Asn Leu Gly Val Gln
            260                 265                 270

Ser Lys Lys Arg Tyr Phe Asp Phe Glu Glu Ile Leu Ala Phe Val Asn
            275                 280                 285

His His Trp Glu Leu Leu Gln Leu Gly Lys Leu Thr Ser Thr Pro Met
            290                 295                 300

Thr Glu Arg Gly Pro His Leu Leu Asn Ala Leu Asn Ser Tyr Lys Ser
305                 310                 315                 320

Arg Phe Leu Cys Gly Lys Glu Ile Lys Lys Lys Cys Ile Phe Arg
                325                 330                 335

Leu Arg Ile Arg Val Pro Pro Ala Pro Pro Gly Lys Leu Leu Pro Asp
            340                 345                 350

Arg Ala Leu Met Pro Ser Asp Lys Gly Thr Ser Glu Leu Leu Arg Lys
            355                 360                 365

Lys Gly Lys Ser Lys Pro Gly Leu Leu Pro Gln Glu Pro Gln Gln Gln
            370                 375                 380

Lys Arg Arg Val Tyr Arg Arg Lys Ser Lys Phe Leu Leu Glu Asp
385                 390                 395                 400

Ala Ile Pro Ser Ser Asp Phe Thr Ser Ala Trp Ser Thr Asp His His
                405                 410                 415

Leu Ala Ser Ile Phe Asp Phe Thr Leu Asp Glu Ile Gln Ser Leu Lys
            420                 425                 430

Ser Gly Ser Ser Gly Gln Thr Phe Phe Ser Asp Val Asp Ser Thr Asp
            435                 440                 445

Ala Ala Ser Thr Ser Gly Ser Ala Ser Thr Ser Leu Ser Tyr Asp Ser
        450                 455                 460

Arg Trp Thr Val Gly Ser Arg Lys Arg Lys Leu Thr Ala Lys Val His
465                 470                 475                 480

Arg Pro Leu Arg Ala Lys Gln Arg Ala Ala Glu Leu Glu Gly Arg Cys
                485                 490                 495

Ala Ser Asp Ser Asn Ala Glu Gly Ala Val Gly Pro Glu Gln Pro Asp
            500                 505                 510
```

Glu Gly Ile Asp Ser His Thr Leu Glu Ser Ile Ser Gly Asp Asp Ser
    515                 520                 525

Ser Leu Ser His Leu Lys Ser Ser Ile Thr Asn Tyr Phe Gly Ala Ala
    530                 535                 540

Gly Arg Leu Ala Cys Gly Glu Lys Tyr Arg Val Leu Ala Arg Arg Val
545                 550                 555                 560

Thr Pro Glu Gly Lys Val Gln Tyr Leu Leu Glu Trp Glu Gly Thr Thr
                565                 570                 575

Pro Tyr

<210> SEQ ID NO 11
<211> LENGTH: 7956
<212> TYPE: DNA
<213> ORGANISM: Artificial Sequence
<220> FEATURE:
<223> OTHER INFORMATION: synthetic

<400> SEQUENCE: 11

| | | |
|---|---|---|
| tcgagctaag cttcgaatcc tgcagtcgac ggtaccgcgg gcccgggatc cgataaaata | 60 |
| aaagatttta tttagtctcc agaaaaaggg gggaatgaaa gaccccacct gtaggtttgg | 120 |
| caagctagct taagtaacgc cattttgcaa ggcatggaaa atacataact gagaatagag | 180 |
| aagttcagat caaggttagg aacagagaga cagcagaata tgggccaaac aggatatctg | 240 |
| tggtaagcag ttcctgcccc ggctcagggc caagaacaga tggtccccag atgcggtccc | 300 |
| gccctcagca gtttctagag aaccatcaga tgtttccagg gtgccccaag gacctgaaaa | 360 |
| tgaccctgtg ccttatttga actaaccaat cagttcgctt ctcgcttctg ttcgcgcgct | 420 |
| tctgctcccc gagctcaata aaagagccca aacccctca ctcggcgcgc cagtcctccg | 480 |
| atagactgcg tcgcccgggt accgtgtat ccaataaacc ctcttgcagt tgcatccgac | 540 |
| ttgtggtctc gctgttcctt gggagggtct cctctgagtg attgactacc cgtcagcggg | 600 |
| ggtctttcat gggtaacagt ttcttgaagt tggagaacaa cattctgagg gtaggagtcg | 660 |
| aatattaagt aatcctgact caattagcca ctgttttgaa tccacatact ccaatactcc | 720 |
| tgaaatccat cgatggagtt cattatggac agcgcagaaa gagctgggga gaattgtgaa | 780 |
| attgttatcc gctcacaatt ccacacaaca tacgagccgg aagcataaag tgtaaagcct | 840 |
| ggggtgccta atgagtgagc taactcacat taattgcgtt gcgctcactg cccgctttcc | 900 |
| agtcgggaaa cctgtcgtgc cagctgcatt aatgaatcgg ccaacgcgcg gggagaggcg | 960 |
| gtttgcgtat tgggcgctct tccgcttcct cgctcactga ctcgctgcgc tcggtcgttc | 1020 |
| ggctgcggcg agcggtatca gctcactcaa aggcggtaat acggttatcc acagaatcag | 1080 |
| gggataacgc aggaaagaac atgtgagcaa aaggccagca aaaggccagg aaccgtaaaa | 1140 |
| aggccgcgtt gctggcgttt ttccataggc tccgccccc tgacgagcat cacaaaaatc | 1200 |
| gacgctcaag tcagaggtgg cgaaacccga caggactata aagataccag gcgtttcccc | 1260 |
| ctggaagctc cctcgtgcgc tctcctgttc cgaccctgcc gcttaccgga tacctgtccg | 1320 |
| cctttctccc ttcgggaagc gtggcgcttt ctcatagctc acgctgtagg tatctcagtt | 1380 |
| cggtgtaggt cgttcgctcc aagctgggct gtgtgcacga accccccgtt cagcccgacc | 1440 |
| gctgcgcctt atccggtaac tatcgtcttg agtccaaccc ggtaagacac gacttatcgc | 1500 |
| cactggcagc agccactggt aacaggatta gcagagcgag gtatgtaggc ggtgctacag | 1560 |
| agttcttgaa gtggtggcct aactacggct acactagaag gacagtattt ggtatctgcg | 1620 |

```
ctctgctgaa gccagttacc ttcggaaaaa gagttggtag ctcttgatcc ggcaaacaaa    1680
ccaccgctgg tagcggtggt ttttttgttt gcaagcagca gattacgcgc agaaaaaaag    1740
gatctcaaga agatcctttg atcttttcta cggggtctga cgctcagtgg aacgaaaact    1800
cacgttaagg gattttggtc atgagattat caaaaaggat cttcacctag atccttttaa    1860
attaaaaatg aagttttaaa tcaatctaaa gtatatatga gtaaacttgg tctgacagtt    1920
accaatgctt aatcagtgag gcacctatct cagcgatctg tctatttcgt tcatccatag    1980
ttgcctgact ccccgtcgtg tagataacta cgatacggga gggcttacca tctggcccca    2040
gtgctgcaat gataccgcga gacccacgct caccggctcc agatttatca gcaataaacc    2100
agccagccgg aagggccgag cgcagaagtg gtcctgcaac tttatccgcc tccatccagt    2160
ctattaattg ttgccgggaa gctagagtaa gtagttcgcc agttaatagt ttgcgcaacg    2220
ttgttgccat tgctacaggc atcgtggtgt cacgctcgtc gtttggtatg gcttcattca    2280
gctccggttc ccaacgatca aggcgagtta catgatcccc catgttgtgc aaaaaagcgg    2340
ttagctcctt cggtcctccg atcgttgtca gaagtaagtt ggccgcagtg ttatcactca    2400
tggttatggc agcactgcat aattctctta ctgtcatgcc atccgtaaga tgcttttctg    2460
tgactggtga gtactcaacc aagtcattct gagaatagtg tatgcggcga ccgagttgct    2520
cttgcccggc gtcaatacgg gataataccg cgccacatag cagaacttta aaagtgctca    2580
tcattggaaa acgttcttcg gggcgaaaac tctcaaggat cttaccgctg ttgagatcca    2640
gttcgatgta acccactcgt gcacccaact gatcttcagc atcttttact ttcaccagcg    2700
tttctgggtg agcaaaaaca ggaaggcaaa atgccgcaaa aaagggaata agggcgacac    2760
ggaaatgttg aatactcata ctcttccttt ttcaatatta ttgaagcatt tatcagggtt    2820
attgtctcat gagcggatac atatttgaat gtatttagaa aaataaacaa ataggggttc    2880
cgcgcacatt tccccgaaaa gtgccacctg acgtctaaga aaccattatt atcatgacat    2940
taacctataa aaataggcgt atcacgaggc cctttcgtct cgcgcgtttc ggtgatgacg    3000
gtgaaaacct ctgacacatg cagctcccgg agacggtcac agcttgtctg taagcggatg    3060
ccgggagcag acaagcccgt cagggcgcgt cagcgggtgt tggcgggtgt cggggctggc    3120
ttaactatgc ggcatcagag cagattgtac tgagagtgca ccatatgcgg tgtgaaatac    3180
cgcacagatg cgtaaggaga aaataccgca tcaggcgcca ttcgccattc aggctgcgca    3240
actgttggga agggcgatcg gtgcgggcct cttcgctatt acgccagctg gcgaaagggg    3300
gatgtgctgc aaggcgatta agttgggtaa cgccagggtt ttcccagtca cgacgttgta    3360
aaacgacggc cagtgccacg ctctccctta tgcgactcct gcattaggaa gcagcccagt    3420
agtaggttga ggccgttgag caccgccgcc gcaaggaatg gtgcatgcaa ggagatggcg    3480
cccaacagtc ccccggccac ggggcctgcc accatacccca cgccgaaaca gcgctcatg    3540 agcccgaagt ggcgagcccg atcttcccca tcggtgatgt cggcgatata ggcgccagca    3600
accgcacctg tggcgccggt gatgccggcc acgatgcgtc cggcgtagag gcgatttaaa    3660
gacaggatat cagtggtcca ggctctagtt ttgactcaac aatatcacca gctgaagcct    3720
atagagtacg agccatagat aaaataaaag atttttattta gtctccagaa aaaggggggaa   3780 atgaaagacc ccacctgtag gtttggcaag ctagcttaag taacgccatt ttgcaaggca    3840
tggaaaatac ataactgaga atagagaagt tcagatcaag gttaggaaca gagagacagc    3900
agaatatggg ccaaacagga tatctgtggt aagcagttcc tgccccggct cagggccaag    3960
aacagatggt ccccagatgc ggtcccgccc tcagcagttt ctagagaacc atcagatgtt    4020
```

```
tccagggtgc cccaaggacc tgaaaatgac cctgtgcctt atttgaacta accaatcagt    4080
tcgcttctcg cttctgttcg cgcgcttctg ctccccgagc tcaataaaag agcccacaac    4140
ccctcactcg gcgcgccagt cctccgatag actgcgtcgc ccgggtaccc gtattcccaa    4200
taaagcctct tgctgtttgc atccgaatcg tggactcgct gatccttggg agggtctcct    4260
cagattgatt gactgcccac ctcggggggtc tttcatttgg aggttccacc gagatttgga    4320
gaccccctgcc tagggaccac cgaccccccc gccgggaggt aagctggcca gcggtcgttt    4380
cgtgtctgtc tctgtcttttg tgcgtgtttg tgccggcatc taatgtttgc gcctgcgtct    4440
gtactagtta gctaactagc tctgtatctg gcggacccgt ggtggaactg acgagttcgg    4500
aacacccggc cgcaaccctg ggagacgtcc cagggacttc gggggccgtt tttgtggccc    4560
gacctgagtc caaaaatccc gatcgttttg gactcttttgg tgcacccccc ttagaggagg    4620
gatatgtggt tctggtagga gacgagaacc taaaacagtt cccgcctccg tctgaatttt    4680
tgctttcggt ttgggaccga agccgcgccg cgcgtcttgt ctgctgcagc atcgttctgt    4740
gttgtctctg tctgactgtg tttctgtatt tgtctgagaa tatgggcccg gctagcctg    4800
ttaccactcc cttaagtttg accttaggtc actggaaaga tgtcgagcgg atcgctcaca    4860
accagtcggt agatgtcaag aagagacgtt gggttacctt ctgctctgca gaatggccaa    4920
cctttaacgt cggatggccg cgagacggca ccttttaaccg agacctcatc acccaggtta    4980
agatcaaggt cttttcacct ggcccgcatg gacacccaga ccaggtcccc tacatcgtga    5040
cctgggaagc cttggctttt gaccccccctc cctgggtcaa gcccctttgta caccctaagc    5100
ctccgcctcc tcttcctcca tccgcccgt ctctccccct tgaacctcct cgttcgaccc    5160
cgcctcgatc ctcccttttat ccagccctca ctccttctct aggcgccccc atatggccat    5220
atgagatctt atatggggca cccccgcccc ttgtaaactt ccctgaccct gacatgacaa    5280
gagttactaa cagcccctct ctccaagctc acttacaggc tctctactta gtccagcacg    5340
aagtctggag acctctggcg gcagcctacc aagaacaact ggaccgaccg gtggtacctc    5400
accccttaccg agtcggcgac acagtgtggg tccgccgaca ccagactaag aacctagaac    5460
ctcgctggaa aggaccttac acagtcctgc tgaccacccc caccgccctc aaagtagacg    5520
gcatcgcagc ttggatacac gccgcccacg tgaaggctgc cgaccccggg ggtggaccat    5580
cctctagacc gccatggaga ctcaagctct ggaaccaggg actctggaag cctttggtgc    5640
caccagtcct aacaaggggg gcctgtctaa gaccaaaaag aacttcaaag acttgatgtc    5700
taaggtgaca gagggacagt tcgtgctatg caggtggaca gacgggctat attaccttgg    5760
caagatcaag cgggtcagca gtcctaagca aagctgcctt gtgacttttg aagataattc    5820
caaatactgg gtcctgtgga aggacatcca gcatgctggt gttccgggag aggagcccaa    5880
gtgtgacgtc tgcatgggga agacttcagg gcctatgaac gagatcctca tctgtgggaa    5940
gtgtggcctg ggtaccacc aacagtgcca catccccatc gcagttgatg ccaactggcc    6000
cctcctcact cattggttct gccgacgctg cattttcgca ctggctgtga ggaaaggtgg    6060
cgctttgaag aaaggcgcca tcgccaagac gctgcaggca gtgaaaatgg tgctgtccta    6120
ccagccggag gaactcgatt gggactcgcc ccatcgcact aaccagcagc aatgctactg    6180
ctactgcggc gggcctggag agtggtacct tcggatgcta cagtgctacc ggtgtaggca    6240
gtggttccat gaggcttgca cacagtgcct tagtgagcct atggtgtttg gagaccgctt    6300
ctacctgttc ttctgctccg tgtgtaacca aggcccagag tatattgaga ggctgcccctt    6360
```

```
gcgatgggtg atatagttc  acctggctct ctataacttg ggagtacaga gcaagaagcg    6420
gtactttgac tttgaggaga tcctggcctt tgtcaaccat cactgggagc tcctgcagct    6480
tggcaagctc accagcaccc ccatgacaga acgagggcca catctcctca acgctctcaa    6540
cagttacaag agccggttcc tgtgtggcaa ggaaattaag aagaagaaat gcatcttccg    6600
actgcgcatc cgagtcccgc ctgcccctcc aggaaaactg cttcccgaca gggcgttgat    6660
gccaagtgac aaagggacct ccgagctgct tcgtaagaaa ggaaagagca agcctggttt    6720
gttgcctcag gaaccccagc agcagaaaag gcgagtttat agaagaaaaa gatcaaagtt    6780
tttgctggaa gatgctattc ccagtagtga cttcacctca gcctggagca cagaccacca    6840
cctagccagt atattcgact tcacactgga tgaaattcag agtttaaaaa gtggcagctc    6900
aggccagacc ttcttctcag atgtggattc taccgacgca gccagcacct cggggtctgc    6960
ctccaccagc ctctcctacg actccagatg gacggtaggc agccgcaaga ggaagctgac    7020
agccaaagtg cacaggcccc tgcgagcaaa gcaaagggcg gcggagctgg aggggcgctg    7080
cgcctcagac agcaatgcag agggagctgt gggtcctgag cagccggatg aaggcatcga    7140
cagccacaca cttgaaagca tcagtggaga cgactcgtcc ctgtcccacc tcaagtcctc    7200
tatcaccaac tactttggtg cagctgggcg gttggcctgc ggggaaaaat atcgggtgtt    7260
ggcgcggagg gtcactccag aaggcaaggt tcagtacctg ttggaatggg aggggaccac    7320
cccttacggt aagcctatcc ctaaccctct cctcggtctc gattctacgg cgaattcacg    7380
tgccaagcga agcggaagcg gagagggcag aggaagtctg ctaacatgcg gtgacgtcga    7440
ggagaatcct ggcccagcta gcaacccagc catcagcgtc gctctcctgc tctcagtctt    7500
gcaggtgtcc cgagggcaga aggtgaccag cctgacagcc tgcctggtga accaaaacct    7560
tcgcctggac tgccgccatg agaataacac caaggataac tccatccagc atgagttcag    7620
cctgacccga gagaagagga agcacgtgct ctcaggcacc ctcgggatac ccgagcacac    7680
gtaccgctcc cgcgtcaccc tctccaacca gccctatatc aaggtcctta ccctagccaa    7740
cttcaccacc aaggatgagg cgactacttt tgtgagcttt cgagtctcgg cgcgaatcc    7800
catgagctca aataaaagta tcagtgtgta tagagacaaa ctggtcaagt gtggcggcat    7860
aagcctgctg gttcagaaca catcctggat gctgctgctg ctgctttccc tctccctcct    7920
ccaagccctg gacttcattt ctctgtgagc ggccgc                              7956
```

<210> SEQ ID NO 12
<211> LENGTH: 130
<212> TYPE: PRT
<213> ORGANISM: Homo sapiens

<400> SEQUENCE: 12

```
Met Glu Asn Arg Ala Leu Asp Pro Gly Thr Arg Asp Ser Tyr Gly Ala
1               5                   10                  15

Thr Ser His Leu Pro Asn Lys Gly Ala Leu Ala Lys Val Lys Asn Asn
            20                  25                  30

Phe Lys Asp Leu Met Ser Lys Leu Thr Glu Gly Gln Tyr Val Leu Cys
        35                  40                  45

Arg Trp Thr Asp Gly Leu Tyr Tyr Leu Gly Lys Ile Lys Arg Val Ser
    50                  55                  60

Ser Ser Lys Gln Ser Cys Leu Val Thr Phe Glu Asp Asn Ser Lys Tyr
65                  70                  75                  80

Trp Val Leu Trp Lys Asp Ile Gln His Ala Gly Val Pro Gly Glu Glu
                85                  90                  95
```

```
Pro Lys Cys Asn Ile Cys Leu Gly Lys Thr Ser Gly Pro Leu Asn Glu
            100                 105                 110

Ile Leu Ile Cys Gly Lys Cys Gly Leu Val Pro His Pro His Ser Gly
            115                 120                 125

Gln Cys
    130

<210> SEQ ID NO 13
<211> LENGTH: 370
<212> TYPE: PRT
<213> ORGANISM: Homo sapiens

<400> SEQUENCE: 13

Met Leu Gln Cys Tyr Arg Cys Arg Gln Trp Phe His Glu Ala Cys Thr
1               5                   10                  15

Gln Cys Leu Asn Glu Pro Met Met Phe Gly Asp Arg Phe Tyr Leu Phe
            20                  25                  30

Phe Cys Ser Val Cys Asn Gln Gly Pro Glu Tyr Ile Glu Arg Leu Pro
            35                  40                  45

Leu Arg Trp Val Asp Val Val His Leu Ala Leu Tyr Asn Leu Gly Val
            50                  55                  60

Gln Ser Lys Lys Lys Tyr Phe Asp Phe Glu Glu Ile Leu Ala Phe Val
65                  70                  75                  80

Asn His His Trp Glu Leu Leu Gln Leu Gly Lys Leu Thr Ser Thr Pro
                85                  90                  95

Val Thr Asp Arg Gly Pro His Leu Leu Asn Ala Leu Asn Ser Tyr Lys
            100                 105                 110

Ser Arg Phe Leu Cys Gly Lys Glu Ile Lys Lys Lys Cys Ile Phe
            115                 120                 125

Arg Leu Arg Ile Arg Val Pro Pro Asn Pro Gly Lys Leu Leu Pro
130                 135                 140

Asp Lys Gly Leu Leu Pro Asn Glu Asn Ser Ala Ser Ser Glu Leu Lys
145                 150                 155                 160

Arg Gly Lys Ser Lys Pro Gly Leu Leu Pro His Glu Phe Gln Gln Gln
                165                 170                 175

Lys Arg Arg Val Tyr Arg Arg Lys Arg Ser Lys Phe Leu Leu Glu Asp
            180                 185                 190

Ala Ile Pro Ser Ser Asp Phe Thr Ser Ala Trp Ser Thr Asn His His
            195                 200                 205

Leu Ala Ser Ile Phe Asp Phe Thr Leu Asp Glu Ile Gln Ser Leu Lys
            210                 215                 220

Ser Ala Ser Ser Gly Gln Thr Phe Phe Ser Asp Val Asp Ser Thr Asp
225                 230                 235                 240

Ala Ala Ser Thr Ser Gly Ser Ala Ser Thr Ser Leu Ser Tyr Asp Ser
                245                 250                 255

Arg Trp Thr Val Gly Ser Arg Lys Arg Lys Leu Ala Ala Lys Ala Tyr
            260                 265                 270

Met Pro Leu Arg Ala Lys Arg Trp Ala Ala Glu Leu Asp Gly Arg Cys
            275                 280                 285

Pro Ser Asp Ser Ser Ala Glu Gly Ala Ser Val Pro Glu Arg Pro Asp
            290                 295                 300

Glu Gly Ile Asp Ser His Thr Phe Glu Ser Ile Ser Glu Asp Asp Ser
305                 310                 315                 320

Ser Leu Ser His Leu Lys Ser Ser Ile Thr Asn Tyr Phe Gly Ala Ala
```

```
                    325                 330                 335
Gly Arg Leu Ala Cys Gly Glu Lys Tyr Gln Val Leu Ala Arg Arg Val
                340                 345                 350
Thr Pro Glu Gly Lys Val Gln Tyr Leu Val Glu Trp Glu Gly Thr Thr
            355                 360                 365
Pro Tyr
    370

<210> SEQ ID NO 14
<211> LENGTH: 599
<212> TYPE: PRT
<213> ORGANISM: Homo sapiens

<400> SEQUENCE: 14

Met Leu Val Leu Val Ile Arg Gly Pro Tyr Pro Ser Ala Gln Cys Gln
1               5                   10                  15
Gly Lys Leu Met Glu Asn Arg Ala Leu Asp Pro Gly Thr Arg Asp Ser
                20                  25                  30
Tyr Gly Ala Thr Ser His Leu Pro Asn Lys Gly Ala Leu Ala Lys Val
            35                  40                  45
Lys Asn Asn Phe Lys Asp Leu Met Ser Lys Leu Thr Glu Gly Gln Tyr
50                  55                  60
Val Leu Cys Arg Trp Thr Asp Gly Leu Tyr Tyr Leu Gly Lys Ile Lys
65                  70                  75                  80
Arg Val Ser Ser Ser Lys Gln Ser Cys Leu Val Thr Phe Glu Asp Asn
                85                  90                  95
Ser Lys Tyr Trp Val Leu Trp Lys Asp Ile Gln His Ala Gly Val Pro
            100                 105                 110
Gly Glu Glu Pro Lys Cys Asn Ile Cys Leu Gly Lys Thr Ser Gly Pro
        115                 120                 125
Leu Asn Glu Ile Leu Ile Cys Gly Lys Cys Gly Leu Gly Tyr His Gln
    130                 135                 140
Gln Cys His Ile Pro Ile Ala Gly Ser Ala Asp Gln Pro Leu Leu Thr
145                 150                 155                 160
Pro Trp Phe Cys Arg Arg Cys Ile Phe Ala Leu Ala Val Arg Lys Gly
                165                 170                 175
Gly Ala Leu Lys Lys Gly Ala Ile Ala Arg Thr Leu Gln Ala Val Lys
            180                 185                 190
Met Val Leu Ser Tyr Gln Pro Glu Glu Leu Glu Trp Asp Ser Pro His
        195                 200                 205
Arg Thr Asn Gln Gln Cys Tyr Cys Tyr Cys Gly Gly Pro Gly Glu Trp
    210                 215                 220
Trp Tyr Leu Arg Met Leu Gln Cys Tyr Arg Cys Arg Gln Trp Phe His
225                 230                 235                 240
Glu Ala Cys Thr Gln Cys Leu Asn Glu Pro Met Met Phe Gly Asp Arg
                245                 250                 255
Phe Tyr Leu Phe Phe Cys Ser Val Cys Asn Gln Gly Pro Glu Tyr Ile
            260                 265                 270
Glu Arg Leu Pro Leu Arg Trp Val Asp Val Val His Leu Ala Leu Tyr
        275                 280                 285
Asn Leu Gly Val Gln Ser Lys Lys Lys Tyr Phe Asp Phe Glu Glu Ile
    290                 295                 300
Leu Ala Phe Val Asn His His Trp Glu Leu Leu Gln Leu Gly Lys Leu
305                 310                 315                 320
```

```
Thr Ser Thr Pro Val Thr Asp Arg Gly Pro His Leu Leu Asn Ala Leu
            325                 330                 335

Asn Ser Tyr Lys Ser Arg Phe Leu Cys Gly Lys Glu Ile Lys Lys Lys
        340                 345                 350

Lys Cys Ile Phe Arg Leu Arg Ile Arg Val Pro Pro Asn Pro Pro Gly
            355                 360                 365

Lys Leu Leu Pro Asp Lys Gly Leu Leu Pro Asn Glu Asn Ser Ala Ser
        370                 375                 380

Ser Glu Leu Arg Lys Arg Gly Lys Ser Lys Pro Gly Leu Leu Pro His
385                 390                 395                 400

Glu Phe Gln Gln Gln Lys Arg Val Tyr Arg Arg Lys Arg Ser Lys
                405                 410                 415

Phe Leu Leu Glu Asp Ala Ile Pro Ser Ser Asp Phe Thr Ser Ala Trp
            420                 425                 430

Ser Thr Asn His His Leu Ala Ser Ile Phe Asp Phe Thr Leu Asp Glu
        435                 440                 445

Ile Gln Ser Leu Lys Ser Ala Ser Ser Gly Gln Thr Phe Phe Ser Asp
    450                 455                 460

Val Asp Ser Thr Asp Ala Ala Ser Thr Ser Gly Ser Ala Ser Thr Ser
465                 470                 475                 480

Leu Ser Tyr Asp Ser Arg Trp Thr Val Gly Ser Arg Lys Arg Lys Leu
                485                 490                 495

Ala Ala Lys Ala Tyr Met Pro Leu Arg Ala Lys Arg Trp Ala Ala Glu
            500                 505                 510

Leu Asp Gly Arg Cys Pro Ser Asp Ser Ser Ala Glu Gly Ala Ser Val
        515                 520                 525

Pro Glu Arg Pro Asp Glu Gly Ile Asp Ser His Thr Phe Glu Ser Ile
530                 535                 540

Ser Glu Asp Asp Ser Ser Leu Ser His Leu Lys Ser Ser Ile Thr Asn
545                 550                 555                 560

Tyr Phe Gly Ala Ala Gly Arg Leu Ala Cys Gly Glu Lys Tyr Gln Val
                565                 570                 575

Leu Ala Arg Arg Val Thr Pro Glu Gly Lys Val Gln Tyr Leu Val Glu
            580                 585                 590

Trp Glu Gly Thr Thr Pro Tyr
            595
```

<210> SEQ ID NO 15
<211> LENGTH: 207
<212> TYPE: PRT
<213> ORGANISM: Homo sapiens

<400> SEQUENCE: 15

```
Met Glu Asn Arg Ala Leu Asp Pro Gly Thr Arg Asp Ser Tyr Gly Ala
1               5                   10                  15

Thr Ser His Leu Pro Asn Lys Gly Ala Leu Ala Lys Val Lys Asn Asn
                20                  25                  30

Phe Lys Asp Leu Met Ser Lys Leu Thr Glu Gly Gln Tyr Val Leu Cys
            35                  40                  45

Arg Trp Thr Asp Gly Leu Tyr Tyr Leu Gly Lys Ile Lys Arg Val Ser
        50                  55                  60

Ser Ser Lys Gln Ser Cys Leu Val Thr Phe Glu Asp Asn Ser Lys Tyr
65                  70                  75                  80

Trp Val Leu Trp Lys Asp Ile Gln His Ala Gly Val Pro Gly Glu Glu
                85                  90                  95
```

```
Pro Lys Cys Asn Ile Cys Leu Gly Lys Thr Ser Gly Pro Leu Asn Glu
            100                 105                 110

Ile Leu Ile Cys Gly Lys Cys Gly Leu Gly Tyr His Gln Gln Cys His
        115                 120                 125

Ile Pro Ile Ala Gly Ser Ala Asp Gln Pro Leu Leu Thr Pro Trp Phe
    130                 135                 140

Cys Arg Arg Cys Ile Phe Ala Leu Ala Val Arg Val Ser Leu Pro Ser
145                 150                 155                 160

Ser Pro Val Pro Ala Ser Pro Ala Ser Ser Gly Ala Asp Gln Arg
            165                 170                 175

Leu Pro Ser Gln Ser Leu Ser Ser Lys Gln Lys Gly His Thr Trp Ala
            180                 185                 190

Leu Glu Thr Asp Ser Ala Ser Ala Thr Val Leu Gly Gln Asp Leu
            195                 200                 205

<210> SEQ ID NO 16
<211> LENGTH: 22
<212> TYPE: DNA
<213> ORGANISM: Artificial Sequence
<220> FEATURE:
<223> OTHER INFORMATION: synthetic

<400> SEQUENCE: 16
agtgacttgg attttccagc ac                                    22

<210> SEQ ID NO 17
<211> LENGTH: 21
<212> TYPE: DNA
<213> ORGANISM: Artificial Sequence
<220> FEATURE:
<223> OTHER INFORMATION: synthetic

<400> SEQUENCE: 17
aattctgttg taagggcgac c                                     21

<210> SEQ ID NO 18
<211> LENGTH: 20
<212> TYPE: DNA
<213> ORGANISM: Mus musculus

<400> SEQUENCE: 18
gagcttgctc taggggtagg                                       20

<210> SEQ ID NO 19
<211> LENGTH: 20
<212> TYPE: DNA
<213> ORGANISM: Mus musculus

<400> SEQUENCE: 19
acagccagaa gtaaggtccc                                       20

<210> SEQ ID NO 20
<211> LENGTH: 20
<212> TYPE: DNA
<213> ORGANISM: Mus musculus

<400> SEQUENCE: 20
cgccacaatt ccgaccttag                                       20

<210> SEQ ID NO 21
<211> LENGTH: 20
```

<212> TYPE: DNA
<213> ORGANISM: Mus musculus

<400> SEQUENCE: 21
aaatatttgc ggcgctccat                                               20

<210> SEQ ID NO 22
<211> LENGTH: 20
<212> TYPE: DNA
<213> ORGANISM: Mus musculus

<400> SEQUENCE: 22
ttggggcaca gataccatgt                                               20

<210> SEQ ID NO 23
<211> LENGTH: 20
<212> TYPE: DNA
<213> ORGANISM: Mus musculus

<400> SEQUENCE: 23
tcctccctag actcaagcct                                               20

<210> SEQ ID NO 24
<211> LENGTH: 20
<212> TYPE: DNA
<213> ORGANISM: Mus musculus

<400> SEQUENCE: 24
ctgcagacat tttgaggcgt                                               20

<210> SEQ ID NO 25
<211> LENGTH: 20
<212> TYPE: DNA
<213> ORGANISM: Mus musculus

<400> SEQUENCE: 25
tctaactgag ccggtgttgt                                               20

<210> SEQ ID NO 26
<211> LENGTH: 20
<212> TYPE: DNA
<213> ORGANISM: Mus musculus

<400> SEQUENCE: 26
tggttgttct agggcgtgat                                               20

<210> SEQ ID NO 27
<211> LENGTH: 20
<212> TYPE: DNA
<213> ORGANISM: Mus musculus

<400> SEQUENCE: 27
tacccggcca aactctcaat                                               20

<210> SEQ ID NO 28
<211> LENGTH: 20
<212> TYPE: DNA
<213> ORGANISM: Mus musculus

<400> SEQUENCE: 28
tgaaattcca cctccctccc                                               20

<210> SEQ ID NO 29

```
<211> LENGTH: 20
<212> TYPE: DNA
<213> ORGANISM: Mus musculus

<400> SEQUENCE: 29
tccctttaac tttcgcccct                                          20
```